(12) United States Patent
Bahou et al.

(10) Patent No.: US 10,947,514 B2
(45) Date of Patent: Mar. 16, 2021

(54) ADENO-ASSOCIATED-VIRUS REP SEQUENCES, VECTORS AND VIRUSES

(71) Applicant: The Research Foundation For The State University Of New York, Albany, NY (US)

(72) Inventors: Wadie F. Bahou, Setauket, NY (US); Patrick Hearing, Saint James, NY (US); Varsha Sitaraman, Stony Brook, NY (US)

(73) Assignee: The Research Foundation For The State University Of New York, Albany, NY (US)

( * ) Notice: Subject to any disclaimer, the term of this patent is extended or adjusted under 35 U.S.C. 154(b) by 57 days.

(21) Appl. No.: 16/254,758

(22) Filed: Jan. 23, 2019

(65) Prior Publication Data
US 2019/0292525 A1    Sep. 26, 2019

Related U.S. Application Data

(63) Continuation of application No. 14/795,214, filed on Jul. 9, 2015, now Pat. No. 10,214,730, which is a continuation of application No. 14/112,703, filed as application No. PCT/US2012/034247 on Apr. 19, 2012, now abandoned.

(60) Provisional application No. 61/476,858, filed on Apr. 19, 2011.

(51) Int. Cl.
| | |
|---|---|
| *C12N 7/00* | (2006.01) |
| *A61K 38/46* | (2006.01) |
| *C07K 14/005* | (2006.01) |
| *C12N 15/86* | (2006.01) |
| *C12N 9/16* | (2006.01) |
| *C12N 9/22* | (2006.01) |
| *C12Q 1/6897* | (2018.01) |
| *A61K 39/00* | (2006.01) |

(52) U.S. Cl.
CPC .............. *C12N 7/00* (2013.01); *A61K 38/465* (2013.01); *C07K 14/005* (2013.01); *C12N 9/16* (2013.01); *C12N 9/22* (2013.01); *C12N 15/86* (2013.01); *C12Q 1/6897* (2013.01); *A61K 2039/5256* (2013.01); *C12N 2710/10021* (2013.01); *C12N 2710/10033* (2013.01); *C12N 2710/10041* (2013.01); *C12N 2710/10052* (2013.01); *C12N 2710/10343* (2013.01); *C12N 2750/14122* (2013.01); *C12N 2750/14143* (2013.01); *C12N 2840/102* (2013.01); *C12N 2840/60* (2013.01); *C12Y 301/00* (2013.01)

(58) Field of Classification Search
None
See application file for complete search history.

(56) References Cited

U.S. PATENT DOCUMENTS 10,214,730 B2 *  2/2019  Bahou .................... C12N 15/86

OTHER PUBLICATIONS

Sitaraman, et al. (Aug. 23, 2011) "Computationally designed adeno-associated virus (AAV) Rep 78 is efficiently maintained within an adenovirus vector", Proceedings of the National Academy of Sciences, USA., 108(34): 14294-99. (Year: 2011).*

* cited by examiner

*Primary Examiner* — Robert M Kelly
(74) *Attorney, Agent, or Firm* — Medlen & Carroll, LLP

(57) ABSTRACT

The invention provides adeno-associated virus (AAV) replication (Rep) sequences. In one embodiment, the invention provides nucleotide sequences encoding a chimeric protein, wherein the encoded chimeric protein contains a wild type AAV Rep inhibitory amino acid sequence, and wherein the nucleotide sequences contain a scrambled and/or deoptimized polynucleotide sequence encoding the wild type AAV Rep inhibitory amino acid sequence. The invention provides vectors, cells, and viruses containing the invention's sequences. Also provided are methods for detecting portions of the AAV Rep inhibitory amino acid sequence, which reduce replication and/or infection and/or productive infection by viruses. The invention's compositions and methods are useful for site-specific integration and/or expression of heterologous sequences by recombinant adeno-associated virus (rAAV) vectors and by rAAV virus particles, such as hybrid viruses (e.g., Ad-AAV) comprising such vectors. The invention's compositions and methods find application in, for example, gene therapy and/or vaccines.

1 Claim, 28 Drawing Sheets
Specification includes a Sequence Listing.

a)
| Rep78 coding ORF | Codon pair bias score |
|---|---|
| Wild-type | -0.043 |
| Scrambled | -0.117 |
| Deoptimized | -0.443 |
b)
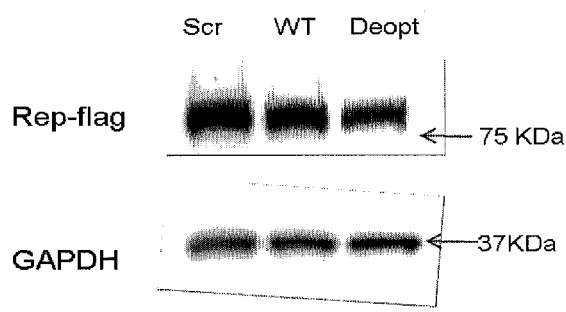
c)
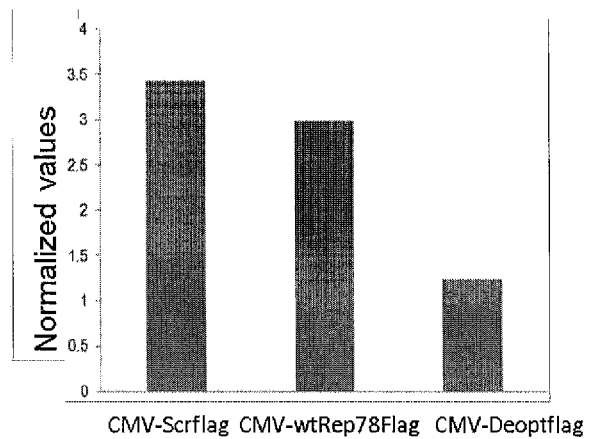
FIGURE 1

Figure 2
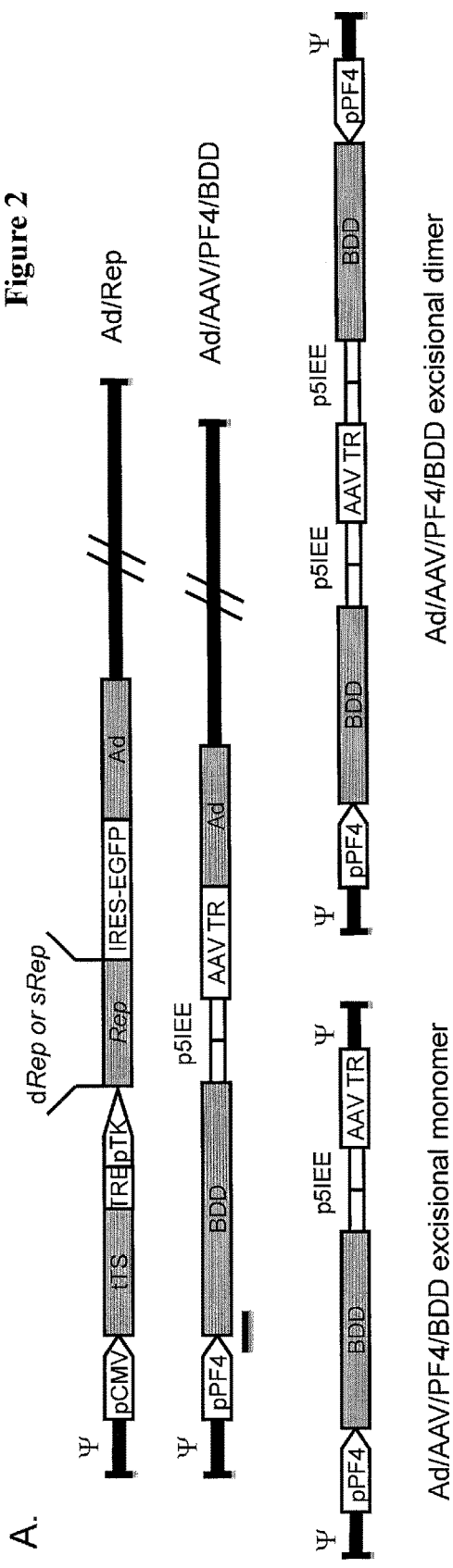
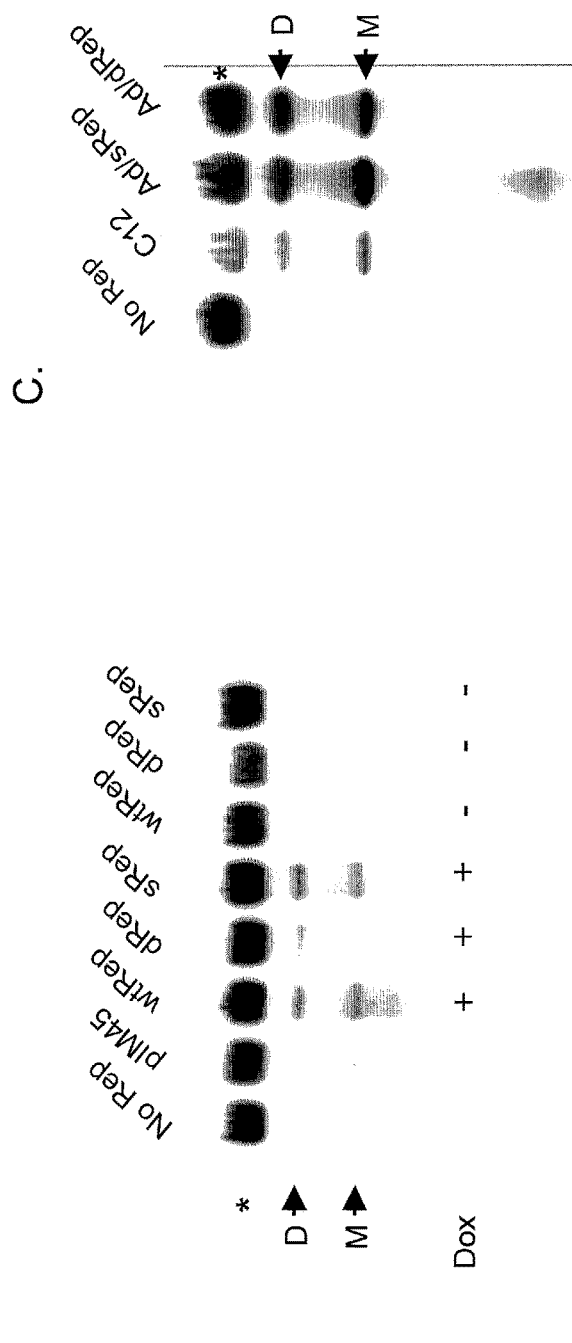

A.
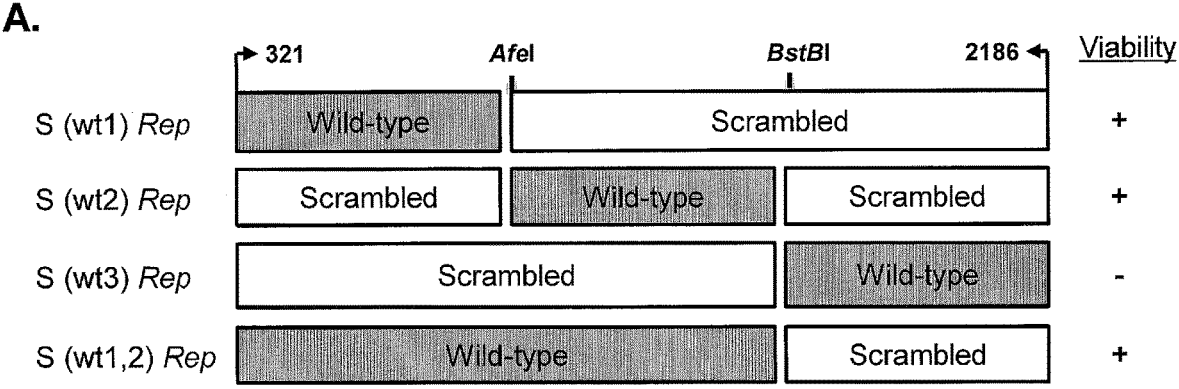
B.
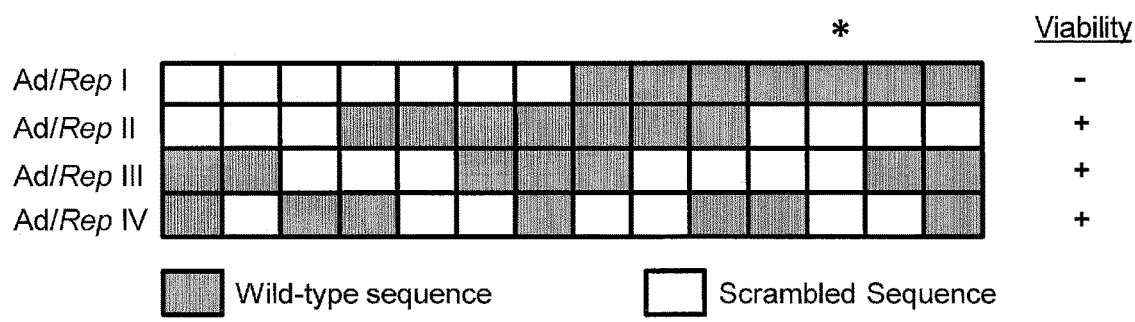
C.
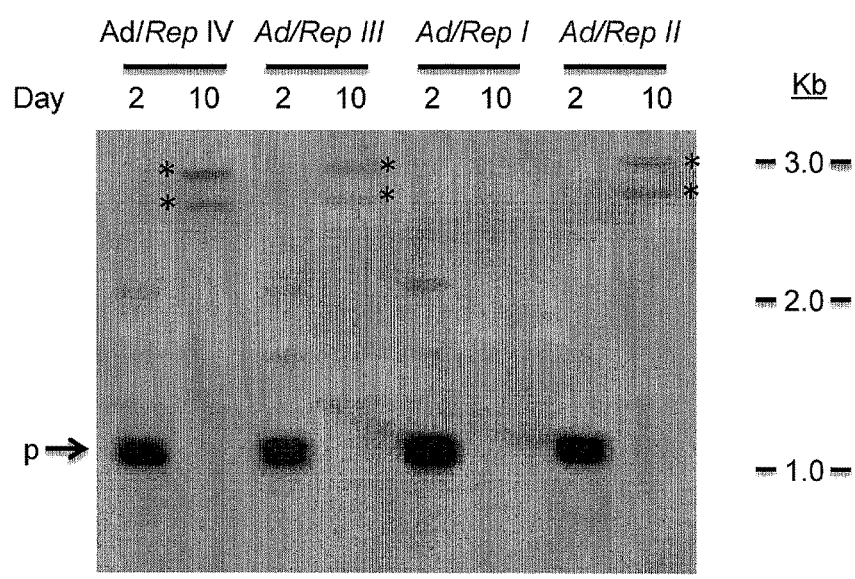
Figure 3

FIGURE 4A    Wild type AAV Rep inhibitory nucleotide sequence (SEQ ID NO:01), 135-bp, from AAV2 genome (GenBank accession number AF043303.1) bp 1782 to bp 1916

```
AAGGGTGGAGCCAAGAAAAGACCCGCCCCAGTGACGCAGATATAAGTGAGCCCAAACG
GGTGCGCGAGTCAGTTGCGCAGCCATCGACGTCAGACGCGGAAGCTTCGATCAACTACG
CAGACAGGTACCAAAAC
```
(SEQ ID NO:01)

FIGURE 4B    Wild type AAV Rep inhibitory polypeptide sequence (SEQ ID NO:02) encoded by SEQ ID NO:01

```
KGGAKKRPAPSDADISEPKRVRESVAQPSTSDAEASINYADRYQN
```
(SEQ ID NO:02)

FIGURE 4C    Scrambled AAV Rep inhibitory nucleotide sequence (SEQ ID NO:07), which corresponds to the 135-bp wild type AAV Rep inhibitory nucleotide sequence (SEQ ID NO:01):

```
AAGGGGGGGGCCAAAAAGCGCCTGCACCTTCCGACGCCGACATTTCCGAGCCAAAGAG
AGTGCGTGAGAGTGTGGCCCAACCCTCCACCAGTGATGCCGAGGCCTCCATTAATTATG
CCGACCGCTATCAGAAT
```
(SEQ ID NO:07)

FIGURE 4D    Deoptimized AAV Rep inhibitory nucleotide sequence (SEQ ID NO:09), which corresponds to the 135-bp wild type AAV Rep inhibitory nucleotide sequence (SEQ ID NO:01):

```
AAGGGCGGAGCGAAAAAGAGACCCGCCCCTAGCGACGCCGACATTAGCGAACCGAAACG
CGTACGCGAATCCGTTGCGCAACCGTCAACCTCCGACGCCGAAGCGTCAATCAATTACG
CCGATAGGTACCAGAAT
```
(SEQ ID NO:09)

FIGURE 4E    Wild type AAV Rep inhibitory nucleotide sequence SEQ ID NO:17 (564-bp sequence from bp 1623 to bp 2186, of Adeno-Associated Virus 2 (AAV2) genome GenBank: AF043303.1. The 135-bp wild type AAV Rep inhibitory nucleotide sequence (SEQ ID NO:01) is underlined

```
TTCGAACACCAGCAGCCGTTGCAAGACCGGATGTTCAAATTTGAACTCACCCGCCGT
CTGGATCATGACTTTGGGAAGGTCACCAAGCAGGAAGTCAAAGACTTTTTCCGGTGGGCA
AAGGATCACGTGGTTGAGGTGGAGCATGAATTCTACGTCAAAAAGGGTGGAGCCAAGAAA
AGACCCGCCCCAGTGACGCAGATATAAGTGAGCCCAAACGGGTGCGCGAGTCAGTTGCG
CAGCCATCGACGTCAGACGCGGAAGCTTCGATCAACTACGCAGACAGGTACCAAAACAAA
TGTTCTCGTCACGTGGGCATGAATCTGATGCTGTTTCCTGCAGACAATGCGAGAGAATG
AATCAGAATTCAAATATCTGCTTCACTCACGGACAGAAAGACTGTTTAGAGTGCTTTCCC
GTGTCAGAATCTCAACCCGTTTCTGTCGTCAAAAAGGCGTATCAGAAACTGTGCTACATT
CATCATATCATGGGAAAGGTGCCAGACGCTTGCACTGCCTGCGATCTGGTCAATGTGGAT
TTGGATGACTGCATCTTTGAACAATAA
```

FIGURE 4F Wild type AAV Rep inhibitory polypeptide sequence (SEQ ID NO:20) encoded by SEQ ID NO: 17

F E H Q Q P L Q D R Met F K F E L T R R L D H D F G K V T K Q E V K D
F F R W A K D H V V E V E H E F Y V K K G G A K K R P A P S D A D I S
E P K R V R E S V A Q P S T S D A E A S I N Y A D R Y Q N K C S R H V G
Met N L Met L F P C R Q C E R Met N Q N S N I C F T H G Q K D C L E C
F P V S E S Q P V S V V K K A Y Q K L C Y I H H I Met G K V P D A C T A
C D L V N V D L D D C I F E Q Stop

FIGURE 4G Scrambled AAV Rep inhibitory nucleotide sequence (SEQ ID NO:18), which corresponds to the 564-bp wild type AAV Rep inhibitory nucleotide sequence SEQ ID NO:17

```
ACTTTCGAACATCAGCAACCCCTCCAGGATCGTATGTTTAAGTTCGAGTTGACTCGGCGG
CTGGACCACGATTTCGGCAAAGTGACGAAACAGGAGGTGAAGGACTTCTTTAGATGGGCC
AAGGACCACGTGGTGGAGGTCGAGCACGAGTTTTATGTGAAGAAGGGGGGGGCCAAAAAG
CGCCCTGCACCTTCCGACGCCGACATTTCCGAGCCAAAGAGAGTGCGTGAGAGTGTGGCC
CAACCCTCCACCAGTGATGCCGAGGCCTCCATTAATTATGCCGACCGCTATCAGAATAAG
TGCTCAAGGCATGTCGGGATGAACCTGATGCTGTTCCCATGCCGCCAGTGCGAGCGCATG
AACCAGAACAGCAACATTTGTTTTACCCACGGGCAGAAGGATTGCCTGGAATGCTTCCCG
GTCAGCGAGTCACAGCCGGTGTCCGTGGTGAAGAAAGCCTACCAAAAGCTGTGTTACATC
CACCACATTATGGGGAAAGTCCCCGATGCCTGTACCGCATGCGACCTGGTGAACGTTGAC
CTCGACGACTGCATTTTCGAGCAGTAA
```

FIGURE 4H Deoptimized AAV Rep inhibitory nucleotide sequence (SEQ ID NO:19), which corresponds to the 564-bp wild type AAV Rep inhibitory nucleotide sequence SEQ ID NO:17

```
ACGTTCGAACACCAGCAGCCATTGCAGGACCGTATGTTCAAATTTGAACTGACTAGGAGA
CTCGACCACGACTTCGGAAAGGTGACTAAGCAGGAGGTGAAAGACTTTTTTCGGTGGGCG
AAAGACCATGTGGTCGAGGTCGAGCACGAGTTTTACGTGAAAAAGGGCGGAGCGAAAAAG
AGACCCGCCCCTAGCGACGCCGACATTAGCGAACCGAAACGCGTACGCGAATCCGTTGCG
CAACCGTCAACCTCCGACGCCGAAGCGTCAATCAATTACGCCGATAGGTACCAGAATAAG
TGCTCTAGACACGTGGGGATGAATCTGATGCTGTTTCCCTGTAGACAGTGCGAGCGTATG
AACCAGAACTCGAACATTTGCTTTACCCACGGACAGAAAGACTGTCTCGAATGCTTTCCC
GTGTCCGAATCGCAACCCGTTAGCGTGGTGAAAAAAGCGTACCAGAAACTGTGTTACATA
CACCATATTATGGGCAAAGTGCCCGACGCATGCACCGCATGCGATCTGGTGAACGTCGAC
CTCGACGATTGCATTTTTGAACAGTAA
```

Nucleotide sequence (SEQ ID NO:03) encoding an exemplary wild type AAV Rep78.

```
ATGCCGGGGTTTTACGAGATTGTGATTAAGGTCCCCAGCGACCTTGACGaGCATCTGCC
CGGCATTTCTGACAGCTTTGTGAACTGGGTGGCCGAGAAGGAATGGGAGTTGCCGCCAG
ATTCTGACATGGATCTGAATCTGATTGAGCAGGCACCCCTGACCGTGGCCGAGAAGCTG
CAGCGCGACTTTCTGACGGAATGGCGCCGTGTGAGTAAGGCCCCGGAGGCCCTTTTCTT
TGTGCAATTTGAGAAGGGAGAGAGcTACTTCCACATGCACGTGCTCGTGGAAACCACCG
GGGTGAAATCCATGGTTTTGGGACGTTTCCTGAGTCAGATTCGCGAAAAACTGATTCAG
AGAATTTACCGCGGGATCGAGCCGACTTTGCCAAACTGGTTCGCGGTCACAAAGACCAG
AAATGGCGCCGGAGGCGGGAACAAGGTGGTGGATGAGTGCTACATCCCCAATTACTTGC
TCCCCAAAACCCAGCCTGAGCTCCAGTGGGCGTGGACTAATATGGAACAGTATTTAAGC
GCCTGTTTGAATCTCACGGAGCGTAAACGGTTGGTGGCGCAGCATCTGACGCACGTGTC
GCAGACGCAGGAGCAGAACAAAGAGAATCAGAATCCCAATTCTGATGCGCCGGTGATCA
GATCAAAAACTTCAGCCAGGTACATGGAGCTGGTCGGGTGGCTCGTGGACAAGGGGATT
ACCTCGGAGAAGCAGTGGATCCAGGAGGACCAGGCCTCATACATCTCCTTCAATGCGGC
CTCCAACTCGCGGTCCCAAATCAAGGCTGCCTTGGACAATGCGGGAAAGATTATGAGCC
TGACTAAAACCGCCCCGACTACCTGGTGGGCCAGCAGCCCGTGGAGGACATTTCCAGC
AATCGGATTTATAAATTTTGGAACTAAACGGGTACGATCCCAATATGCGGCTTCCGT
CTTTCTGGGATGGGCCACGAAAAAGTTCGGCAAGAGGAACACCATCTGGCTGTTTGGGC
CTGCAACTACCGGGAAGACCAACATCGCGGAGGCCATAGCCCACACTGTGCCCTTCTAC
GGGTGCGTAAACTGGACCAATGAGAACTTTCCCTTCAACGACTGTGTCGACAAGATGGT
GATCTGGTGGAGGAGGGGAAGATGACCGCCAAGGTCGTGGAGTCGGCCAAAGCCATTC
TCGGAGGAAGCAAGGTGCGCGTGGACCAGAAATGCAAGTCCTCGGCCCAGATAGACCCG
ACTCCCGTGATCGTCACCTCCAACACCAACATGTGCGCCGTGATTGACGGGAACTCAAC
GACCTTCGAACACCAGCAGCCGTTGCAAACCGGATGTTCAAATTTGAACTCACCCGCCG
TCTGGATCATGACTTTGGGAAGGTCACCAAGCAGGAAGTCAAAGACTTTTTCCGGTGGG
CAAAGGATCACGTGGTTGAGGTGGAGCATGAATTCTACGTCAAA
AAGGGTGGAGCCAAGAAAAGACCCGCCCCCAGTGACGCAGATATAAGTGAGCCCAAACG
GGTGCGCGAGTCAGTTGCGCAGCCATCGACGTCAGACGCGGAAGCTTCGATCAACTACG
CAGACAGGTACCAAAAC
AAATGTTCTCGTCACGTGGGCATGAATCTGATGCTGTTTCCCTGCAGACAATGCGAGAG
AATGAATCAGAATTCAAATATCTGCTTCACTCACGGACAGAAAGACTGTTTAGAGTGCT
TTCCCGTGTCAGAATCTCAACCCGTTTCTGTCGTCAAAAAGGCGTATCAGAAACTGTGC
TACATTCATCATATCATGGGAAAGGTGCCAGACGCTTGCACTGCCTGCGATCTGGTCAA
TGTGGATTTGGATGACTGCATCTTTGAACAATAA
```

FIGURE 5

FIGURE 6A. Amino acid sequence (SEQ ID NO:04) of AAV wild type Rep78 protein (GenBank protein_id="AAC03775.1, db_xref="GI:2906018

```
MPGFYEIVIKVPSDLDEHLPGISDSFVNWVAEKEWELPPDSDMDLNLIEQAPLTVAEKLQRDFLT
EWRRVSKAPEALFFVQFEKGESYFHMHVLVETTGVKSMVLGRFLSQIREKLIQRIYRGIEPTLPN
WFAVTKTRNGAGGGNKVVDECYIPNYLLPKTQPELQWAWTNMEQYLSACLNLTERKRLVAQHLTH
VSQTQEQNKENQNPNSDAPVIRSKTSARYMELVGWLVDKGITSEKQWIQEDQASYISFNAASNSR
SQIKAALDNAGKIMSLTKTAPDYLVGQQPVEDISSNRIYKILELNGYDPQYAASVFLGWATKKFG
KRNTIWLFGPATTGKTNIAEAIAHTVPFYGCVNWTNENFPFNDCVDKMVIWWEEGKMTAKVVESA
KAILGGSKVRVDQKCKSSAQIDPTPVIVTSNTNMCAVIDGNSTTFEHQQPLQDRMFKFELTRRLD
HDFGKVTKQEVKDFFRWAKDHVVEVEHEFYVKKGGAKKRPAPSDADISEPKRVRESVAQPSTSDA
EASINYADRYQNKCSRHVGMNLMLFPCRQCERMNQNSNICFTHGQKDCLECFPVSESQPVSVVKK
AYQKLCYIHHIMGKVPDACTACDLVNVDLDDCIFEQ
```

FIGURE 6B. Amino acid sequence (SEQ ID NO:05) of AAV wild type Rep68 protein (GenBank protein_id="AAC03774.1, db_xref="GI:2906017

```
MPGFYEIVIKVPSDLDEHLPGISDSFVNWVAEKEWELPPDSDMDLNLIEQAPLTVAEKLQRDFLT
EWRRVSKAPEALFFVQFEKGESYFHMHVLVETTGVKSMVLGRFLSQIREKLIQRIYRGIEPTLPN
WFAVTKTRNGAGGGNKVVDECYIPNYLLPKTQPELQWAWTNMEQYLSACLNLTERKRLVAQHLTH
VSQTQEQNKENQNPNSDAPVIRSKTSARYMELVGWLVDKGITSEKQWIQEDQASYISFNAASNSR
SQIKAALDNAGKIMSLTKTAPDYLVGQQPVEDISSNRIYKILELNGYDPQYAASVFLGWATKKFG
KRNTIWLFGPATTGKTNIAEAIAHTVPFYGCVNWTNENFPFNDCVDKMVIWWEEGKMTAKVVESA
KAILGGSKVRVDQKCKSSAQIDPTPVIVTSNTNMCAVIDGNSTTFEHQQPLQDRMFKFELTRRLD
HDFGKVTKQEVKDFFRWAKDHVVEVEHEFYVKKGGAKKRPAPSDADISEPKRVRESVAQPSTSDA
EASINYADRLARGHSL
```

FIGURE 7A Scrambled AAV Rep78 nucleotide sequence sRep78 (SEQ ID NO:06). Sequence of the exemplary scrambled AAV Rep inhibitory nucleotide sequence (SEQ ID NO:07), which corresponds to the 135-bp wild type AAV Rep inhibitory nucleotide sequence (SEQ ID NO:01) is in italics:

ATGCCCGGATTCTACGAAATCGTCATCAAAGTGCCCTCTGACTTGGATGAACACCTGCCGGGGA
TCAGCGATTCTTTCGTCAATGGGTCGCGGAGAAAGAGTGGGAACTTCCCCCGACTCGGACAT
GGACCTGAACTTAATCGAGCAAGCCCCGCTGACGGTGGCGGAGAAACTGCAGCGGGACTTTCTG
ACCGAGTGGAGGCGCGTATCGAAAGCGCCCGAAGCTTTGTTTTCGTCCAGTTCGAGAAGGGGG
AGTCGTACTTTCATATGCATGTGTTGGTGGAGACTACGGGAGTGAAGAGTATGGTGCTAGGGAG
GTTTCTGTCGCAAATAAGAGAGAAGCTGATCCAGCGGATATACCGTGGCATTGAGCCCACCCTT
CCCAATTGGTTTGCCGTGACCAAAACTCGTAACGGAGCAGGGGGGGAAATAAAGTCGTCGACG
AGTGCTATATTCCGAACTACCTCTTGCCCAAGACGCAGCCCGAATTGCAGTGGGCCTGGACCAA
CATGGAGCAATACCTGTCAGCGTGCCTCAACTTGACCGAAAGAAAGAGACTCGTGGCCCAGCAC
CTGACCCATGTCTCACAGACCCAGGAACAGAATAAGGAAAACCAAAACCCAAATAGCGACGCCC
CCGTGATACGGAGCAAGACCAGCGCTCGCTACATGGAGTTAGTGGGATGGTTGGTGGATAAAGG
AATCACGTCTGAGAAACAATGGATTCAGGAGGACCAGGCGTCCTACATTAGTTTTAACGCCGCG
TCAAATAGCAGATCTCAGATTAAAGCCGCGCTCGATAACGCCGGCAAAATCATGTCGCTGACCA
AGACAGCTCCCGACTACCTGGTGGGACAGCAGCCGGTGGAGGACATCTCTTCTAACCGTATCTA
CAAGATCCTtGAGTTGAATGGCTACGACCCACAGTACGCCGCCTCAGTGTTTCTGGGCTGGGCA
ACCAAGAAATTTGGGAAACGCAATACGATTTGGCTGTTCGGACCCGCCACCACTGGTAAGACTA
ATATTGCCGAGGCGATCGCACATACCGTTCCGTTTTACGGATGCGTGAATTGGACTAACGAAAA
TTTCCCCTTTAATGATTGCGTGGACAAGATGGTTATTTGGTGGGAGGAAGGAAAGATGACTGCG
AAAGTGGTGGAATCCGCTAAGGCTATCTTGGGGGGGTCGAAAGTTCGGGTCGACCAGAAGTGCA
AATCGTCCGCGCAGATTGACCCCACCCCGTGATTGTGACGTCAAATACTAATATGTGTGCGGT
CATCGATGGCAATAGCACCACTTTCGAACATCAGCAACCCCTCCAGGATCGTATGTTTAAGTTC
GAGTTGACTCGGCGGCTGGACCACGATTTCGGCAAAGTGACGAAACAGGAGGTGAAGGACTTCT
TTAGATGGGCCAAGGACCACGTGGTGGAGGTCGAGCACGAGTTTTATGTGAAG
*AAGGGGGGGCCAAAAAGCGCCCTGCACCTTCCGACGCCGACATTTCCGAGCCAAAGAGAGTGC*
*GTGAGAGTGTGGCCCAACCCTCCACCAGTGATGCCGAGGCCTCCATTAATTATGCCGACCGCTA*
*TCAGAAT*
AAGTGCTCAAGGCATGTCGGGATGAACCTGATGCTGTTCCCATGCCGCCAGTGCGAGCGCATGA
ACCAGAACAGCAACATTTGTTTTACCCACGGGCAGAAGGATTGCCTGGAATGCTTCCCGGTCAG
CGAGTCACAGCCGGTGTCCGTGGTGAAGAAAGCCTACCAAAAGCTGTGTTACATCCACCACATT
ATGGGGAAAGTCCCCGATGCCTGTACCGCATGCGACCTGGTGAACGTTGACCTCGACGACTGCA
TTTTCGAGCAGTAA

FIGURE 7B | Deoptimized AAV Rep78 nucleotide sequence dRep78 (SEQ ID NO:08). Sequence of the exemplary deoptimized AAV Rep inhibitory nucleotide sequence (SEQ ID NO:09), which corresponds to the 135-bp wild type AAV Rep inhibitory nucleotide sequence (SEQ ID NO:01) is in italics:

```
ATGCCCGGGTTTTACGAGATCGTGATTAAGGTGCCATCCGATCTCGACGAGCATCTGCCCGGGA
TTAGCGATTCGTTCGTGAATTGGGTCGCCGAAAAGGAGTGGGAGTTGCCCCCGATAGCGATAT
GGACCTGAATCTGATCGAGCAGGCCCCCCTTACCGTCGCCGAGAAACTGCAACGCGATTTCTTG
ACCGAGTGGAGACGCGTGAGTAAGGCCCCCGAAGCCCTGTTTTTCGTGCAATTTGAAAAGGGCG
AGTCATACTTTCATATGCACGTGTTGGTCGAGACTACCGGCGTTAAGTCTATGGTGCTCGGACG
GTTTCTGTCACAGATACGCGAAAAACTGATCCAGCGTATCTATCGCGGAATCGAGCCAACCCTA
CCGAATTGGTTCGCCGTTACGAAGACCCGTAACGGCGCCGGGGGGGGAATAAGGTGGTCGACG
AGTGCTATATCCCTAACTATCTGTTACCGAAAACGCAACCCGAGTTGCAGTGGGCCTGGACTAA
CATGGAGCAATACTTGTCCGCATGCCTGAATCTGACCGAACGCAAACGGTTGGTCGCCCAGCAT
CTGACACACGTGAGTCAGACCCAGGAGCAGAATAAGGAGAATCAGAATCCGAACTCCGACGCCC
CCGTGATACGGTCTAAGACTAGCGCTAGGTATATGGAGTTGGTGGGTGGTTGGTCGACAAGGG
GATTACCTCCGAGAAACAGTGGATCCAGGAGGACCAGGCGTCATACATTTCGTTAACGCCGCA
TCGAACTCACGGTCACAGATTAAGGCCGCACTCGACAACGCCGGTAAGATTATGAGTCTGACTA
AGACCGCCCCGATTACTTAGTGGGACAGCAACCCGTCGAGGACATTTCGAGTAATCGGATTTA
CAAAATCCTCGAaCTTAACGGATACGACCCCAATACGCCGCTAGCGTGTTTCTGGGGTGGGCG
ACTAAGAAATTCGGAAAGCGTAATACGATTTGGTTGTTCGGACCCGCTACGACCGGCAAAACGA
ATATCGCCGAAGCGATCGCGCATACCGTGCCATTCTACGGGTGCGTGAATTGGACGAACGAGAA
CTTTCCGTTTAACGATTGCGTCGACAAGATGGTGATTTGGTGGGAGGAGGGAAAGATGACCGCT
AAGGTGGTCGAGTCCGCGAAAGCGATTCTGGGGGGGTCTAAGGTGAGAGTCGACCAGAAGTGTA
AGTCTTCgGCTCAGATCGATCCGACCCCGTGATCGTGACCTCTAACACTAACATGTGCGCCGT
GATCGACGGGAATTCGACTACGTTCGAACACCAGCAGCCATTGCAGGACCGTATGTTCAAATTT
GAACTGACTAGGAGACTCGACCACGACTTCGGAAAGGTGACTAAGCAGGAGGTGAAAGACTTTT
TTCGGTGGGCGAAAGACCATGTGGTCGAGGTCGAGCACGAGTTTACGTGAAA
AAGGGCGGAGCGAAAAGAGACCCGCCCCTAGCGACGCCGACATTAGCGAACCGAAACGCGTAC
GCGAATCCGTTGCGCAACCGTCAACCTCCGACGCCGAAGCGTCAATCAATTACGCCGATAGGTA
CCAGAAT
AAGTGCTCTAGACACGTGGGGATGAATCTGATGCTGTTTCCCTGTAGACAGTGCGAGCGTATGA
ACCAGAACTCGAACATTTGCTTTACCCACGGACAGAAAGACTGTCTCGAaTGCTTTCCCGTGTC
CGAATCGCAACCCGTTAGCGTGGTGAAAAAGCGTACCAGAAACTGTGTTACATACACCATATT
ATGGGCAAAGTGCCCGACGCATGCACCGCATGCGATCTGGTGAACGTCGACCTCGACGATTGCA
TTTTTGAACAGTAA
```

Genome organization of AAV
(Merten-O-W et al. 2005:12:S51-61)

Adenovirus genome (Alba et al. Gene Therapy 2005;12:S18-27)

FIGURE 10A

Schematic representation of the 138-nt IEE (SEQ ID NO:11) showing YY1 and Rep-binding sites, a putative upstream stimulating factor (USF)-binding site, and a TATA box (Philpott et al. (2002) A p5 integration efficiency element mediates Rep-dependent integration into AAVS1 at chromosome 19. *Proc. Natl. Acad. Sci. USA* 99:12381).

Figure 12A

```
   1 ttggccactc cctctctgcg cgctcgctcg ctcactgagg ccgggcgacc aaaggtcgcc
  61 cgacgcccgg gctttgcccg ggcggcctca gtgagcgagc gagcgcgcag agagggagtg
 121 gccaactcca tcactagggg ttcctggagg ggtggagtcg tgacgtgaat tacgtcatag
 181 ggttagggag gtcctgtatt agaggtcacg tgagtgtttt gcgacatttt gcgacaccat
 241 gtggtcacgc tgggtattta agcccgagtg agcacgcagg gtctccattt tgaagcggga
 301 ggtttgaacg cgcagccgcc atgccgggt tttacgagat tgtgattaag gtcccagcg
 361 accttgacga gcatctgccc ggcatttctg acagctttgt gaactgggtg gccgagaagg
 421 aatgggagtt gccgccagat tctgacatgg atctgaatct gattgagcag gcacccctga
 481 ccgtggccga gaagctgcag cgcgactttc tgacggaatg gcgccgtgtg agtaaggccc
 541 cggaggccct tttctttgtg caatttgaga agggagagag ctacttccac atgcacgtgc
 601 tcgtggaaac caccggggtg aaatccatgg ttttgggacg tttcctgagt cagattcgcg
 661 aaaaactgat tcagagaatt taccgcggga tcgagccgac tttgccaaac tggttcgcgg
 721 tcacaaagac cagaaatggc gccggaggcg ggaacaaggt ggtggatgag tgctacatcc
 781 ccaattactt gctccccaaa acccagcctg agctccagtg ggcgtggact aatatggaac
 841 agtatttaag cgcctgtttg aatctcacgg agcgtaaacg gttggtggcg cagcatctga
 901 cgcacgtgtc gcagacgcag gagcagaaca agagaatca gaatcccaat tctgatgcgc
 961 cggtgatcag atcaaaaact tcagccaggt acatggagct ggtcgggtgg ctcgtggaca
1021 aggggattac ctcggagaag cagtggatcc aggaggacca ggcctcatac atctccttca
1081 atgcggcctc caactcgcgg tcccaaatca aggctgcctt ggacaatgcg ggaaagatta
1141 tgagcctgac taaaaccgcc cccgactacc tggtgggcca gcagccgtg gaggacattt
1201 ccagcaatcg gatttataaa attttggaac taaacgggta cgatccccaa tatgcggctt
1261 ccgtctttct gggatgggcc acgaaaaagt tcggcaagag gaacaccatc tggctgtttg
1321 ggcctgcaac taccgggaag accaacatcg cggaggccat agcccacact gtgcccttct
1381 acgggtgcgt aaactggacc aatgagaact ttcccttcaa cgactgtgtc gacaagatgg
1441 tgatctggtg ggaggagggg aagatgaccg ccaaggtcgt ggagtcggcc aaagccattc
1501 tcggaggaag caaggtgcgc gtggaccaga atgcaagtc ctcggcccag atagacccga
1561 ctcccgtgat cgtcacctcc aacaccaaca tgtgcgccgt gattgacggg aactcaacga
1621 ccttcgaaca ccagcagccg ttgcaagacc ggatgttcaa atttgaactc acccgccgtc
1681 tggatcatga ctttgggaag gtcaccaagc aggaagtcaa agactttttc cggtgggcaa
1741 aggatcacgt ggttgaggtg gagcatgaat tctacgtcaa aagggtgga gccaagaaaa
1801 gacccgccc cagtgacgca gatataagtg agccaaacg gtgcgcgag tcagttgcgc
1861 agccatcgac gtcagacgcg gaagcttcga tcaactacgc agacaggtac caaaacaaat
1921 gttctcgtca cgtgggcatg aatctgatgc tgtttccctg cagacaatgc gagagaatga
1981 atcagaattc aaatatctgc ttcactcacg gacagaaaga ctgtttagag tgctttcccg
2041 tgtcagaatc tcaacccgtt tctgtcgtca aaaaggcgta tcagaaactg tgctacattc
2101 atcatatcat gggaaaggtg ccagacgctt gcactgcctg cgatctggtc aatgtggatt
2161 tggatgactg catctttgaa caataaatga tttaaatcag gtatggctgc cgatggttat
```

Figure 12B

```
2221 cttccagatt ggctcgagga cactctctct gaaggaataa gacagtggtg gaagctcaaa
2281 cctggcccac caccaccaaa gcccgcagag cggcataagg acgacagcag gggtcttgtg
2341 cttcctgggt acaagtacct cggacccttc aacggactcg acaagggaga gccggtcaac
2401 gaggcagacg ccgcggccct cgagcacgac aaagcctacg accggcagct cgacagcgga
2461 gacaacccgt acctcaagta caaccacgcc gacgcggagt tcaggagcg ccttaaagaa
2521 gatacgtctt tgggggcaa cctcggacga gcagtcttcc aggcgaaaaa gagggttctt
2581 gaacctctgg gcctggttga ggaacctgtt aagacggctc cgggaaaaaa gaggccggta
2641 gagcactctc ctgtggagcc agactcctcc tcgggaaccg gaaaggcggg ccagcagcct
2701 gcaagaaaaa gattgaattt tggtcagact ggagacgcag actcagtacc tgaccccag
2761 cctctcggac agccaccagc agccccctct ggtctgggaa ctaatacgat ggctacaggc
2821 agtggcgcac caatggcaga caataacgag ggcgccgacg gagtgggtaa ttcctcggga
2881 aattggcatt gcgattccac atggatgggc gacagagtca tcaccaccag cacccgaacc
2941 tgggccctgc ccacctacaa caaccacctc tacaaacaaa tttccagcca atcaggagcc
3001 tcgaacgaca atcactactt tggctacagc accccttggg ggtattttga cttcaacaga
3061 ttccactgcc acttttcacc acgtgactgg caaagactca tcaacaacaa ctggggattc
3121 cgacccaaga gactcaactt caagctcttt aacattcaag tcaaagaggt cacgcagaat
3181 gacggtacga cgacgattgc caataacctt accagcacgg ttcaggtgtt tactgactcg
3241 gagtaccagc tcccgtacgt cctcggctcg gcgcatcaag gatgcctccc gccgttccca
3301 gcagacgtct tcatggtgcc acagtatgga tacctcaccc tgaacaacgg gagtcaggca
3361 gtaggacgct cttcatttta ctgcctggag tactttcctt ctcagatgct gcgtaccgga
3421 aacaacttta ccttcagcta cacttttgag gacgttcctt tccacagcag ctacgctcac
3481 agccagagtc tggaccgtct catgaatcct ctcatcgacc agtacctgta ttacttgagc
3541 agaacaaaca ctccaagtgg aaccaccacg cagtcaaggc ttcagttttc tcaggccgga
3601 gcgagtgaca ttcgggacca gtctaggaac tggcttcctg gaccctgtta ccgccagcag
3661 cgagtatcaa agacatctgc ggataacaac aacagtgaat actcgtggac tggagctacc
3721 aagtaccacc tcaatggcag agactctctg gtgaatccgg gcccggccat ggcaagccac
3781 aaggacgatg aagaaaagtt ttttcctcag agcggggttc tcatctttgg gaagcaaggc
3841 tcagagaaaa caaatgtgga cattgaaaag gtcatgatta cagacgaaga ggaaatcagg
3901 acaaccaatc ccgtggctac ggagcagtat ggttctgtat ctaccaacct ccagagaggc
3961 aacagacaag cagctaccgc agatgtcaac acacaaggcg ttcttccagg catggtctgg
4021 caggacagag atgtgtacct tcaggggccc atctgggcaa agattccaca cacggacgga
4081 cattttcacc cctctcccct catgggtgga ttcggactta acaccctcc tccacagatt
4141 ctcatcaaga acacccggt acctgcgaat ccttcgacca ccttcagtgc ggcaaagttt
4201 gcttccttca tcacacagta ctccacggga caggtcagcg tggagatcga gtgggagctg
4261 cagaaggaaa acagcaaacg ctggaatccc gaaattcagt acacttccaa ctacaacaag
4321 tctgttaatg tggactttac tgtggacact aatggcgtgt attcagagcc tcgccccatt
```

Figure 12C

```
4381 ggcaccagat acctgactcg taatctgtaa ttgcttgtta atcaataaac cgtttaattc
4441 gtttcagttg aactttggtc tctgcgtatt tctttcttat ctagtttcca tggctacgta
4501 gataagtagc atggcgggtt aatcattaac tacaaggaac ccctagtgat ggagttggcc
4561 actccctctc tgcgcgctcg ctcgctcact gaggccgggc gaccaaaggt cgcccgacgc
4621 ccgggctttg cccgggcggc ctcagtgagc gagcgagcgc gcagagaggg agtggccaa
//
```

Figure 13A

```
                                       •321
WTREP         GGTTTGAACGCGCAGCCGCCATGCCGGGGTTTTACGAGATTGTGATTAAGGTCCCCAGCG 360
dREP          --------------------ATGCCCGGGTTTTACGAGATCGTGATTAAGGTGCCATCCG
sREP          --------------------ATGCCCGGATTCTACGAAATCGTCATCAAAGTGCCCTCTG
                                  ***** ** ** ***** ** ** ** ** ** **    *

WTREP         ACCTTGACGAGCATCTGCCCGGCATTTCTGACAGCTTTGTGAACTGGGTGGCCGAGAAGG 420
dREP          ATCTCGACGAGCATCTGCCCGGGATTAGCGATTCGTTCGTGAATTGGGTCGCCGAAAAGG
sREP          ACTTGGATGAACACCTGCCGGGGATCAGCGATTCTTTCGTCAATTGGGTCGCGGAGAAAG
              *  * ** ** ** ***** ** **    **    ** ** ** ***** ** ** ** *

WTREP         AATGGGAGTTGCCGCCAGATTCTGACATGGATCTGAATCTGATTGAGCAGGCACCCCTGA 480
dREP          AGTGGGAGTTGCCCCCCGATAGCGATATGGACCTGAATCTGATCGAGCAGGCCCCCCTTA
sREP          AGTGGGAACTTCCCCCCGACTCGGACATGGACCTGAACTTAATCGAGCAAGCCCCGCTGA
              * *****    * ** ** **    ** ***** *****   * ** ***** ** ** *

WTREP         CCGTGGCCGAGAAGCTGCAGCGCGACTTTCTGACGGAATGGCGCCGTGTGAGTAAGGCCC 540
dREP          CCGTCGCCGAGAAACTGCAACGCGATTTCTTGACCGAGTGGAGACGCGTGAGTAAGGCCC
sREP          CGGTGGCGGAGAAACTGCAGCGGGACTTTCTGACCGAGTGGAGGCGCGTATCGAAAGCGC
              * ** ** ***** ***** ** ** **  ** ** *** ** ***         ** ** *

WTREP         CGGAGGCCCTTTTCTTTGTGCAATTTGAGAAGGGAGAGAGCTACTTCCACATGCACGTGC 600
dREP          CCGAAGCCCTGTTTTTCGTGCAATTTGAAAAGGGCGAGTCATACTTTCATATGCACGTGT
sREP          CCGAAGCTTTGTTTTTCGTCCAGTTCGAGAAGGGGGAGTCGTACTTTCATATGCATGTGT
              * ** **    * ** ** ** ** ** ** ***** ***       ***** ** ***** ***

WTREP         TCGTGGAAACCACCGGGGTGAAATCCATGGTTTTGGGACGTTTCCTGAGTCAGATTCGCG 660
dREP          TGGTCGAGACTACCGGCGTTAAGTCTATGGTGCTCGGACGGTTTCTGTCACAGATACGCG
sREP          TGGTGGAGACTACGGGAGTGAAGAGTATGGTGCTAGGGAGGTTTCTGTCGCAAATAAGAG
              * ** ** ** ** ** ** **          *****   * **  * ** ***    ** **  * *

WTREP         AAAAACTGATTCAGAGAATTTACCGCGGGATCGAGCCGACTTTGCCAAACTGGTTCGCGG 720
dREP          AAAAACTGATCCAGCGTATCTATCGCGGAATCGAGCCAACCCTACCGAATTGGTTCGCCG
sREP          AGAAGCTGATCCAGCGGATATACCGTGGCATTGAGCCCACCCTTCCCAATTGGTTTGCCG
              *  ** ***** ***  *  ** ** **   ** ** ** **      *  ** ** ***** ** *

WTREP         TCACAAAGACCAGAAATGGCGCCGGAGGCGGGAACAAGGTGGTGGATGAGTGCTACATCC 780
dREP          TTACGAAGACCCGTAACGGCGCCGGGGGGGGGAATAAGGTGGTCGACGAGTGCTATATCC
sREP          TGACCAAAACTCGTAACGGAGCAGGGGGGGGGAAATAAAGTCGTCGACGAGTGCTATATTC
              *  ** ** **    * ** ** ** ** ** ** ** ** ** ** ** ******** ** *

WTREP         CCAATTACTTGCTCCCCAAAACCCAGCCTGAGCTCCAGTGGGCGTGGACTAATATGGAAC 840
dREP          CTAACTATCTGTTACCGAAAACGCAACCCGAGTTGCAGTGGGCCTGGACTAACATGGAGC
sREP          CGAACTACCTCTTGCCCAAGACGCAGCCCGAATTGCAGTGGGCCTGGACCAACATGGAGC
              *  ** **    *     * ** ** ** ** ** **    * ******** ***** ** ***** *

WTREP         AGTATTTAAGCGCCTGTTTGAATCTCACGGAGCGTAAACGGTTGGTGGCGCAGCATCTGA 900
dREP          AATACTTGTCCGCATGCCTGAATCTGACCGAACGCAAACGGTTGGTCGCCCAGCATCTGA
sREP          AATACCTGTCAGCGTGCCTCAACTTGACCGAAAGAAGAGACTCGTGGCCCAGCACCTGA
              * **  *         ** **    **  * **   * ** *  *      *  ** ** ***** ****

WTREP         CGCACGTGTCGCAGACGCAGGAGCAGAACAAAGAGAATCAGAATCCCAATTCTGATGCGC 960
dREP          CACACGTGAGTCAGACCCAGGAGCAGAATAAGGAGAATCAGAATCCGAACTCCGACGCCC
sREP          CCCATGTCTCACAGACCCAGGAACAGAATAAGGAAAACCAAAACCCAAATAGCGACGCCC
              *  ** **     ***** ***** ***** ** ** ** ** ** ** ** **    ** ** *
```

FIGURE 13B

```
WTREP   CGGTGATCAGATCAAAAACTTCAGCCAGGTACATGGAGCTGGTCGGGTGGCTCGTGGACA 1020
dREP    CCGTGATACGGTCTAAGACTAGCGCTAGGTATATGGAGTTGGTGGGGTGGTTGGTCGACA
sREP    CCGTGATACGGAGCAAGACCAGCGCTCGCTACATGGAGTTAGTGGGATGGTTGGTGGATA
        * *****  *    ** **      **  * ** ****** * ** ** *** * ** ** *

WTREP   AGGGGATTACCTCGGAGAAGCAGTGGATCCAGGAGGACCAGGCCTCATACATCTCCTTCA 1080
dREP    AGGGGATTACCTCCGAGAAACAGTGGATCCAGGAGGACCAGGCGTCATACATTTCGTTTA
sREP    AAGGAATCACGTCTGAGAAACAATGGATTCAGGAGGACCAGGCGTCCTACATTAGTTTTA
        * ** ** ** ** *****  ** ***** ************** ** *****    ** *

WTREP   ATGCGGCCTCCAACTCGCGG-TCCCAAATCAAGGCTGCCTTGGACAATGCGGGAAAGATT 1139
dREP    ACGCCGCATCGAACTCACGG-TCACAGATTAAGGCCGCACTCGACAACGCCGGTAAGATT
sREP    ACGCCGCGTCAAA-TAGCAGATCTCAGATTAAAGCCGCGCTCGATAACGCCGGCAAAATC
        * ** ** ** ** *  *  * ** ** ** ** **    *  ** ** ** ** ** **

WTREP   ATGAGCCTGACTAAAACCGCCCCCGACTACCTGGTGGGCCAGCAGCCCGTGGAGGACATT 1199
dREP    ATGAGTCTGACTAAGACCGCCCCCGATTACTTAGTGGGACAGCAACCCGTCGAGGACATT
sREP    ATGTCGCTGACCAAGACAGCTCCCGACTACCTGGTGGGACAGCAGCCGGTGGAGGACATC
        ***      ***** ** **  ***** *** * ***** ***** ** ** ********

WTREP   TCCAGCAATCGGATTTATAAAATTTTGGAACTAAACGGGTACGATCCCCAATATGCGGCT 1259
dREP    TCGAGTAATCGGATTTACAAAATCCTCGAACTTAACGGATACGACCCCCAATACGCCGCT
sREP    TCTTCTAACCGTATCTACAAGATCCTTGAGTTGAATGGCTACGACCCACAGTACGCCGCC
        **    ** **  ** ** **  **  ** **    *  ** ** ****** ** ** **

WTREP   TCCGTCTTTCTGGGATGGGCCACGAAAAAGTTCGGCAAGAGGAACACCATCTGGCTGTTT 1319
dREP    AGCGTGTTTCTGGGGTGGGCGACTAAGAAATTCGGAAAGCGTAATACGATTTGGTTGTTC
sREP    TCAGTGTTTCTGGGCTGGGCAACCAAGAAATTTGGGAAACGCAATACGATTTGGCTGTTC
             ** ******** ** *****  ** ** **  ** ** **    * ** ** ** *** ****

WTREP   GGGCCTGCAACTACCGGGAAGACCAACATCGCGGAGGCCATAGCCCACACTGTGCCCTTC 1379
dREP    GGACCCGCTACGACCGGCAAAACGAATATCGCCGAAGCGATCGCGCATACCGTGCCATTC
sREP    GGACCCGCCACCACTGGTAAGACTAATATTGCCGAGGCGATCGCACATACCGTTCCGTTT

WTREP   TACGGGTGCGTAAACTGGACCAATGAGAACTTTCCCTTCAACGACTGTGTCGACAAGATG 1439
dREP    TACGGGTGCGTGAATTGGACGAACGAGAACTTTCCGTTTAACGATTGCGTCGACAAGATG
sREP    TACGGATGCGTGAATTGGACTAACGAAAATTTCCCCTTTAATGATTGCGTGGACAAGATG
        ***** ***** **  ****** ** **  ** ** ** ** ** ** ** ** ********

WTREP   GTGATCTGGTGGGAGGAGGGGAAGATGACCGCCAAGGTCGTGGAGTCGGCCAAAGCCATT 1499
dREP    GTGATTTGGTGGGAGGAGGGAAAGATGACCGCTAAGGTGGTCGAGTCCGCGAAAGCGATT
sREP    GTTATTTGGTGGGAGGAAGGAAAGATGACTGCGAAAGTGGTGGAATCCGCTAAGGCTATC
        ** ** ********** ** ** ******** **  ** ** ** ** ** ** ** **

WTREP   CTCGGAGGAAGCAAGGTGCGCGTGGACCAGAAATGCAAGTCCTCGGCCCAGATAGACCCG 1559
dREP    CTGGGGGGGTCTAAGGTGAGAGTCGACCAGAAGTGTAAGTCTTCGGCTCAGATCGATCCG
sREP    TTGGGGGGGTCGAAAGTTCGGGTCGACCAGAAGTGCAAATCGTCCGCGCAGATTGACCCC
         * ** **    ** **   * ** ******** ** ** ** ** ** ***** ** **

WTREP   ACTCCCGTGATCGTCACCTCCAACACCAACATGTGCGCCGTGATTGACGGGAACTCAACG 1619
dREP    ACCCCCGTGATCGTGACCTCTAACACTAACATGTGCGCCGTGATCGACGGGAATTCGACT
sREP    ACCCCCGTGATTGTGACGTCAAATACTAATATGTGTGCGGTCATCGATGGCAATAGCACC
        ** ******** ** **  ** ** ** ** ***** ** ** ** ** ** **    **

WTREP   ACCTTCGAACACCAGCAGCCGTTGCAAGACCGGATGTTCAAATTTGAACTCACCCGCCGT 1679
dREP    ACGTTCGAACACCAGCAGCCATTGCAGGACCGTATGTTCAAATTTGAACTGACTAGGAGA
sREP    ACTTTCGAACATCAGCAACCCCTCCAGGATCGTATGTTTAAGTTCGAGTTGACTCGGCGG
        ** ******** ***** **    *  ** ** ***** ** ** ** * ** *   *
```

FIGURE 13C

```
WTREP   CTGGATCATGACTTTGGGAAGGTCACCAAGCAGGAAGTCAAAGACTTTTTCCGGTGGGCA 1739
dREP    CTCGACCACGACTTCGGAAAGGTGACTAAGCAGGAGGTGAAAGACTTTTTTCGGTGGGCG
sREP    CTGGACCACGATTTCGGCAAAGTGACGAAACAGGAGGTGAAGGACTTCTTTAGATGGGCC
        ** ** ** **  ** ** ** ** *****  ** ** ***** **  *  *****

GGT
WTREP   AAGGATCACGTGGTTGAGGTGGAGCATGAATTCTACGTCAAAAAGGGTGGAGCCAAGAAA 1799
dREP    AAAGACCATGTGGTCGAGGTCGAGCACGAGTTTTACGTGAAAAAGGGCGGAGCGAAAAAG
sREP    AAGGACCACGTGGTGGAGGTCGAGCACGAGTTTTATGTGAAGAAGGGGGGGGCCAAAAAG
        ** ** ** *****  ***** ***** **  ** ** ** **  *** **  ** **

SP1         AP1
WTREP   AGACCCGCCCCTCGCTGACGCGGACATTAGCGAACCCAAACGGGTGCGCGAGTCAGTTGCG 1859
dREP    AGACCCGCCCCTAGCGACGCCGACATTAGCGAACCGAAACGCGTACGCGAATCCGTTGCG
sREP    CGCCCTGCACCTTCCGACGCCGACATTTCCGAGCCAAAGAGAGTGCGTGAGAGTGTGGCC
         * ** ** **        ***** ** **    ** ** **   * ** ** **    ** **

WTREP   CAGCCATCGACGTCAGACGCGGAAGCTTCGATCAACTACGCAGACAGGTACCAAAACAAA 1919
dREP    CAACCGTCAACCTCCGACGCCGAAGCGTCAATCAATTACGCCGATAGGTACCAGAATAAG
sREP    CAACCCTCCACCAGTGATGCCGAGGCCTCCATTAATTATGCCGACCGCTATCAGAATAAG
        ** **     ** **    **  ** ** ** ** ** ** ** **  *  ** ** ** **

WTREP   TGTTCTCGTCACGTGGGCATGAATCTGATGCTGTTTCCCTGCAGACAATGCGAGAGAATG 1979
dREP    TGCTCTAGACACGTGGGGATGAATCTGATGCTGTTTCCCTGTAGACAGTGCGAGCGTATG
sREP    TGCTCAAGGCATGTCGGGATGAACCTGATGCTGTTCCCATGCCGCCAGTGCGAGCGCATG
        ** **  * ** ** ** ***** ************  ** **   * ** ****** * ***

WTREP   AATCAGAATTCAAATATCTGCTTCACTCACGGACAGAAAGACTGTTTAGAGTGCTTTCCC 2039
dREP    AACCAGAACTCGAACATTTGCTTTACCCACGGACAGAAAGACTGTCTCGAATGCTTTCCC
sREP    AACCAGAACAGCAACATTTGTTTTACCCACGGGCAGAAGGATTGCCTGGAATGCTTCCCG
        ** *****    ** ** ** **  ** ** ** *****  **  **   *  ** ***** **

WTREP   GTGTCAGAATCTCAACCCGTTTCTGTCGTCAAAAAGGCGTATCAGAAACTGTGCTACATT 2099
dREP    GTGTCCGAATCGCAACCCGTTAGCGTGGTGAAAAAAGCGTACCAGAAACTGTGTTACATA
sREP    GTCAGCGAGTCACAGCCGGTGTCCGTGGTGAAGAAAGCCTACCAAAAGCTGTGTTACATC
        **     ** ** ** ** ** ** **   ** ** *****  ** **  *****

WTREP   CATCATATCATGGGAAAGGTGCCAGACGCTTGCACTGCCTGCGATCTGGTCAATGTGGAT 2159
dREP    CACCATATTATGGGCAAAGTGCCCGACGCATGCACCGCATGCGATCTGGTGAACGTCGAC
sREP    CACCACATTATGGGGAAAGTCCCCGATGCCTGTACCGCATGCGACCTGGTGAACGTTGAC
        ** ** ** ***** ** ** ** ** ** **  ** ** ***** ***** ** ** **

WTREP   TTGGATGACTGCATCTTTGAACAATAA                                    2186
dREP    CTCGACGATTGCATTTTTGAACAGTAA
sREP    CTCGACGACTGCATTTTTCGAGCAGTAA
         * ** ** *****  ** ** ** ***
```

A. Segment 11: bp 1647-1781 of GenBank accession number AF043303.1

Wild type nucleotide sequence (SEQ ID NO:21)

GACCGGATGTTCAAATTTGAACTCACCCGCGTCTGGATCATGACTTTGGGAAGGTCACCAAGCAGGAAGTCAAAGACTTTTTCCGGTGGG
CAAAGGATCACGTGGTTGAGGTGGAGCATGAATTCTACGTCAAA

Wild type amino acid sequence (SEQ ID NO:22)

D R M F K F E L T R R L D H D F G K V T K Q E V K D F F R W A K D H V V E V E H E F Y V K

Scrambled nucleotide sequence (SEQ ID NO:23)

*GATCGTATGTTTAAGTTCGAGTTGACTCGGCGGCTGGACCACGATTTCGGCAAAGTGACGAAACAGGAGGTGAAGGACTTCTTTAGATGG*
*GCCAAGGACCACGTGGTGGAGGTCGAGCACGAGTTTTATGTGAAG*

B. Segment 13: bp 1917-2051 of GenBank accession number AF043303.1

Wild type nucleotide sequence (SEQ ID NO:24)

AAATGTTCTCGTCACGTGGGCATGAATCTGATGCTGTTTCCCTGCAGACAATGCGAGAGAATGAATCAGAATTCAAATATCTGCTTCACTCA
CGGACAGAAAGACTGTTTAGAGTGCTTTCCCGTGTCAGAATCT

Wild type amino acid sequence (SEQ ID NO:25)

K C S R H V G M N L M L F P C R Q C E R M N Q N S N I C F T H G Q K D C L E C F P V S E S

Scrambled nucleotide sequence (SEQ ID NO:26)

*AAGTGCTCAAGGCATGTCGGGATGAACCTGATGCTGTTCCCATGCCGCCAGTGCGAGCGCATGAACCAGAACAGCAACATTTGTTTTACCC*
*ACGGGCAGAAGGATTGCCTGGAATGCTTCCCGGTCAGCGAGTCA*

FIGURE 15A

C. Segment 14: bp 2052-2186 of GenBank accession number AF043303.1

Wild type nucleotide sequence (SEQ ID NO:27)

CAACCCGTTTCTGTCGTCAAAAAGGGCTATCAGAAACTGTGCTACATTCATCATCATATCATGGGAAAGGTGCCAGACGCTTGCACTGCCTGCG
ATCTGGTCAATGTGGATTTGGATGACTGCATCTTTGAACAATAA

Wild type amino acid sequence (SEQ ID NO:28)

Q P V S V V K K A Y Q K L C Y I H H I M G K V P D A C T A C D L V N V D L D D C I F E Q Stop Scrambled nucleotide sequence (SEQ ID NO:29)

CAGCCGGTGTCCGTGGTGAAGAAAGCCTACCAAAAGCTGTGTTACATCCACCACATTATGGGAAAGTCCCCGATGCCTGTACCGCATGCG
ACCTGGTGAACGTTGACCTCGACGACTGCATTTTCGAGCAGTAA*

D. Segment 12: 135bp sequence: bp1782-1916 of GenBank accession number AF043303.1

Wild type nucleotide sequence (SEQ ID NO:01)

AAGGGTGGAGCCAAGAAAAGACCCGCCCCCAGTGACGCAGATATAAGTGAGCCCAAACGGGTGCGCGAGTCAGTTGCGCAGCCATCGAC
GTCAGACGCGGAAGCTTCGATCAACTACGCAGACAGGTACCAAAAC

Wild type amino acid sequence (SEQ ID NO:02)

K G G A K K R P A P S D A D I S E P K R V R E S V A Q P S T S D A E A S I N Y A D R Y Q N

Scrambled nucleotide sequence (SEQ ID NO:07)

*AAGGGGGGGGCCAAAAAGCGCCCTGCACCTTCCGACGCCGACATTTCCGAGCCAAAGAGAGTGCGTGAGAGTGTGGCCCAACCCTCCACC
AGTGATGCCGAGGCCTCCATTAATTATGCCGACCGCTATCAGAAT*

FIGURE 15B

A. Segment 11 scrambled nucleotide sequence (SEQ ID NO:23)

GATCGTATGTTAAGTTCGAGTTGACTCGGCGGCTGGACCACGATTTCGGCAAAGTGACGAAACAGGAGGTGAAGGA
CTTCTTTAGATGGGCCAAGGACCACGTGTGGAGGTCGAGCACGAGTTTATGTGAAG

B. Segment 13 scrambled nucleotide sequence (SEQ ID NO:26)

AAGTGCTCAAGGCATGTCGGGATGAACCTGATGTCGTTCCCATGCCGCCAGTGCGAGGCGCATGAACCAGAACAGCAA
CATTGTTTTACCCACGGGCAGAAGGATTGCCTGGAATGCTTCCCGGTCAGCGAGTCA

C. Segment 14 scrambled nucleotide sequence (SEQ ID NO:29)

CAGCCGGGTGTCCGTGGTGAAGAAAGCCTACCAAAAGTCTGTGTTACATCCACCACATTATGGGGAAAGTCCCCGATGCC
TGTACCGCATGCGACCTGGTGAACGTTGACCTCGAGACTGCATTTCGAGCAGTAA

D. Segment 12 scrambled nucleotide sequence (135bp sequence) (SEQ ID NO:07)

AAGGGGGGGCCAAAAGCCCTGCACCTTCCGACGCCGACATTTCCGAGCCAAAGAGAGTGCGTGAGAGTGTGG
CCCAACCCTCCACCAGTGATGCCGAGGCCTCCATTAATTATGCCGACCGCTATCAGAAT

Figure 16

SEQUENCE LISTING

```
<160> NUMBER OF SEQ ID NOS: 29

<210> SEQ ID NO 1
<211> LENGTH: 135
<212> TYPE: DNA
<213> ORGANISM: adeno-associated virus 2

<400> SEQUENCE: 1
aagggtggag ccaagaaaag acccgccccc agtgacgcag atataagtga gcccaaacgg      60
gtgcgcgagt cagttgcgca gccatcgacg tcagacgcgg aagcttcgat caactacgca     120
gacaggtacc aaaac                                                      135

<210> SEQ ID NO 2
<211> LENGTH: 45
<212> TYPE: PRT
<213> ORGANISM: adeno-associated virus 2

<400> SEQUENCE: 2

Lys Gly Gly Ala Lys Lys Arg Pro Ala Pro Ser Asp Ala Asp Ile Ser
1               5                   10                  15

Glu Pro Lys Arg Val Arg Glu Ser Val Ala Gln Pro Ser Thr Ser Asp
            20                  25                  30

Ala Glu Ala Ser Ile Asn Tyr Ala Asp Arg Tyr Gln Asn
        35                  40                  45

<210> SEQ ID NO 3
<211> LENGTH: 1865
<212> TYPE: DNA
<213> ORGANISM: adeno-associated virus 2

<400> SEQUENCE: 3
atgccggggt tttacgagat tgtgattaag gtccccagcg accttgacga gcatctgccc      60
ggcatttctg acagctttgt gaactgggtg gccgagaagg aatgggagtt gccgccagat     120
tctgacatgg atctgaatct gattgagcag gcacccctga ccgtggccga gaagctgcag     180
cgcgactttc tgacggaatg gcgccgtgtg agtaaggccc cggaggccct tttctttgtg     240
caatttgaga agggagagag ctacttccac atgcacgtgc tcgtggaaac caccggggtg     300
aaatccatgg ttttgggacg tttcctgagt cagattcgcg aaaaactgat tcagagaatt     360
taccgcggga tcgagccgac tttgccaaac tggttcgcgg tcacaaagac cagaaatggc     420
gccggaggcg ggaacaaggt ggtggatgag tgctacatcc ccaattactt gctccccaaa     480
acccagcctg agctccagtg ggcgtggact aatatggaac agtatttaag cgcctgtttg     540
aatctcacgg agcgtaaacg gttggtggcg cagcatctga cgcacgtgtc gcagacgcag     600
gagcagaaca aagagaatca gaatcccaat tctgatgcgc cggtgatcag atcaaaaact     660
tcagccaggt acatggagct ggtcgggtgg ctcgtggaca ggggattac ctcggagaag     720
```

-continued

```
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatcccaa tatgcggctt ccgtcttct gggatgggcc    960 acgaaaaagt tcggcaagag gaacaccatc tggctgtttg ggcctgcaac taccgggaag   1020
accaacatcg cggaggccat agcccacact gtgcccttct acgggtgcgt aaactggacc   1080
aatgagaact ttcccttcaa cgactgtgtc gacaagatgg tgatctggtg ggaggagggg   1140
aagatgaccg ccaaggtcgt gagtcggcc aaagccattc tcggaggaag caaggtgcgc   1200
gtggaccaga atgcaagtc ctcggcccag atagacccga ctcccgtgat cgtcacctcc   1260
aacaccaaca tgtgcgccgt gattgacggg aactcaacga ccttcgaaca ccagcagccg   1320
ttgcaaaccg gatgttcaaa tttgaactca cccgccgtct ggatcatgac tttgggaagg   1380
tcaccaagca ggaagtcaaa gactttttcc ggtgggcaaa ggatcacgtg gttgaggtgg   1440
agcatgaatt ctacgtcaaa aagggtggag ccaagaaaag acccgccccc agtgacgcag   1500
atataagtga gcccaaacgg gtgcgcgagt cagttgcgca gccatcgacg tcagacgcgg   1560
aagcttcgat caactacgca gacaggtacc aaaacaaatg ttctcgtcac gtgggcatga   1620
atctgatgct gtttccctgc agacaatgcg agagaatgaa tcagaattca aatatctgct   1680
tcactcacgg acagaaagac tgtttagagt gctttcccgt gtcagaatct caacccgttt   1740
ctgtcgtcaa aaaggcgtat cagaaactgt gctacattca tcatatcatg ggaaaggtgc   1800
cagacgcttg cactgcctgc gatctggtca atgtggattt ggatgactgc atctttgaac   1860
aataa                                                                1865
```

<210> SEQ ID NO 4
<211> LENGTH: 621
<212> TYPE: PRT
<213> ORGANISM: adeno-associated virus 2

<400> SEQUENCE: 4

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
```

```
                165                 170                 175
Ser Ala Cys Leu Asn Leu Thr Glu Arg Lys Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

Arg Tyr Gln Asn Lys Cys Ser Arg His Val Gly Met Asn Leu Met Leu
    530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590
```

```
Ile His His Ile Met Gly Lys Val Pro Asp Ala Cys Thr Ala Cys Asp
        595                 600                 605
Leu Val Asn Val Asp Leu Asp Cys Ile Phe Glu Gln
    610                 615                 620

<210> SEQ ID NO 5
<211> LENGTH: 536
<212> TYPE: PRT
<213> ORGANISM: adeno-associated virus 2

<400> SEQUENCE: 5

Met Pro Gly Phe Tyr Glu Ile Val Ile Lys Val Pro Ser Asp Leu Asp
1               5                   10                  15
Glu His Leu Pro Gly Ile Ser Asp Ser Phe Val Asn Trp Val Ala Glu
            20                  25                  30
Lys Glu Trp Glu Leu Pro Pro Asp Ser Asp Met Asp Leu Asn Leu Ile
        35                  40                  45
Glu Gln Ala Pro Leu Thr Val Ala Glu Lys Leu Gln Arg Asp Phe Leu
    50                  55                  60
Thr Glu Trp Arg Arg Val Ser Lys Ala Pro Glu Ala Leu Phe Phe Val
65                  70                  75                  80
Gln Phe Glu Lys Gly Glu Ser Tyr Phe His Met His Val Leu Val Glu
                85                  90                  95
Thr Thr Gly Val Lys Ser Met Val Leu Gly Arg Phe Leu Ser Gln Ile
            100                 105                 110
Arg Glu Lys Leu Ile Gln Arg Ile Tyr Arg Gly Ile Glu Pro Thr Leu
        115                 120                 125
Pro Asn Trp Phe Ala Val Thr Lys Thr Arg Asn Gly Ala Gly Gly Gly
    130                 135                 140
Asn Lys Val Val Asp Glu Cys Tyr Ile Pro Asn Tyr Leu Leu Pro Lys
145                 150                 155                 160
Thr Gln Pro Glu Leu Gln Trp Ala Trp Thr Asn Met Glu Gln Tyr Leu
                165                 170                 175
Ser Ala Cys Leu Asn Leu Thr Glu Arg Lys Arg Leu Val Ala Gln His
            180                 185                 190
Leu Thr His Val Ser Gln Thr Gln Glu Gln Asn Lys Glu Asn Gln Asn
        195                 200                 205
Pro Asn Ser Asp Ala Pro Val Ile Arg Ser Lys Thr Ser Ala Arg Tyr
    210                 215                 220
Met Glu Leu Val Gly Trp Leu Val Asp Lys Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Gly Lys
            260                 265                 270
Ile Met Ser Leu Thr Lys Thr Ala Pro Asp Tyr Leu Val Gly Gln Gln
        275                 280                 285
Pro Val Glu Asp Ile Ser Ser Asn Arg Ile Tyr Lys Ile Leu Glu Leu
    290                 295                 300
Asn Gly Tyr Asp Pro Gln Tyr Ala Ala Ser Val Phe Leu Gly Trp Ala
305                 310                 315                 320
Thr Lys Lys Phe Gly Lys Arg Asn Thr Ile Trp Leu Phe Gly Pro Ala
                325                 330                 335
Thr Thr Gly Lys Thr Asn Ile Ala Glu Ala Ile Ala His Thr Val Pro
```

```
                340              345              350
Phe Tyr Gly Cys Val Asn Trp Thr Asn Glu Asn Phe Pro Phe Asn Asp
        355                  360                 365
Cys Val Asp Lys Met Val Ile Trp Trp Glu Glu Gly Lys Met Thr Ala
    370                 375                 380
Lys Val Val Glu Ser Ala Lys Ala Ile Leu Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
            420                 425                 430
Thr Thr Phe Glu His Gln Gln Pro Leu Gln Asp Arg Met Phe Lys Phe
        435                 440                 445
Glu Leu Thr Arg Arg Leu Asp His Asp Phe Gly Lys Val Thr Lys Gln
    450                 455                 460
Glu Val Lys Asp Phe Phe Arg Trp Ala Lys Asp His Val Val Glu Val
465                 470                 475                 480
Glu His Glu Phe Tyr Val Lys Lys Gly Gly Ala Lys Lys Arg Pro Ala
                485                 490                 495
Pro Ser Asp Ala Asp Ile Ser Glu Pro Lys Arg Val Arg Glu Ser Val
            500                 505                 510
Ala Gln Pro Ser Thr Ser Asp Ala Glu Ala Ser Ile Asn Tyr Ala Asp
        515                 520                 525
Arg Leu Ala Arg Gly His Ser Leu
    530                 535

<210> SEQ ID NO 6
<211> LENGTH: 1866
<212> TYPE: DNA
<213> ORGANISM: Artificial sequence
<220> FEATURE:
<223> OTHER INFORMATION: synthetic

<400> SEQUENCE: 6
atgcccggat ctacgaaat cgtcatcaaa gtgccctctg acttggatga acacctgccg      60
gggatcagcg attctttcgt caattgggtc gcggagaaag agtgggaact tccccccgac    120
tcggacatgg acctgaactt aatcgagcaa gccccgctga cggtggcgga aaactgcag    180 cgggactttc tgaccgagtg gaggcgcgta tcgaaagcgc cgaagctttt gttttcgtc    240 cagttcgaga ggggggagtc gtactttcat atgcatgtgt tggtggagac tacgggagtg    300
aagagtatgg tgctagggag gtttctgtcg caaataagag agaagctgat ccagcggata    360
taccgtggca ttgagcccac ccttcccaat tggtttgccg tgaccaaaac tcgtaacgga    420 gcagggggg gaaataaagt cgtcgacgag tgctatattc gaactacct cttgcccaag      480 acgcagcccg aattgcagtg ggcctggacc aacatggagc aatacctgtc agcgtgcctc    540
aacttgaccg aaagaaagag actcgtggcc cagcacctga cccatgtctc acagacccag    600
gaacagaata aggaaaacca aaacccaaat agcgacgccc ccgtgatacg gagcaagacc    660
agcgctcgct acatggagtt agtgggatgg ttggtggata aggaatcac gtctgagaaa    720 caatggattc aggaggacca ggcgtcctac attagtttta cgccgcgtc aaatagcaga    780 tctcagatta agccgcgct cgataacgcc ggcaaaatca tgtcgctgac caagacagct    840
cccgactacc tggtgggaca gcagccggtg gaggacatct cttctaaccg tatctacaag    900
atccttgagt tgaatggcta cgacccacag tacgccgcct cagtgtttct gggctgggca    960
```

```
accaagaaat tgggaaacg caatacgatt tggctgttcg acccgccac cactggtaag    1020 actaatattg ccgaggcgat cgcacatacc gttccgtttt acggatgcgt gaattggact   1080
aacgaaaatt tccccttaa tgattgcgtg acaagatgg ttatttggtg ggaggaagga    1140
aagatgactg cgaaagtggt ggaatccgct aaggctatct tgggggggtc gaaagttcgg   1200
gtcgaccaga agtgcaaatc gtccgcgcag attgacccca cccccgtgat tgtgacgtca   1260
aatactaata tgtgtgcggt catcgatggc aatagcacca ctttcgaaca tcagcaaccc   1320
ctccaggatc gtatgtttaa gttcgagttg actcggcggc tggaccacga tttcggcaaa   1380
gtgacgaaac aggaggtgaa ggacttcttt agatgggcca aggaccacgt ggtggaggtc   1440
gagcacgagt tttatgtgaa aaggggggg gccaaaaagc gccctgcacc ttccgacgcc    1500
gacattcccg agccaaagag agtgcgtgag agtgtggccc aaccctccac cagtgatgcc   1560
gaggcctcca ttaattatgc cgaccgctat cagaataagt gctcaaggca tgtcgggatg   1620
aacctgatgc tgttcccatg ccgccagtgc gagcgcatga accagaacag caacatttgt   1680
tttacccacg ggcagaagga ttgcctggaa tgcttcccgg tcagcgagtc acagccggtg   1740
tccgtggtga agaaagccta ccaaaagctg tgttacatcc accacattat ggggaaagtc   1800
cccgatgcct gtaccgcatg cgacctggtg aacgttgacc tcgacgactg cattttcgag   1860
cagtaa                                                              1866

<210> SEQ ID NO 7
<211> LENGTH: 135
<212> TYPE: DNA
<213> ORGANISM: Artificial sequence
<220> FEATURE:
<223> OTHER INFORMATION: synthetic

<400> SEQUENCE: 7 aaggggggg ccaaaaagcg ccctgcacct tccgacgccg acatttccga gccaaagaga    60
gtgcgtgaga gtgtggccca accctccacc agtgatgccg aggcctccat taattatgcc   120
gaccgctatc agaat                                                    135

<210> SEQ ID NO 8
<211> LENGTH: 1866
<212> TYPE: DNA
<213> ORGANISM: Artificial sequence
<220> FEATURE:
<223> OTHER INFORMATION: synthetic

<400> SEQUENCE: 8
atgcccgggt tttacgagat cgtgattaag gtgccatccg atctcgacga gcatctgccc    60
gggattagcg attcgttcgt gaattgggtc gccgaaaagg agtgggagtt gccccccgat   120
agcgatatgg acctgaatct gatcgagcag gcccccctta ccgtcgccga gaaactgcaa   180
cgcgatttct tgaccgagtg gagacgcgtg agtaaggccc ccgaagccct gttttcgtg    240 caatttgaaa agggcgagtc atactttcat atgcacgtgt tggtcgagac taccggcgtt   300
aagtctatgg tgctcggacg gtttctgtca cagatacgcg aaaaactgat ccagcgtatc   360
tatcgcggaa tcgagccaac cctaccgaat tggttcgccg ttacgaagac ccgtaacggc   420
gccggggggg ggaataaggt ggtcgacgag tgctatatcc ctaactatct gttaccgaaa   480
acgcaacccg agttgcagtg ggcctggact aacatggagc aatacttgtc cgcatgcctg   540
aatctgaccg aacgcaaacg gttggtcgcc cagcatctga cacacgtgag tcagacccag   600
```

-continued

```
gagcagaata aggagaatca gaatccgaac tccgacgccc ccgtgatacg gtctaagact    660
agcgctaggt atatggagtt ggtggggtgg ttggtcgaca aggggattac ctccgagaaa    720
cagtggatcc aggaggacca ggcgtcatac atttcgttta acgccgcatc gaactcacgg    780
tcacagatta aggccgcact cgacaacgcc ggtaagatta tgagtctgac taagaccgcc    840
cccgattact tagtgggaca gcaacccgtc gaggacattt cgagtaatcg gatttacaaa    900
atcctcgaac ttaacggata cgaccccaa tacgccgcta gcgtgtttct ggggtgggcg      960
actaagaaat tcggaaagcg taatacgatt tggttgttcg acccgctac gaccggcaaa    1020 acgaatatcg ccgaagcgat cgcgcatacc gtgccattct acgggtgcgt gaattggacg   1080
aacgagaact ttccgtttaa cgattgcgtc gacaagatgg tgatttggtg ggaggaggga   1140
aagatgaccg ctaaggtggt cgagtccgcg aaagcgattc tgggggggtc taaggtgaga   1200
gtcgaccaga agtgtaagtc ttcggctcag atcgatccga ccccgtgat cgtgacctct   1260 aacactaaca tgtgcgccgt gatcgacggg aattcgacta cgttcgaaca ccagcagcca   1320
ttgcaggacc gtatgttcaa atttgaactg actaggagac tcgaccacga cttcggaaag   1380
gtgactaagc aggaggtgaa agacttttt cggtgggcga aagaccatgt ggtcgaggtc    1440
gagcacgagt tttacgtgaa aaagggcgga gcgaaaaaga ccccgccccc tagcgacgcc   1500
gacattagcg aaccgaaacg cgtacgcgaa tccgttgcgc aaccgtcaac ctccgacgcc   1560
gaagcgtcaa tcaattacgc cgataggtac cagaataagt gctctagaca cgtggggatg   1620
aatctgatgc tgtttccctg tagacagtgc gagcgtatga accagaactc gaacatttgc   1680
tttacccacg gacagaaaga ctgtctcgaa tgctttcccg tgtccgaatc gcaacccgtt   1740
agcgtggtga aaaagcgta ccagaaactg tgttacatac accatattat gggcaaagtg     1800
cccgacgcat gcaccgcatg cgatctggtg aacgtcgacc tcgacgattg cattttgaa    1860 cagtaa                                                               1866
```

<210> SEQ ID NO 9
<211> LENGTH: 135
<212> TYPE: DNA
<213> ORGANISM: Artificial sequence
<220> FEATURE:
<223> OTHER INFORMATION: synthetic

<400> SEQUENCE: 9

```
aagggcggag cgaaaaagag acccgcccct agcgacgccg acattagcga accgaaacgc     60
gtacgcgaat ccgttgcgca accgtcaacc tccgacgccg aagcgtcaat caattacgcc   120
gataggtacc agaat                                                    135
```

<210> SEQ ID NO 10
<211> LENGTH: 145
<212> TYPE: DNA
<213> ORGANISM: adeno-associated virus 2

<400> SEQUENCE: 10

```
ttggccactc cctctctgcg cgctcgctcg ctcactgagg ccgggcgacc aaaggtcgcc    60
cgacgcccgg gctttgcccg gcggcctca gtgagcgagc gagcgcgcag agagggagtg   120
gccaactcca tcactagggg ttcct                                          145
```

<210> SEQ ID NO 11
<211> LENGTH: 140
<212> TYPE: DNA
<213> ORGANISM: Artificial sequence
<220> FEATURE:
<223> OTHER INFORMATION: synthetic

<400> SEQUENCE: 11
gtggagtcgt gacgtgaatt acgtcatagg gttagggagg tcctgtatta gaggtcacgt   60
gagtgttttg cgacattttg cgacaccatg tggtcacgct gggtatttaa gcccgagtga  120
gcacgcaggg tctccatttt                                              140

<210> SEQ ID NO 12
<211> LENGTH: 20
<212> TYPE: PRT
<213> ORGANISM: Artificial sequence
<220> FEATURE:
<223> OTHER INFORMATION: synthetic

<400> SEQUENCE: 12

Glu Tyr Leu Asn Lys Ile Gln Asn Ser Leu Ser Thr Glu Trp Ser Pro
1               5                   10                  15

Cys Ser Val Thr
            20

<210> SEQ ID NO 13
<211> LENGTH: 24
<212> TYPE: PRT
<213> ORGANISM: Artificial Sequence
<220> FEATURE:
<223> OTHER INFORMATION: Synthetic

<400> SEQUENCE: 13

Asn Ala Asn Pro Asn Ala Asn Pro Asn Ala Asn Pro Asn Ala Asn Pro
1               5                   10                  15

Asn Ala Asn Pro Asn Ala Asn Pro
            20

<210> SEQ ID NO 14
<211> LENGTH: 9
<212> TYPE: PRT
<213> ORGANISM: Artificial sequence
<220> FEATURE:
<223> OTHER INFORMATION: synthetic

<400> SEQUENCE: 14

Ala Met Gln Met Leu Lys Glu Thr Ile
1               5

<210> SEQ ID NO 15
<211> LENGTH: 9
<212> TYPE: PRT
<213> ORGANISM: Artificial sequence
<220> FEATURE:
<223> OTHER INFORMATION: synthetic

<400> SEQUENCE: 15

Tyr Pro Tyr Asp Val Pro Asp Tyr Ala
1               5

<210> SEQ ID NO 16
<211> LENGTH: 4679
<212> TYPE: DNA
<213> ORGANISM: adeno-associated virus 2

<400> SEQUENCE: 16
ttggccactc cctctctgcg cgctcgctcg ctcactgagg ccgggcgacc aaaggtcgcc   60

```
cgacgcccgg gctttgcccg ggcggcctca gtgagcgagc gagcgcgcag agagggagtg    120
gccaactcca tcactagggg ttcctggagg ggtggagtcg tgacgtgaat tacgtcatag    180
ggttagggag gtcctgtatt agaggtcacg tgagtgtttt gcgacatttt gcgacaccat    240
gtggtcacgc tgggtattta agcccgagtg agcacgcagg gtctccattt tgaagcggga    300
ggtttgaacg cgcagccgcc atgccgggt tttacgagat tgtgattaag gtccccagcg     360
accttgacga gcatctgccc ggcatttctg acagctttgt gaactgggtg ccgagaagg     420 aatgggagtt gccgccagat tctgacatgg atctgaatct gattgagcag gcacccctga    480
ccgtggccga aagctgcag cgcgactttc tgacggaatg gcgccgtgtg agtaaggccc     540
cggaggccct tttctttgtg caatttgaga agggagagag ctacttccac atgcacgtgc    600
tcgtggaaac caccgggtg aaatccatgg ttttgggacg tttcctgagt cagattcgcg     660
aaaaactgat tcagagaatt taccgcggga tcgagccgac tttgccaaac tggttcgcgg    720
tcacaaagac cagaaatggc gccgaggcg ggaacaaggt ggtggatgag tgctacatcc     780
ccaattactt gctccccaaa acccagcctg agctccagtg ggcgtggact aatatggaac    840
agtatttaag cgcctgttg aatctcacgg agcgtaaacg gttggtggcg cagcatctga     900
cgcacgtgtc gcagacgcag gagcagaaca aagagaatca gaatcccaat tctgatgcgc    960
cggtgatcag atcaaaaact tcagccaggt acatggagct ggtcgggtgg ctcgtggaca   1020
aggggattac ctcggagaag cagtggatcc aggaggacca ggcctcatac atctccttca   1080
atgcggcctc caactcgcgg tcccaaatca aggctgcctt ggacaatgcg ggaaagatta   1140
tgagcctgac taaaaccgcc cccgactacc tggtgggcca gcagcccgtg gaggacattt   1200
ccagcaatcg gatttataaa attttggaac taaacgggta cgatccccaa tatgcggctt   1260
ccgtctttct gggatgggcc acgaaaaagt tcggcaagag gaacaccatc tggctgtttg   1320
ggcctgcaac taccgggaag accaacatcg cggaggccat agcccacact gtgcccttct   1380
acgggtgcgt aaactggacc aatgagaact ttcccttcaa cgactgtgtc gacaagatgg   1440
tgatctggtg ggaggagggg aagatgaccg ccaaggtcgt ggagtcggcc aaagccattc   1500
tcggaggaag caaggtgcgc gtggaccaga atgcaagtc ctcggcccag atagacccga    1560
ctcccgtgat cgtcacctcc aacaccaaca tgtgcgccgt gattgacggg aactcaacga   1620
ccttcgaaca ccagcagccg ttgcaagacc ggatgttcaa atttgaactc acccgccgtc   1680
tggatcatga ctttgggaag gtcaccaagc aggaagtcaa agacttttc cggtgggcaa     1740 aggatcacgt ggttgaggtg gagcatgaat tctacgtcaa aaagggtgga gccaagaaaa   1800
gacccgcccc cagtgacgca gatataagtg agcccaaacg ggtgcgcgag tcagttgcgc   1860
agccatcgac gtcagacgcg gaagcttcga tcaactacgc agacaggtac caaaacaaat   1920
gttctcgtca cgtgggcatg aatctgatgc tgtttccctg cagacaatgc gagagaatga   1980
atcagaattc aaatatctgc ttcactcacg gacagaaaga ctgtttagag tgctttcccg   2040
tgtcagaatc tcaacccgtt tctgtcgtca aaaaggcgta tcagaaactg tgctacattc   2100
atcatatcat gggaaaggtg ccagacgctt gcactgcctg cgatctggtc aatgtggatt   2160
tggatgactg catctttgaa caataaatga tttaaatcag gtatggctgc cgatggttat   2220
cttccagatt ggctcgagga cactctctct gaaggaataa gacagtggtg gaagctcaaa   2280
cctggcccac caccaccaaa gcccgcagag cggcataagg acgacagcag ggtcttgtg    2340 cttcctgggt acaagtacct cggacccttc aacggactcg acaagggaga gccggtcaac   2400
gaggcagacg ccgcggccct cgagcacgac aaagcctacg accggcagct cgacagcgga   2460
```

```
gacaacccgt acctcaagta caaccacgcc gacgcggagt ttcaggagcg ccttaaagaa    2520
gatacgtctt ttgggggcaa cctcggacga gcagtcttcc aggcgaaaaa gagggttctt    2580
gaacctctgg gcctggttga ggaacctgtt aagacggctc cgggaaaaaa gaggccggta    2640
gagcactctc ctgtggagcc agactcctcc tcgggaaccg gaaaggcggg ccagcagcct    2700
gcaagaaaaa gattgaattt tggtcagact ggagacgcag actcagtacc tgaccccag     2760
cctctcggac agccaccagc agcccctct  ggtctgggaa ctaatacgat ggctacaggc    2820
agtggcgcac caatggcaga caataacgag ggcgccgacg gagtgggtaa ttcctcggga    2880
aattggcatt gcgattccac atggatgggc gacagagtca tcaccaccag cacccgaacc    2940
tgggccctgc ccacctacaa caaccacctc tacaaacaaa tttccagcca atcaggagcc    3000
tcgaacgaca atcactactt tggctacagc acccccttgg ggtattttga cttcaacaga    3060
ttccactgcc acttttcacc acgtgactgg caaagactca tcaacaacaa ctggggattc    3120
cgacccaaga gactcaactt caagctcttt aacattcaag tcaaagaggt cacgcagaat    3180
gacggtacga cgacgattgc caataacctt accagcacgg ttcaggtgtt tactgactcg    3240
gagtaccagc tcccgtacgt cctcggctcg gcgcatcaag gatgcctccc gccgttccca    3300
gcagacgtct tcatggtgcc acagtatgga tacctcaccc tgaacaacgg gagtcaggca    3360
gtaggacgct cttcatttta ctgcctggag tactttcctt tcagatgct gcgtaccgga     3420
aacaacttta ccttcagcta cacttttgag gacgttcctt tccacagcag ctacgctcac    3480
agccagagtc tggaccgtct catgaatcct ctcatcgacc agtacctgta ttacttgagc    3540
agaacaaaca ctccaagtgg aaccaccacg cagtcaaggc ttcagttttc tcaggccgga    3600
gcgagtgaca ttcgggacca gtctaggaac tggcttcctg gaccctgtta ccgccagcag    3660
cgagtatcaa agacatctgc ggataacaac aacagtgaat actcgtggac tggagctacc    3720
aagtaccacc tcaatggcag agactctctg tgaatccgg gcccggccat ggcaagccac    3780
aaggacgatg aagaaaagtt ttttcctcag agcggggttc tcatctttgg gaagcaaggc    3840
tcagagaaaa caaatgtgga cattgaaaag gtcatgatta cagacgaaga ggaaatcagg    3900
acaaccaatc ccgtggctac ggagcagtat ggttctgtat ctaccaacct ccagagaggc    3960
aacagacaag cagctaccgc agatgtcaac acacaaggcg ttcttccagg catggtctgg    4020
caggacagag atgtgtacct tcaggggccc atctgggcaa agattccaca cacggacgga    4080
cattttcacc cctctcccct catgggtgga ttcggactta acaccctcc  tccacagatt     4140
ctcatcaaga cacccccggt acctgcgaat ccttcgacca ccttcagtgc ggcaaagttt    4200
gcttccttca tcacacagta ctccacggga caggtcagcg tggagatcga gtgggagctg    4260
cagaaggaaa acagcaaacg ctggaatccc gaaattcagt acacttccaa ctacaacaag    4320
tctgttaatg tggactttac tgtggacact aatggcgtgt attcagagcc tcgccccatt    4380
ggcaccagat acctgactcg taatctgtaa ttgcttgtta atcaataaac cgtttaattc    4440
gtttcagttg aactttggtc tctgcgtatt tctttcttat ctagtttcca tggctacgta    4500
gataagtagc atggcgggtt aatcattaac tacaaggaac ccctagtgat ggagttggcc    4560
actccctctc tgcgcgctcg ctcgctcact gaggccgggc gaccaaaggt cgcccgacgc    4620
ccgggctttg cccgggcggc ctcagtgagc gagcgagcgc gcagagaggg agtggccaa     4679

<210> SEQ ID NO 17
<211> LENGTH: 564
<212> TYPE: DNA
```

<213> ORGANISM: adeno-associated virus 2

<400> SEQUENCE: 17

```
ttcgaacacc agcagccgtt gcaagaccgg atgttcaaat ttgaactcac ccgccgtctg      60
gatcatgact ttgggaaggt caccaagcag gaagtcaaag acttttccg gtgggcaaag      120
gatcacgtgg ttgaggtgga gcatgaattc tacgtcaaaa agggtggagc caagaaaaga     180
cccgccccca gtgacgcaga tataagtgag cccaaacggg tgcgcgagtc agttgcgcag     240
ccatcgacgt cagacgcgga agcttcgatc aactacgcag acaggtacca aaacaaatgt     300
tctcgtcacg tgggcatgaa tctgatgctg tttccctgca gacaatgcga gagaatgaat     360
cagaattcaa atatctgctt cactcacgga cagaaagact gtttagagtg ctttcccgtg     420
tcagaatctc aacccgtttc tgtcgtcaaa aaggcgtatc agaaactgtg ctacattcat     480
catatcatgg gaaaggtgcc agacgcttgc actgcctgcg atctggtcaa tgtggatttg     540
gatgactgca tctttgaaca ataa                                            564
```

```
<210> SEQ ID NO 18
<211> LENGTH: 567
<212> TYPE: DNA
<213> ORGANISM: Artificial sequence
<220> FEATURE:
<223> OTHER INFORMATION: synthetic
```

<400> SEQUENCE: 18

```
actttcgaac atcagcaacc cctccaggat cgtatgttta agttcgagtt gactcggcgg      60
ctggaccacg atttcggcaa agtgacgaaa caggaggtga aggacttctt tagatgggcc     120
aaggaccacg tggtggaggt cgagcacgag ttttatgtga agaaggggg ggccaaaaag      180
cgccctgcac cttccgacgc cgacatttcc gagccaaaga gagtgcgtga gagtgtggcc     240
caacccctcca ccagtgatgc cgaggcctcc attaattatg ccgaccgcta tcagaataag    300
tgctcaaggc atgtcgggat gaacctgatg ctgttcccat gccgcagtg cgagcgcatg      360
aaccagaaca gcaacatttg ttttacccac gggcagaagg attgcctgga atgcttcccg     420
gtcagcgagt cacagccggt gtccgtggtg aagaaaagcct accaaaagct gttacatc      480
caccacatta tggggaaagt ccccgatgcc tgtaccgcat gcgacctggt gaacgttgac     540
ctcgacgact gcattttcga gcagtaa                                         567
```

```
<210> SEQ ID NO 19
<211> LENGTH: 567
<212> TYPE: DNA
<213> ORGANISM: Artificial sequence
<220> FEATURE:
<223> OTHER INFORMATION: synthetic
```

<400> SEQUENCE: 19

```
acgttcgaac accagcagcc attgcaggac cgtatgttca aatttgaact gactaggaga      60
ctcgaccacg acttcggaaa ggtgactaag caggaggtga agactttttt tcggtgggcg     120
aaagaccatg tggtcgaggt cgagcacgag ttttacgtga aaaagggcgg agcgaaaaag     180
agacccgccc ctagcgacgc cgacattagc gaaccgaaac gcgtacgcga atccgttgcg     240
caaccgtcaa cctccgacgc cgaagcgtca atcaattacg ccgataggta ccagaataag     300
tgctctagac acgtggggat gaatctgatg ctgtttccct gtagacagtg cgagcgtatg     360
aaccagaact cgaacatttg ctttacccac ggacagaaag actgtctcga atgctttccc     420
gtgtccgaat cgcaacccgt tagcgtggtg aaaaaagcgt accagaaact gtgttacata     480
```

```
caccatatta tgggcaaagt gcccgacgca tgcaccgcat gcgatctggt gaacgtcgac        540
ctcgacgatt gcattttga acagtaa                                             567

<210> SEQ ID NO 20
<211> LENGTH: 187
<212> TYPE: PRT
<213> ORGANISM: adeno-associated virus 2

<400> SEQUENCE: 20

Phe Glu His Gln Gln Pro Leu Gln Asp Arg Met Phe Lys Phe Glu Leu
1               5                   10                  15

Thr Arg Arg Leu Asp His Asp Phe Gly Lys Val Thr Lys Gln Glu Val
            20                  25                  30

Lys Asp Phe Phe Arg Trp Ala Lys Asp His Val Val Glu Val Glu His
        35                  40                  45

Glu Phe Tyr Val Lys Lys Gly Gly Ala Lys Lys Arg Pro Ala Pro Ser
    50                  55                  60

Asp Ala Asp Ile Ser Glu Pro Lys Arg Val Arg Glu Ser Val Ala Gln
65                  70                  75                  80

Pro Ser Thr Ser Asp Ala Glu Ala Ser Ile Asn Tyr Ala Asp Arg Tyr
                85                  90                  95

Gln Asn Lys Cys Ser Arg His Val Gly Met Asn Leu Met Leu Phe Pro
            100                 105                 110

Cys Arg Gln Cys Glu Arg Met Asn Gln Asn Ser Asn Ile Cys Phe Thr
        115                 120                 125

His Gly Gln Lys Asp Cys Leu Glu Cys Phe Pro Val Ser Glu Ser Gln
    130                 135                 140

Pro Val Ser Val Val Lys Lys Ala Tyr Gln Lys Leu Cys Tyr Ile His
145                 150                 155                 160

His Ile Met Gly Lys Val Pro Asp Ala Cys Thr Ala Cys Asp Leu Val
                165                 170                 175

Asn Val Asp Leu Asp Asp Cys Ile Phe Glu Gln
            180                 185

<210> SEQ ID NO 21
<211> LENGTH: 135
<212> TYPE: DNA
<213> ORGANISM: adeno-associated virus 2

<400> SEQUENCE: 21
gaccggatgt tcaaatttga actcacccgc cgtctggatc atgactttgg gaaggtcacc        60
aagcaggaag tcaaagactt tttccggtgg gcaaaggatc acgtggttga ggtggagcat       120
gaattctacg tcaaa                                                         135

<210> SEQ ID NO 22
<211> LENGTH: 45
<212> TYPE: PRT
<213> ORGANISM: adeno-associated virus 2

<400> SEQUENCE: 22

Asp Arg Met Phe Lys Phe Glu Leu Thr Arg Arg Leu Asp His Asp Phe
1               5                   10                  15

Gly Lys Val Thr Lys Gln Glu Val Lys Asp Phe Phe Arg Trp Ala Lys
            20                  25                  30

Asp His Val Val Glu Val Glu His Glu Phe Tyr Val Lys
        35                  40                  45
```

<210> SEQ ID NO 23
<211> LENGTH: 135
<212> TYPE: DNA
<213> ORGANISM: adeno-associated virus 2

<400> SEQUENCE: 23
gatcgtatgt ttaagttcga gttgactcgg cggctggacc acgatttcgg caaagtgacg    60
aaacaggagg tgaaggactt ctttagatgg gccaaggacc acgtggtgga ggtcgagcac   120
gagttttatg tgaag                                                    135

<210> SEQ ID NO 24
<211> LENGTH: 135
<212> TYPE: DNA
<213> ORGANISM: adeno-associated virus 2

<400> SEQUENCE: 24
aaatgttctc gtcacgtggg catgaatctg atgctgtttc cctgcagaca atgcgagaga    60
atgaatcaga attcaaatat ctgcttcact cacggacaga aagactgttt agagtgcttt   120
cccgtgtcag aatct                                                    135

<210> SEQ ID NO 25
<211> LENGTH: 45
<212> TYPE: PRT
<213> ORGANISM: adeno-associated virus 2

<400> SEQUENCE: 25

Lys Cys Ser Arg His Val Gly Met Asn Leu Met Leu Phe Pro Cys Arg
1               5                   10                  15

Gln Cys Glu Arg Met Asn Gln Asn Ser Asn Ile Cys Phe Thr His Gly
            20                  25                  30

Gln Lys Asp Cys Leu Glu Cys Phe Pro Val Ser Glu Ser
        35                  40                  45

<210> SEQ ID NO 26
<211> LENGTH: 135
<212> TYPE: DNA
<213> ORGANISM: adeno-associated virus 2

<400> SEQUENCE: 26
aagtgctcaa ggcatgtcgg gatgaacctg atgctgttcc catgccgcca gtgcgagcgc    60
atgaaccaga acagcaacat ttgttttacc cacgggcaga aggattgcct ggaatgcttc   120
ccggtcagcg agtca                                                    135

<210> SEQ ID NO 27
<211> LENGTH: 135
<212> TYPE: DNA
<213> ORGANISM: adeno-associated virus 2

<400> SEQUENCE: 27
caacccgttt ctgtcgtcaa aaaggcgtat cagaaactgt gctacattca tcatatcatg    60
ggaaaggtgc cagacgcttg cactgcctgc gatctggtca atgtggattt ggatgactgc   120
atctttgaac aataa                                                    135

<210> SEQ ID NO 28
<211> LENGTH: 44
<212> TYPE: PRT
<213> ORGANISM: adeno-associated virus 2

```
<400> SEQUENCE: 28

Gln Pro Val Ser Val Val Lys Lys Ala Tyr Gln Lys Leu Cys Tyr Ile
1               5                   10                  15

His His Ile Met Gly Lys Val Pro Asp Ala Cys Thr Ala Cys Asp Leu
            20                  25                  30

Val Asn Val Asp Leu Asp Asp Cys Ile Phe Glu Gln
        35                  40

<210> SEQ ID NO 29
<211> LENGTH: 135
<212> TYPE: DNA
<213> ORGANISM: adeno-associated virus 2

<400> SEQUENCE: 29
cagccggtgt ccgtggtgaa gaaagcctac caaaagctgt gttacatcca ccacattatg      60
gggaaagtcc ccgatgcctg taccgcatgc gacctggtga acgttgacct cgacgactgc     120
attttcgagc agtaa                                                      135
```

ADENO-ASSOCIATED-VIRUS REP SEQUENCES, VECTORS AND VIRUSES

This application is a continuation of, and claims priority to, co-pending U.S. patent application Ser. No. 14/795,214, filed on Jul. 9, 2015, issued as U.S. patent Ser. No. 10,214,730 on Feb. 26, 2019, which is a continuation of U.S. patent application Ser. No. 14/112,703, filed on Oct. 18, 2013, now abandoned, which is the U.S. National Entry of International Application No. PCT/US12/34247, filed on Apr. 19, 2012, now abandoned, which claims priority under 35 U.S.C. § 119(e) to U.S. Provisional Application Ser. No. 61/476,858, filed on Apr. 19, 2011, each of which is herein incorporated by reference in its entirety.

This invention was made with government support under grant AI041636, awarded by the National Institutes of Health (NIH). The government has certain rights in the invention.

FIELD OF INVENTION

The invention provides adeno-associated virus (AAV) replication (Rep) sequences. In one embodiment, the invention provides nucleotide sequences encoding a chimeric protein, wherein the encoded chimeric protein contains a wild type AAV Rep inhibitory amino acid sequence, and wherein the nucleotide sequences contain a scrambled and/or deoptimized polynucleotide sequence encoding the wild type AAV Rep inhibitory amino acid sequence. The invention provides vectors, cells, and viruses containing the invention's sequences. Also provided are methods for detecting portions of the AAV Rep inhibitory amino acid sequence, which reduce replication and/or infection and/or productive infection by viruses. The invention's compositions and methods are useful for site-specific integration and/or expression of heterologous sequences by recombinant adeno-associated virus (rAAV) vectors and by rAAV virus particles, such as hybrid viruses (e.g., Ad-AAV) comprising such vectors. The invention's compositions and methods find application in, for example, gene therapy and/or vaccines.

BACKGROUND

Sustained phenotypic correction of genetic defects requires a safe means of gene replacement. To date, many of these gene correction strategies use integrating lentiviruses or retroviruses for long-term gene replacement, although their clinical applications remain limited because of potential for viral-associated oncogenesis.

Gene correction strategies have attempted to use hybrid Adenovirus/Adeno-associated viruses (Ad/AAV) to combine the capacity, tropism and ease of production of adenovirus (Ad) with adeno-associated virus's (AAV's) ability for site-specific integration (SSI) into chromosome 19 AAVS1. Although the AAV Rep78 protein is required for SSI, the AAV Rep78 protein has the disadvantage of an inhibitory effect on Ad replication, particularly when co-expressed within the Ad backbone. This has lead to difficulty in the prior art in generating an integrating transgene within the back-bone of a single hybrid virus, such as Ad/AAV.

While an Adenovirus carrying the AAV cis acting elements can be constructed, construction of an Adenovirus carrying the Rep expression cassette has met with only limited success. Work by various authors has shown that coinfection with AAV in general, and Rep protein expression in particular, results in a 10% to 40% decrease in Adenoviral replication. Further, during co-infection of Ad and AAV, Rep protein has been shown to co-localize to Adenoviral replication centers and prevent their maturation. As a result, strategies to construct an Ad/AAV carrying Rep have focused on controlling Rep expression. The few successes reported have utilized tightly regulated expression systems, within a helper dependent Adenoviral vector. Although these vectors are free of adenoviral genes, they however need a helper virus for replication. Also, construction of a first generation Adenovirus carrying Rep has proved to be more difficult. Several reports exist of unsuccessful strategies for the construction of a first generation Ad carrying Rep.

In particular, a stable first generation adenovirus carrying AAV Rep78 has so far not been reproducibly constructed. Most viruses either fail to grow, showing no signs of viral replication (Ueno et al. (2000) *Biochemical and Biophysical Research Communications* 273(2):473-478), grow slowly, or are unstable, acquiring deletions within the Rep gene (Zolotukhin (2005) *Human Gene Therapy* 16(5):551-557). In one report, analysis of two clones bearing deletions revealed no overlap of the deletion sites within the Rep ORF (Zhang et al. (2001) *Gene Ther.* 8:704).

Thus there remains a need for new compositions and methods for safe, site-specific gene integration for applications that include gene therapy, vaccine, etc.

SUMMARY OF THE INVENTION

The invention provides a recombinant nucleotide sequence encoding a chimeric protein, a) wherein the encoded chimeric protein i) comprises at least a portion of wild type AAV Rep inhibitory amino acid sequence listed as SEQ ID NO:20, and ii) has Rep-mediated nuclease activity, and b) wherein the recombinant nucleotide sequence comprises a scrambled polynucleotide sequence encoding the at least portion of the wild type AAV Rep inhibitory amino acid sequence listed as SEQ ID NO:20.

In one embodiment, the nucleotide sequence further comprises a heterologous polynucleotide sequence operably linked to a first AAV ITR. In a preferred embodiment, the heterologous polynucleotide sequence is flanked by the first AAV ITR and by a second AAV ITR. In an alternative embodiment, the heterologous polynucleotide sequence comprises a therapeutic sequence, exemplified by a therapeutic sequence that encodes one or both of a disease associated polypeptide and an antigen polypeptide. In one embodiment, the nucleotide sequence further comprises a nucleic acid sequence encoding an AAV capsid protein. In another embodiment, the scrambled polynucleotide sequence comprises at least a portion of SEQ ID NO:18. In a more preferred embodiment, the portion of SEQ ID NO:18 comprises SEQ ID NO:07. In an alternative embodiment, the scrambled polynucleotide sequence comprises a deoptimized AAV Rep inhibitory nucleotide sequence. In a particularly preferred embodiment, the deoptimized AAV Rep inhibitory nucleotide sequence comprises at least a portion of SEQ ID NO:19. In yet another embodiment, the portion of SEQ ID NO:19 comprises SEQ ID NO:09. In some embodiments, the scrambled polynucleotide sequence is operably linked to a promoter.

The invention also provides, an expression vector comprising any one or more of the recombinant nucleotide sequences described herein.

Also provided by the invention is a recombinant adeno-associated virus (rAAV) comprising any one or more of the recombinant nucleotide sequences described herein. In a particular embodiment, the rAAV is infectious, and more preferably (though not necessarily) the infectious rAAV is replication competent. Yet more preferably (though not necessarily) the replication competent rAAV is productive. In one embodiment, the rAAV is produced by a permissive cell at substantially the same copy number as the copy number of a control AAV that lacks expression of AAV Rep protein. In some embodiments, the rAAV is characterized by site-specific integration into adeno-associated virus integration site 1 (AAVS1) sequence. In alternative embodiments, the rAAV expresses at least a functional portion of Rep78 protein SEQ ID NO:04 at a reduced level compared to the level expressed by a control hybrid virus that comprises wild type amino acid sequence SEQ ID NO:20 that is encoded by the wild type AAV Rep inhibitory nucleotide sequence listed as SEQ ID NO:17. In a more preferred embodiment, the rAAV is a hybrid virus that comprises at least a portion of a heterologous virus genome sequence. In some embodiments, the heterologous virus is selected from the group of adenovirus, herpes simplex virus, retrovirus, lentivirus, and baculovirus.

The invention also provides a cell comprising any one or more of the recombinant nucleotide sequences described herein.

Also provided by the invention is a composition comprising any one or more of the recombinant adeno-associated virus (rAAV) described herein, wherein the composition is free of helper virus. In a preferred embodiment, the composition is a vaccine that comprises at least one pharmaceutically acceptable compound selected from the group of diluent, carrier, excipient, and adjuvant.

The invention additionally provides a method for detecting a sequence that reduces replication by a virus, comprising a) providing i) a first expression vector comprising a first nucleotide sequence comprising a scrambled polynucleotide sequence encoding a portion of wild type AAV Rep inhibitory amino acid sequence listed as SEQ ID NO:20, ii) a second expression vector comprising a second nucleotide sequence, wherein the second nucleotide sequence is produced by substituting a portion of the scrambled polynucleotide sequence with a corresponding portion of wild type AAV Rep inhibitory nucleotide sequence listed as SEQ ID NO:17, and iii) a host cell that is permissive for the virus, b) transfecting i) the first expression vector into the permissive cell under conditions to produce a first virus that comprises a first amino acid sequence encoded by the first nucleotide sequence, and ii) the second expression vector into the permissive cell under conditions to produce a second virus that comprises a second amino acid sequence encoded by the second nucleotide sequence, and c) determining the level of replication of the first virus and of the second virus in the transfected permissive cell, wherein a reduced level of replication of the second virus compared to the first virus identifies the portion of wild type AAV Rep inhibitory nucleotide sequence as reducing replication by the virus. In one embodiment, the portion of SEQ ID NO:17 comprises SEQ ID NO:01. In another embodiment, the portion of SEQ ID NO:17 comprises one or more of SEQ ID NO:01, SEQ ID NO:21, SEQ ID NO:24 and SEQ ID NO:27.

The invention also provides a method for detecting a sequence that reduces replication by a virus, comprising a) providing i) a first expression vector comprising a first nucleotide sequence comprising a portion of wild type AAV Rep inhibitory nucleotide sequence listed as SEQ ID NO:17, ii) a second expression vector comprising a second nucleotide sequence, wherein the second nucleotide sequence is produced by substituting the portion of the wild type AAV Rep inhibitory nucleotide sequence with a scrambled polynucleotide sequence encoding the portion of the wild type AAV Rep inhibitory nucleotide sequence, and iii) a host cell that is permissive for the virus, b) transfecting i) the first expression vector into the permissive cell under conditions to produce a first virus that comprises a first amino acid sequence encoded by the first nucleotide sequence, and ii) the second expression vector into the permissive cell under conditions to produce a second virus that comprises a second amino acid sequence encoded by the second nucleotide sequence, and c) determining the level of replication of the first virus and of the second virus in the transfected permissive cell, wherein an increased level of replication of the second virus compared to the first virus identifies the portion of the wild type AAV Rep inhibitory nucleotide sequence as reducing replication by the virus. In one embodiment, the portion of SEQ ID NO:17 comprises SEQ ID NO:01. In a further embodiment, the portion of SEQ ID NO:17 comprises one or more of SEQ ID NO:01, SEQ ID NO:21, SEQ ID NO:24 and SEQ ID NO:27.

Further provided by the invention is a method for producing a recombinant adeno-associated virus (rAAV) particle, comprising a) providing an expression vector comprising any one or more of the recombinant nucleotide sequences described herein, b) providing an adeno-associated virus (AAV) packaging cell, and c) transfecting the packaging cell with the expression vector to produce a recombinant adeno-associated virus (rAAV). In one embodiment, the method further comprises detecting the presence of the produced recombinant adeno-associated virus (rAAV). In another embodiment, the method further comprises isolating the produced recombinant adeno-associated virus (rAAV). In yet a further embodiment, the method does not include transfecting the packaging cell with a helper virus.

The invention also provides a recombinant adeno-associated virus (rAAV) produced by any one or more of the methods described herein.

The invention additionally provides a method for reducing one or more symptoms of disease in a mammalian subject, comprising administering a therapeutically effective amount of any one or more of the vectors described herein to a mammalian subject in need of the therapy. In one embodiment, the method further comprises detecting the presence of at least a portion of the vector in a cell of the treated subject. In an alternative embodiment, the recombinant nucleotide sequence further comprises a heterologous polynucleotide sequence operably linked to a first adeno-associated virus inverted terminal repeat (AAV ITR). In a particular embodiment, the heterologous polynucleotide sequence comprises a therapeutic sequence, exemplified by a therapeutic sequence that encodes one or both of a disease associated polypeptide and an antigen polypeptide. In some embodiments, the therapeutic sequence encodes an antigen polypeptide, and the method further comprises detecting an immune response by the subject to the antigen polypeptide.

The invention also provides a recombinant nucleotide sequence encoding a chimeric protein, a) wherein the encoded chimeric protein i) comprises wild type AAV Rep inhibitory amino acid sequence ii) has Rep-mediated nuclease activity, and b) wherein the recombinant nucleotide sequence comprises a scrambled polynucleotide sequence encoding the wild type AAV Rep inhibitory amino acid sequence. In one embodiment, the wild type AAV Rep inhibitory amino acid sequence comprises and/or consists of SEQ ID NO:22. In another embodiment, the wild type AAV Rep inhibitory amino acid sequence comprises and/or consists of SEQ ID NO:25. In a further embodiment, the wild type AAV Rep inhibitory amino acid sequence comprises and/or consists of SEQ ID NO:28. In one embodiment, the scrambled polynucleotide sequence encoding the wild type SEQ ID NO:22 comprises SEQ ID NO:23. In another embodiment, the scrambled polynucleotide sequence encoding the wild type SEQ ID NO:25 comprises SEQ ID NO:26. In a further embodiment, the scrambled polynucleotide sequence encoding the wild type SEQ ID NO:28 comprises SEQ ID NO:29. In a particular embodiment, the scrambled polynucleotide sequence comprises a deoptimized AAV Rep inhibitory nucleotide sequence.

The invention additionally provides an expression vector comprising any one or more of the recombinant nucleotide sequences disclosed herein.

The invention also provides a recombinant adeno-associated virus (rAAV) comprising any one or more of the recombinant nucleotide sequences disclosed herein. In one embodiment, the rAAV is infectious. In a further embodiment, the infectious rAAV is replication competent. In a particular embodiment, the replication competent rAAV is productive. In yet another embodiment, the rAAV is produced by a permissive cell at substantially the same copy number as the copy number of a control AAV that lacks expression of AAV Rep protein. In a further embodiment, the rAAV is characterized by site-specific integration into adeno-associated virus integration site 1 (AAVS1) sequence. In another embodiment, the rAAV expresses Rep78 protein SEQ ID NO:04 at a reduced level compared to the level expressed by a control hybrid virus that comprises wild type amino acid sequence SEQ ID NO:20 that is encoded by the wild type AAV Rep inhibitory nucleotide sequence listed as SEQ ID NO:17. In another embodiment, the rAAV is a hybrid virus that comprises at least a portion of a heterologous virus genome sequence, exemplified by genomes of adenovirus, herpes simplex virus, retrovirus, lentivirus, and/or baculovirus.

The invention also provides a cell comprising any one or more of the recombinant nucleotide sequences described herein.

Also provided by the invention is a composition comprising any one or more of the recombinant adeno-associated virus (rAAV) described herein, wherein the composition is free of helper virus. In a particular embodiment, the composition is a vaccine that comprises at least one pharmaceutically acceptable compound selected from the group consisting of diluent, carrier, excipient, and adjuvant.

The invention additionally provides a method for producing a recombinant adeno-associated virus (rAAV) particle, comprising a) providing an expression vector comprising any one or more of the recombinant nucleotide sequences described herein, b) providing an adeno-associated virus (AAV) packaging cell, and c) transfecting the packaging cell with the expression vector to produce a recombinant adeno-associated virus (rAAV). In a particular embodiment, the method further comprises detecting the presence of the produced recombinant adeno-associated virus (rAAV). In a further embodiment, the method further comprises isolating the produced recombinant adeno-associated virus (rAAV). In an alternative embodiment, the method does not include transfecting the packaging cell with a helper virus. The invention also provides a recombinant adeno-associated virus (rAAV) produced by the invention's method.

Also provided herein is a method for reducing one or more symptoms of disease in a mammalian subject, comprising administering a therapeutically effective amount of any one or more of the vectors disclosed herein to a mammalian subject in need of the therapy. In one embodiment, the method further comprises detecting the presence of at least a portion of the vector in a cell of the treated subject. In a further embodiment, the recombinant nucleotide sequence further comprises a heterologous polynucleotide sequence operably linked to a first adeno-associated virus inverted terminal repeat (AAV ITR). In yet another embodiment, the heterologous polynucleotide sequence comprises a therapeutic sequence, exemplified by a therapeutic sequence that encodes one or both of a disease associated polypeptide and an antigen polypeptide. In a further embodiment, the therapeutic sequence encodes an antigen polypeptide, and the method further comprises detecting an immune response by the subject to the antigen polypeptide.

BRIEF DESCRIPTION OF THE DRAWINGS

FIG. 1: Analysis of modified Rep78 constructs. a) Comparison of calculated codon pair bias scores of wild-type Rep78, Scrambled Rep 78 and Deoptimized Rep78. b) Western blot for expression levels from flag-tagged wtRep78, Scr Rep78 and Deopt Rep78 ORFs, expressed under a CMV promoter. Levels of GAPDH serve as loading controls. c) Densitometry analysis of Western blot bands for quantification of expression levels was performed using Gel Pro Analyzer 3.0. Levels of Rep expression were normalized to GAPDH levels.

FIG. 2: Functional analyses of genetically recoded Rep 78. (A) Schema of genetic constructs, viruses, and predicted monomeric and dimeric forms resulting from productive Rep 78 cleavage of Ad/AAV/PF4/BDD [based on previously-characterized models [Gnatenko, 2004 #1359; Sandalon, 2000 #1379]]. ψ—adenoviral packaging sequence; pCMV—cytomegalovirus core promoter; Tet—Tetracycline response element/transactivator; pTK—thymidine kinase promoter; IRES-EGFP—internal ribosome entry site with enhanced GFP; Ad-adenovirus bp 3390-3940; BDD—Human B-domain deleted factor VIII (24); pPF4—platelet factor 4 promoter (7); p5IEE (135 bp) and AAV TR (145 bp each plus G-C tail) are also shown. (B) Excision assays were completed by transfecting 293 cells with individual pAd/Rep plasmids, followed by Ad/AAV/PF4/BDD infection (MOI 50), in the presence (+) or absence (−) of doxycycline (1 μg/mL) for evaluation of dimeric (D) or monomeric (M) Ad/AAV/PF4/BDD excision products, generated only with functional Rep 78 endonuclease cleavage at the right TR (9). Southern blots were completed loading 1 μg Hirt DNA/lane, using the ~800 bp DIG labeled PF4/BDD junction fragment as probe. pIM45 is an AAV plasmid expressing wild-type Rep and Cap genes, used as positive control for efficient excision. Faint, low-level excision in the absence of doxycycline is presumably due to "leaky" Rep 78 expression. (C) Excision assays using viral co-infections (MOI 50) were completed in 293 or C12 cells using Ad/sRep or Ad/dRep and Ad/AAV/PF4/BDD, in the presence of dox, 48 hours prior Hirt DNA isolation and Southern blot analysis as outlined above. C12 cells are HeLa-derived stable cell lines that constitutively provide Rep and Cap, used as positive controls. In panels (B) and (C), parent Ad/AAV/PF4/BDD virus is depicted by an asterisk.

FIG. 3: Computational prediction model for Rep inhibitory sequence: (A) Chimeric Rep genes were assembled by polynucleotide domain swaps encompassing discrete ~600 bp segments of wild-type or scrambled sequences, and viability established by adenoviral replication and titering assays in HEK 293 packaging cells (9, 24). Numbers above the schema denote the positions where the chimeric Rep genes were assembled. +/− to the right indicate viability of the resultant adenoviruses. Refer to Table 1 for detailed viral titers. (B) Four distinct Rep chimers each containing 14 discrete (132-135 bp) segments of wild-type or scrambled sequences were synthesized, and Ad replication (viability) was studied in HEK 293 cells (refer to Supplement for nucleotide sequences). Each of the 14 segments has distinct patterns of wild-type or scrambled Rep sequences. Thus the pattern of observed viability uniquely determines the location of the critical signal. Details of the design are described in Skiena & Ward. Note that the columns can be permuted in any of 14! (~$8.7 \times 10^{10}$) orderings with equivalent ability to identify critical sequences, provided it lies completely within one of 14 segments. To minimize the effect of signals on boundaries, columns were ordered to minimize transitions, in effect creating a balanced Gray (binary) code whose distinct genetic signatures and phenotypic growth patterns can be applied for delineation of critical Rep inhibitory sequences (in this case delineated by the *, encompassing Rep sequences bp 1782-1918). (C) Southern blot analysis using Hirt (episomal) DNA isolated at Day 2 or Day 10 post-transfection with the four constructs depicted in FIG. 3B (Ad/Rep I, Ad/Rep II, Ad/Rep III, Ad/Rep IV) with the DNA double digested with DpnI/SbfI and the Southern blot probed using DIG labeled pTG3602 ΔE3 F5/35 DNA.

FIG. 4: (A) Wild type AAV Rep inhibitory nucleotide sequence (SEQ ID NO:01), 135-bp, from AAV2 genome (GenBank accession number AF043303.1) bp 1782 to bp 1916, (B) Wild type AAV Rep inhibitory polypeptide sequence (SEQ ID NO:02) encoded by SEQ ID NO:01, (C) Scrambled AAV Rep inhibitory nucleotide sequence (SEQ ID NO:07), which corresponds to the 135-bp wild type AAV Rep inhibitory nucleotide sequence (SEQ ID NO:01), (D) Deoptimized AAV Rep inhibitory nucleotide sequence (SEQ ID NO:09), which corresponds to the 135-bp wild type AAV Rep inhibitory nucleotide sequence (SEQ ID NO:01), (E) Wild type AAV Rep inhibitory nucleotide sequence SEQ ID NO:17 (564-bp sequence from bp 1623 to bp 2186, of Adeno-Associated Virus 2 (AAV2) genome GenBank: AF043303.1. The 135-bp wild type AAV Rep inhibitory nucleotide sequence (SEQ ID NO:01) is underlined. (F) Wild type AAV Rep inhibitory polypeptide sequence (SEQ ID NO:20) encoded by SEQ ID NO: 17, (G) Scrambled AAV Rep inhibitory nucleotide sequence (SEQ ID NO:18), which corresponds to the 564-bp wild type AAV Rep inhibitory nucleotide sequence SEQ ID NO:17, and (H) Deoptimized AAV Rep inhibitory nucleotide sequence (SEQ ID NO:19), which corresponds to the 564-bp wild type AAV Rep inhibitory nucleotide sequence SEQ ID NO:17.

FIG. 5: Nucleotide sequence (SEQ ID NO:03) encoding an exemplary wild type AAV2 Rep78. A portion of the Rep68 sequence lies within the Rep78 sequence from bp 321 to bp 1906 of the AAV2 genome). The 3' end the Rep68 sequence lies downstream of the Rep78 stop codon. The sequence common to Rep68 and Rep78 is underlined. The inhibitory sequence (bp 1782 to bp 1916 of the AAV2 genome). The nucleotide sequence (SEQ ID NO:01) of the exemplary 135-bp wild type AAV Rep inhibitory nucleotide sequence, from bp 1782 to bp 1916 of the AAV2 genome, is in italics.

FIG. 6: (A) Amino acid sequence (SEQ ID NO:04) of AAV wild type Rep78 protein (GenBank protein_id="AAC03775.1, db_xref="GI:2906018. (B) Amino acid sequence (SEQ ID NO:05) of AAV wild type Rep68 protein (GenBank protein_id="AAC03774.1, db_xref="GI:2906017.

FIG. 7: (A) Scrambled AAV Rep78 nucleotide sequence sRep78 (SEQ ID NO:06). Sequence of the exemplary scrambled AAV Rep inhibitory nucleotide sequence (SEQ ID NO:07), which corresponds to the 135-bp wild type AAV Rep inhibitory nucleotide sequence (SEQ ID NO:01) is in italics. (B) Deoptimized AAV Rep78 nucleotide sequence dRep78 (SEQ ID NO:08). Sequence of the exemplary deoptimized AAV Rep inhibitory nucleotide sequence (SEQ ID NO:09), which corresponds to the 135-bp wild type AAV Rep inhibitory nucleotide sequence (SEQ ID NO:01) is in italics.

FIG. 12: Nucleotide sequence (SEQ ID NO:16) of the wild type complete genome of Adeno-Associated Virus 2 (AAV2), GenBank: AF043303.1, containing wild type AAV Rep inhibitory nucleotide sequence SEQ ID NO:17 (564-bp sequence from bp 1623 to bp 2186, shown in underlined bold text), which in turn contains wild type AAV Rep inhibitory nucleotide sequence SEQ ID NO:01 (135-bp sequence from bp 1782 to bp 1916, shown in underlined bold, italicized text).

FIG. 13: Alignments of wild-type (WT), deoptimized (d), and scrambled (s) AAV Rep. Nucleotides identical to all three sequences are delineated by *. Alignments of the 1,866 base pair re-coded Rep genomic sequences were completed and displayed using Clustal 2.1 multiple sequence alignment tool, numbered relative to the full-length 4,679 bp AAV2 genome (Gen Bank Accession number AF043303.1, SEQ ID NO: 16 of FIG. 12); the circle (−) delineates the initiator MET starting at bp 321; the p19 (bp 843 to 849) and p40 (bp 1,823 to 1,827) promoter TATA sequences, and the 5'-Rep 68/40 alternative splice site (bp 1,907 to 1,908) are highlighted in a grey box. The wild type AAV Rep inhibitory nucleotide sequence SEQ 1D NO:17 (from bp 1623 to bp 2186) is shown in underlined bold text, and contains the wild type AAV Rep inhibitory nucleotide sequence SEQ ID NO:01 (135-bp long, from bp 1782 to bp 1916, shown in underlined bold, italicized text). The previously-characterized p40 promoter transcription binding sites for GGT, SP1, and AP1 are boxed; the transcription start site is delineated by an arrow.

FIG. 15. Rep78 nucleotide and amino acid sequences. A. Segment 11: bp 1647-1781 of GenBank accession number AF043303.1: Wild type nucleotide sequence (SEQ ID NO:21), Wild type amino acid sequence (SEQ ID NO:22), Scrambled nucleotide sequence (SEQ ID NO:23). B. Segment 13: bp 1917-2051 of GenBank accession number AF043303.1: Wild type nucleotide sequence (SEQ ID NO:24), Wild type amino acid sequence (SEQ ID NO:25), Scrambled nucleotide sequence (SEQ ID NO:26). C. Segment 14: bp 2052-2186 of GenBank accession number AF043303.1: Wild type nucleotide sequence (SEQ ID NO:27), Wild type amino acid sequence (SEQ ID NO:28), Scrambled nucleotide sequence (SEQ ID NO:29). D. Segment 12: 135 bp sequence: bp1782-1916 of GenBank accession number AF043303.1: Wild type nucleotide sequence (SEQ ID NO:01), Wild type amino acid sequence (SEQ ID NO:02), Scrambled nucleotide sequence (SEQ ID NO:07).

FIG. 16. Polynucleotide sequences encoding wild type AAV Rep inhibitory amino acid sequence. A. Segment 11 scrambled nucleotide sequence (SEQ ID NO:23). B. Segment 13 scrambled nucleotide sequence (SEQ ID NO:26). C. Segment 14 scrambled nucleotide sequence (SEQ ID NO:29). D. Segment 12 scrambled 135 bp nucleotide sequence (SEQ ID NO:07).

DEFINITIONS

Figure 8:
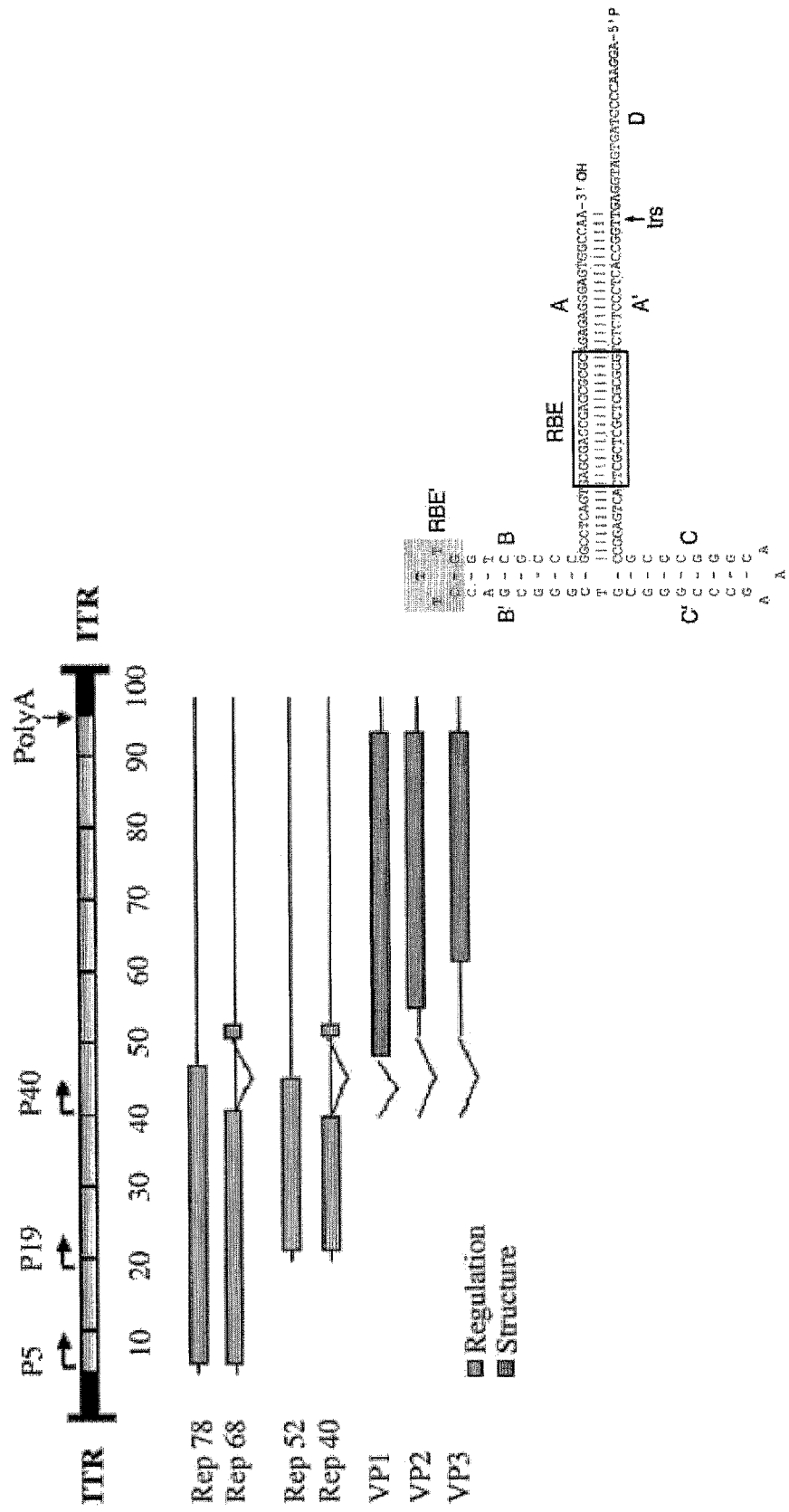
FIG. 8: Genome organization of AAV (Merten-O-W et al. 2005:12:S51-61).

To facilitate understanding of the invention, a number of terms are defined below. Further definitions appear throughout the text.

The term "recombinant" nucleotide sequence refers to a nucleotide sequence that is produced by means of molecular biological techniques (e.g., cloning, enzyme restriction and/or ligation steps) and/or chemical synthesis.

"Recombinant protein" or "recombinant polypeptide" refers to a protein molecule that is expressed using a recombinant nucleotide sequence.

"Recombinant mutation" refers to a mutation that is introduced by means of molecular biological techniques. This is in contrast to mutations that occur in nature.

"Recombinant virus" refers to a virus that contains a recombinant nucleotide sequence, recombinant polypeptide, and/or recombinant mutation, as well as progeny of that virus.

"Endogenous," "wild type," "wildtype," "wt" and "wild-type" when in reference to a sequence (e.g., that is introduced into a cell and/or virus) refer to the sequence as it occurs in nature (e.g., in the cell and/or virus). It is now appreciated that most or all gene loci exist in a variety of allelic forms, which vary in frequency throughout the geographic range of a species. Thus, in one embodiment, a "wild type" sequence is the sequence that occurs at the highest frequency in nature.

The term "heterologous" when in reference to a sequence (e.g., that is introduced into a cell and/or virus) refers to a sequence that is not endogenous (to the cell and/or virus into which it is introduced). For example, a "heterologous" gene refers to a gene that is not in its natural environment (in other words, has been altered by the hand of man). For example, a heterologous gene includes a gene from one species introduced into another species. A heterologous gene also includes a gene native to an organism that has been altered in some way (for example, mutated, added in multiple copies, linked to a non-native promoter or enhancer sequence, etc.). Heterologous genes may comprise cDNA forms of a gene; the cDNA sequences may be expressed in either a sense (to produce mRNA) or anti-sense orientation (to produce an anti-sense RNA transcript that is complementary to the mRNA transcript). Heterologous genes are distinguished from endogenous genes in that the heterologous gene sequences are typically joined to nucleotide sequences comprising regulatory elements such as promoters that are not found naturally associated with the gene for the protein encoded by the heterologous gene or with gene sequences in the chromosome, or are associated with portions of the chromosome not found in nature (for example, genes expressed in loci where the gene is not normally expressed).

The term "operably linked" when in reference to the relationship between nucleic acid sequences and/or amino acid sequences refers to linking the sequences such that they perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest and/or the synthesis of a polypeptide encoded by the nucleotide sequence of interest. Similarly, operably linking AAV terminal repeats (TRs) to a nucleotide sequence of interest means that the sequences are linked in such a way such that the AAV TRs are capable of directing replication of the nucleotide sequence of interest. Also, operably linking an AAV packaging sequence to a nucleotide sequence of interest refers to linkage of these sequences such that the AAV packaging sequence is capable of directing packaging of the nucleotide sequence of interest into an encapsidated virion.

"Portion" and "fragment" when made in reference to a nucleic acid sequence or protein sequence refer to a piece of that sequence that may range in size from two (2) contiguous nucleotides and amino acids, respectively, to the entire sequence minus one nucleotide and amino acid, respectively. Thus, "at least a portion of" a nucleic acid sequence or protein sequence refers to a piece of that sequence that may range in size from two (2) contiguous nucleotides and amino acids, respectively, to the entire sequence. For example, "at least a portion of the 135-base pair wild type AAV Rep inhibitory amino acid sequence listed as SEQ ID NO:02" refers to a sequence that ranges in size from any numerical value from 2 to 135 contiguous base-pairs, such as 2, 3, 4, 6, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 120, 121, 122, 123, 124, 125, 126, 127, 128, 129, 130, 131, 132, 133, 134, and 135 contiguous base-pairs. Similarly, "at least a portion of the 564-base pair wild type AAV Rep inhibitory amino acid sequence listed as SEQ ID NO:20" refers to a sequence that ranges in size from any numerical value from 2 to 564 contiguous base-pairs, such as from 2 to 50, from 2 to 100, from 2 to 150, from 2 to 200, from 2 to 200, from 2 to 250, from 2 to 300, from 2 to 350, from 2 to 400, from 2 to 450, from 2 to 500, and from 2 to 564 contiguous base-pairs.

A "functional" portion of a sequence (e.g., polypeptide or polynucleotide sequence) refers to a portion of the sequence that has one or more activities (e.g., enzyme activity, biochemical activity, etc.) of the full-length sequence. For example, a functional portion of a promoter refers to a nucleic acid sequence that is capable of binding to RNA polymerase to initiate transcription of an operably linked oligonucleotide sequence into mRNA. In another example, a functional portion of Rep78 protein refers to a portion of Rep78 that functions in cleaving a folded AAV ITR. Methods for determining this function are known in the art and described herein (Example 3).

"Chimeric," "fusion" and "hybrid" composition (e.g., when in reference to an amino acid sequence, nucleotide sequence, virus, cell, etc.) refers to a composition containing parts from different origins. In one embodiment, the parts may be from different organisms, different tissues, different cells, different viruses, etc. In another embodiment, the parts may be from different proteins and/or genomic sequences from the same organism, same tissue, same cell, same virus, etc.

The terms "mutation" and "modification" refer to a deletion, insertion, or substitution. A "deletion" is defined as a change in a nucleic acid sequence or amino acid sequence in which one or more nucleotides or amino acids, respectively, is absent. An "insertion" or "addition" is that change in a nucleic acid sequence or amino acid sequence that has resulted in the addition of one or more nucleotides or amino acids, respectively. A "substitution" in a nucleic acid sequence or an amino acid sequence results from the replacement of one or more nucleotides or amino acids, respectively, by a molecule that is a different molecule from the replaced one or more nucleotides or amino acids. For example, a nucleic acid may be replaced by a different nucleic acid as exemplified by replacement of a thymine by a cytosine, adenine, guanine, or uridine. Alternatively, a nucleic acid may be replaced by a modified nucleic acid as exemplified by replacement of a thymine by thymine glycol. Substitution of an amino acid may be conservative or non-conservative. "Conservative substitution" of an amino acid refers to the replacement of that amino acid with another amino acid that has a similar hydrophobicity, polarity, and/or structure. For example, the following aliphatic amino acids with neutral side chains may be conservatively substituted one for the other: glycine, alanine, valine, leucine, isoleucine, serine, and threonine. Aromatic amino acids with neutral side chains that may be conservatively substituted one for the other include phenylalanine, tyrosine, and tryptophan. Cysteine and methionine are sulphur-containing amino acids that may be conservatively substituted one for the other. Also, asparagine may be conservatively substituted for glutamine, and vice versa, since both amino acids are amides of dicarboxylic amino acids. In addition, aspartic acid (aspartate) may be conservatively substituted for glutamic acid (glutamate) as both are acidic, charged (hydrophilic) amino acids. Also, lysine, arginine, and histidine may be conservatively substituted one for the other since each is a basic, charged (hydrophilic) amino acid. "Non-conservative substitution" is a substitution other than a conservative substitution. Guidance in determining which and how many amino acid residues may be substituted, inserted or deleted without abolishing biological and/or immunological activity may be found using computer programs well known in the art, for example, DNAStar™ software.

A "variant" or "homolog" of a polypeptide sequence of interest or nucleotide sequence of interest refers to a sequence that has identity of at least 65% with the an amino acid sequence of interest or nucleotide sequence of interest, including identity of at least 90%, at least 91%, at least 92%, at least 93%, at least 94%, at least 95%, at least 96%, at least 97%, at least 98%, and/or at least 99%. Thus, homologous genomic nucleotide sequences within the scope of the invention include orthologs and paralogs. The term "ortholog" refers to a gene in different species that evolved from a common ancestral gene by speciation. In some embodiments, orthologs retain the same function. The term "paralog" refers to genes related by duplication within a genome. In some embodiments, paralogs evolve new functions. In further embodiments, a new function of a paralog is related to the original function. Variants of a polypeptide sequence of interest may contain a mutation.

"Identity" when in reference to 2 or more sequences (e.g., 2 DNA sequences, 2 RNA sequences, and/or 2 protein sequences) refers to the degree of similarity of the 2 or more sequences, and is generally expressed as a percentage. Identity in amino acid or nucleotide sequences can be determined using Karlin and Altschul's BLAST algorithm (Proc. Natl. Acad. Sci. USA, 1990, 87, 2264-2268; Karlin, S. & Altschul, S F., Proc. Natl. Acad. Sci. USA, 1993, 90, 5873). Programs called BLASTN and BLASTX have been developed using the BLAST algorithm as a base (Altschul, S F. et al., J. Mol. Biol., 1990, 215, 403). When using BLASTN to analyze nucleotide sequences, the parameters can be set at, for example, score=100 and word length=12. In addition, when using BLASTX to analyze amino acid sequences, the parameters can be set at, for example, score=50 and word length=3. When using BLAST and the Gapped BLAST program, the default parameters for each program are used. Specific techniques for these analysis methods are the well known, e.g., on the website of the National Center for Biotechnology Information.

The term "corresponding" when in reference to the position of a first amino acid in a first polypeptide sequence as compared to a second amino acid in a second polypeptide sequence means that the positions of the first and second amino acids are aligned when the first and second amino acid sequences are aligned. Software for alignment of amino acid sequences and of nucleotide sequences is known in the art such as BLAST, FASTA, HMMER, IDF, SAM, and SSEARCH (for both amino acid sequences and nucleotide sequences), Infernal (for RNA sequences), CS-BLAST, HHpred, HHsearch, and PSI-BLAST (for amino acid sequences).

"Codon" refers to a specific sequence of three adjacent nucleotides on a strand of DNA or RNA that specifies the genetic code information for synthesizing a particular amino acid.

"Codon pair" and "codon-pair" interchangeably refer to two codons that are separated by less than 6 intervening nucleotides, i.e., separated by less than two intervening codons.

"Synonymous codon" when used to describe a first codon as compared to a reference codon, refers to a first codon that differs in nucleotide sequence from the reference codon and that encodes the same amino acid. Due to the degeneracy of the codon table, 18 of the 20 amino acids can be encoded using more than one codon. Synonymous codons differ from one another often at the third base of the codon (the wobble position). Thus the same polypeptide sequence can be encoded by different nucleotide sequences that vary from one another by an amount equal to or less than 33% (i.e., the nucleotide sequences have more than 67% identity).

"Synonymous codon pair" when used to describe a first codon pair as compared to a reference codon pair, refers to a first codon pair containing at least one synonymous codon compared to the corresponding codon in the reference codon pair. Thus, in one embodiment, a synonymous codon pair contains one synonymous codon compared to the corresponding codon in the reference codon pair. In another embodiment, both codons in the synonymous codon pair are synonymous codons compared to the corresponding codons in the reference codon pair.

"Codon bias" refers to the presence of a different (higher or lower) frequency of using one synonymous codon than another synonymous codon to encode the same amino acid. For instance, in humans, the Ala codon GCC is used four times as frequently as the synonymous codon GCG (Coleman et al. (2008)). An "underrepresented codon" refers to a codon that occurs at a lower frequency compared with random frequency for that codon. In contrast, an "overrepresented codon" refers to a codon that occurs at a higher frequency compared with random frequency for that codon.

"Codon pair bias" refers to the presence of a different (higher or lower) frequency of using a codon-pair compared with random frequency for that codon-pair (Gutman et al. (1989)). Thus, in one embodiment, codon pair bias refers to the preference (i.e., (higher or lower) frequency) for some codon pairs over other synonymous codons to encode the same pair of adjacent amino acids. Synonymous codons can be paired in multiple ways to encode the same 2 adjacent amino acids. However, in nature a strong codon pair bias is found to exist, resulting in the disproportionate representation of some codon pairs over others (Gutman et al. (1989) Nonrandom utilization of codon pairs in *Escherichia coli*. *Proc. Natl. Acad. Sci. U.S.A.* 86(10):3699-3703). This codon pair bias is independent of codon frequency and is found to affect translation rates. Codon pair bias includes underrepresentation of a codon pair, and overrepresentation of a codon pair. An "underrepresented codon pair" refers to a codon pair that occurs at a lower frequency compared with random frequency for that codon-pair. In contrast, an "overrepresented codon pair" refers to a codon pair that occurs at a higher frequency compared with random frequency for that codon-pair. For example, the amino acid pair Ala-Glu is expected to be randomly encoded by the codon pair GCCGAA and the codon pair GCAGAG about equally often. However, the codon pair GCCGAA is underrepresented such that it is used only one-seventh as often as the codon pair GCAGAG.

"Scrambled nucleotide sequence" and "Scr nucleotide sequence" when describing a first nucleotide sequence as compared to a reference nucleotide sequence (e.g., a reference wild type AAV Rep inhibitory nucleotide sequence listed as SEQ ID NO:17 or SEQ ID NO:01) interchangeably refer to a first nucleotide sequence that contains one or more synonymous codons and/or one or more synonymous codon-pairs, and that encodes the same amino acid sequence that is encoded by the reference nucleotide sequence. The prior art provides algorithm for scrambling nucleotide sequences using synonymous codons without altering the encoded amino acid sequence (Coleman et al. (2008) Science 320(5884):1784-1787) (Example 2). Thus, a "codon-scrambled nucleotide sequence" refers to a first nucleotide sequence that contains one or more synonymous codons compared to a reference nucleotide sequence, and that encodes the same amino acid sequence that is encoded by the reference nucleotide sequence. A "codon-pair-scrambled nucleotide sequence" refers to a first nucleotide sequence that contains one or more synonymous codon-pairs compared to a reference nucleotide sequence, and that encodes the same amino acid sequence that is encoded by the reference nucleotide sequence. In one embodiment, the synonymous codons and/or codon-pairs are randomly mixed. In another embodiment, from 50% to 100% of the codons and/or codon-pairs of a scrambled nucleotide sequence is synonymous to the codons and/or codon-pairs, respectively, of the reference sequence, including, for example, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100% synonymous codons and/or synonymous codon-pairs, respectively. In one preferred embodiment, 100% of the codons and/or codon-pairs of a scrambled nucleotide sequence is synonymous to the codons and/or codon-pairs, respectively, of the reference sequence. Thus, in one embodiment in which 100% of the codons and/or 100% of the codon-pairs of a scrambled nucleotide sequence is synonymous to the codons and/or codon-pairs of a reference sequence, respectively, then the scrambled nucleotide sequence differs from the reference sequence by an amount equal to or less than 33%, i.e., the scrambled nucleotide sequence has more than 67% identity to the reference sequence. For example, the invention provides a "scrambled AAV Rep inhibitory nucleotide sequence listed as SEQ ID NO:18 (FIG. 4G) and/or SEQ ID NO:07" (FIG. 4, panel C, and FIG. 7, panel A) also referred to as a "scrambled polynucleotide sequence encoding wild type AAV Rep inhibitory amino acid sequence listed as SEQ ID NO:20 (FIG. 4F) and/or SEQ ID NO:02," (FIG. 4 panel B) wherein the reference nucleotide sequence is the wild type AAV Rep inhibitory nucleotide sequence listed as SEQ ID NO:17 (FIG. 4E, FIG. 12, FIG. 13) and/or SEQ ID NO:01 (FIG. 4 panel A, FIG. 12, FIG. 13). In one embodiment, the level of protein expression by the scrambled nucleotide sequence is substantially the same as the level of expression by the reference nucleotide sequence and/or is approximately twice the level of expression by a deoptimized nucleotide sequence (As illustrated, without limitation in Example 2). Generic methods (e.g., algorithms) for generating a scrambled nucleotide sequence by modifying a reference nucleotide sequence without modifying the encoded amino acid sequence are know in the art (Coleman J R, et al. (2008).

A "deoptimized nucleotide sequence" when describing a first nucleotide sequence as compared to a reference nucleotide sequence (e.g., a reference wild type AAV Rep inhibitory nucleotide sequence listed as SEQ ID NO:17 or SEQ ID NO:01) means a scrambled first nucleotide sequence that contains one or more underrepresented codons and/or one or more underrepresented codon-pairs (see for Example FIG. 1a), and that encodes the same amino acid sequence that is encoded by the reference nucleotide sequence. Thus, a "codon-deoptimized nucleotide sequence" refers to a first nucleotide sequence that contains one or more deoptimized codons compared to a reference nucleotide sequence, and that encodes the same amino acid sequence that is encoded by the reference nucleotide sequence. A "codon-pair-deoptimized nucleotide sequence" refers to a first nucleotide sequence that contains one or more deoptimized codon-pairs compared to a reference nucleotide sequence, and that encodes the same amino acid sequence that is encoded by the reference nucleotide sequence. In a further embodiment, from 50% to 100% of the codons and/or codon-pairs of a deoptimized nucleotide sequence is deoptimized as compared to the codons and/or codon-pairs, respectively, of the reference sequence, including, for example, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100% deoptimized codons and/or deoptimized codon-pairs, respectively. In one embodiment, 100% of the codons and/or codon-pairs of a deoptimized nucleotide sequence are underrepresented codons and/or codon-pairs compared to the codons and/or codon pairs, respectively, of the reference sequence. In one embodiment, utilization of underrepresented codons and/or codon pairs in a deoptimized nucleotide sequence results in a lower level of expression of the deoptimized nucleotide sequence compared to the level of expression of a scrambled nucleotide sequence and/or of a control wild type sequence, due to inefficient translation. For example, data herein show that the level of Rep78 protein expression by the scrambled Rep78 nucleotide sequence is substantially [OK defined] the same as the level of expression by the reference wild type Rep78 nucleotide sequence, and approximately twice the level of expression by a deoptimized Rep78 nucleotide sequence (see Example 2, FIG. 1*b*). Confirmation of the reduced protein expression by a deoptimized nucleotide sequence may be determined using methods known in the art (e.g., immunoblot analysis, Example 2). In one embodiment, the invention provides a "deoptimized AAV Rep inhibitory nucleotide sequence" that comprises SEQ ID NO:19 (FIG. 4H) and/or SEQ ID NO:09 (FIG. 4 panel D, FIG. 7 panel B), and that encodes wild type AAV Rep inhibitory amino acid sequence listed as SEQ ID NO:20 (FIG. 4F) and/or SEQ ID NO:02 (FIG. 4 panel B).

The terms "lack" and "lacking" a nucleotide sequence when made in reference to a vector means that the vector contains at least one deletion (i.e., absence of one or more nucleotides) in the nucleotide sequence. Deletions may be continuous (i.e., uninterrupted) or discontinuous (i.e., interrupted). Deletions may lie in a coding sequence or a regulatory sequence. A deletion can be a partial deletion (i.e., involving removal of a portion ranging in size from one (1) nucleotide residue to the entire nucleic acid sequence minus one nucleic acid residue) or a total deletion of the nucleotide sequence. Deletions are preferred which prevent the production of at least one expression product encoded by the nucleotide sequence. For example, a vector that lacks adenovirus E1 gene region refers to a vector that contains at least one deletion in the E1 gene region. Preferably, though not necessarily, the deletion prevents the production of at least one of the multiple proteins encoded by the E1 gene region.

"Virus" refers to an obligate, ultramicroscopic, intracellular parasite particle of nucleic acid sequence (DNA or RNA) that is assembled inside a polypeptide shell, and that is incapable of autonomous replication (i.e., replication requires the use of a host cell's machinery).

"Helper virus" refers to a virus that is replication-competent and/or productive and/or infectious in a particular host cell (e.g., the host cell may provide virus gene products such as adenovirus E1 proteins for a helper adenovirus that is replication-competent). For example, a replication-competent and/or productive and/or infectious first virus (i.e., helper virus) is used to supply, in trans, functions (e.g., proteins) that are lacking in a second virus that is replication-incompetent and/or non-productive and/or non-infectious. Thus, the first virus is the to "help" the second virus thereby permitting the replication by and/or production of and/or infection by the second viral genome in the cell containing both the first helper virus and the second viruses.

The terms "free of helper virus" and "free of contamination with helper virus" when in reference to a sample, mean that the number of helper virus particles in the sample is from zero % to 1%, more preferably from zero % to 0.5%, and most preferably from zero % to 0.05%, when compared to the number of particles of a second virus in the same sample.

The term "replication" of a virus includes, but is not limited to, the steps of adsorbing (e.g., receptor binding) to a cell, entry into a cell (such as by endocytosis), introducing its genome sequence into the cell, un-coating the viral genome, initiating transcription of viral genomic sequences, directing expression of viral encapsidation proteins, encapsidating of the replicated viral nucleic acid sequence with the encapsidation proteins into a viral particle that is released from the cell to infect other cells that are of a permissive and/or susceptible character. A virus may be infectious (i.e., can penetrate a cell) without being replication competent (i.e., fails to release virions from the infected cell).

"Replication competent" when in reference to a viral vector and/or virus means capable of adsorbing (e.g., receptor binding) to a cell, entry into a cell (such as by endocytosis), introducing its genome sequence into the cell, uncoating the viral genome, initiating transcription of viral genomic sequences, directing expression of viral encapsidation proteins, encapsidating of the replicated viral nucleic acid sequence with the encapsidation proteins into new progeny virus particles.

"Replication incompetent," "replication defective," "replication attenuated" are used interchangeably to refer to a virus and/or viral vector that has a reduced level of replication compared to wild type virus and/or to a viral vector containing wild type virus nucleotide sequences. Replication incompetent also means a virus particle that is substantially incapable of completing one or more of the steps of replication. Methods for producing replication incompetent adenoviral vectors are known in the art (e.g., U.S. Pat. No. 7,300,657 to Pau, U.S. Pat. No. 7,468,181 to Vogels, U.S. Pat. No. 6,136,594 to Dalemans, U.S. Pat. No. 5,994,132 to Chamberlain et al., U.S. Pat. No. 6,797,265 to Amalfitano et al., U.S. Pat. No. 7,563,617 to Hearing et al., and U.S. Pat. No. 6,262,035 to Campbell et al.). For example, in one embodiment, a replication incompetent adenovirus and/or adenoviral vector (a) lacks (i.e., has a deletion of) adenovirus E1 gene coding sequence, (b) lacks adenovirus E1 gene coding sequence and E2b gene coding sequence (c) lacks adenovirus E1 gene coding sequence and adenovirus E4 gene coding sequence, (d) lacks adenovirus E1 gene coding sequence and adenovirus E2a gene coding sequence, and/or (e) lacks adenovirus E1 gene coding sequence and adenovirus EIVa2 gene coding sequence.

"Infection" and "infectious" when in reference to a virus refer to adsorption of the virus to the cell and penetration into the cell. A virus may be infectious (i.e., can adsorb to and penetrate a cell) without being replication competent (i.e., fails to produce new progeny virus particles). Data herein demonstrate productive infection that generated infectious virus that is replication competent, using clone pAd/sRep78 (containing a scrambled Rep78 sequence) and clone pAd/dRep78 (containing a deoptimized Rep78 sequence), that formed CPE in transfected HEK 293 packaging cells (Example 3).

A "non-infectious" and "uninfectious" virus is a virus that is incapable of adsorption to, and/or penetration into, a cell.

"Productive" virus is a replication competent virus that is capable of a "productive infection," i.e., wherein the replication competent virus produces new progeny virus particles that are released extracellularly. Productive infection by a productive virus may be detected by detection of CPE. Data herein demonstrate productive infection that generated infectious virus that is replication competent, using clone pAd/sRep78 (containing a scrambled Rep78 sequence (SEQ ID NO:06 of FIG. 7 panel A)) and clone pAd/dRep78 (containing a deoptimized Rep78 sequence (SEQ ID NO:08 of FIG. 7 panel B)), that formed CPE in transfected HEK 293 packaging cells (Example 3).

"Non-productive" virus is a replication competent virus that produces a "non-productive infection," i.e., wherein the replication competent virus produces new progeny virus particles that are not released from the infected cell. This includes scenarios where the viral genome is integrated into the host cell genome. Non-productive infection by a non-productive virus may be detected by detecting virus proteins and/or nucleic acids in cellular extracts, in the absence of CPE.

"Encapsidated" when made in reference to a nucleotide sequence refers to a nucleotide sequence that is packaged inside a protein envelope to form a particle. Data presented herein demonstrates that the invention's nucleotide sequence vectors were packaged efficiently into stable virus particles. Encapsidated vectors of the invention may be recovered following transfection or infection of target cells using methods known in the art. When used herein, "recovering" encapsidated vectors refers to the collection of the vectors by, for example, lysis of the cell (e.g., freeze-thawing) and removing the cell debris by pelleting, and/or collection of extracellular solutions.

The terms "cytopathic effect" and "CPE" as used herein describe changes in cellular structure (i.e., a pathologic effect). Common cytopathic effects include cell destruction, syncytia (i.e., fused giant cells) formation, cell rounding, vacuole formation, and formation of inclusion bodies. CPE results from actions of a virus on permissive cells that negatively affect the ability of the permissive cellular host to perform its required functions to remain viable. In in vitro cell culture systems, CPE is evident when cells, as part of a confluent monolayer, show regions of non-confluence after contact with a specimen that contains a virus. The observed microscopic effect is generally focal in nature and the foci are initiated by a single virion. However, depending upon viral load in the sample, CPE may be observed throughout the monolayer after a sufficient period of incubation. Cells demonstrating viral induced CPE usually change morphology to a rounded shape, and over a prolonged period of time can die and be released from their anchorage points in the monolayer. When many cells reach the point of focal destruction, the area is called a viral plaque, which appears as a hole in the monolayer. The terms "plaque" and "focus of viral infection" refer to a defined area of CPE which is usually the result of infection of the cell monolayer with a single infectious virus which then replicates and spreads to adjacent cells of the monolayer. Cytopathic effects are readily discernible and distinguishable by those skilled in the art. Data herein demonstrate productive infection that generated infectious virus that is replication competent, using clone pAd/sRep78 (containing a scrambled Rep78 sequence) and clone pAd/dRep78 (containing a deoptimized Rep78 sequence), that formed CPE in transfected HEK 293 packaging cells (Example 3).

"Integration" of a first nucleotide sequence (e.g., a transgene) into a second nucleotide sequence (e.g., a genome) refers to the insertion of the first nucleotide sequence at one or more locations (referred to as "integration sites") within the second nucleotide sequence following contacting the first and second nucleotide sequences. "Efficiency of integration" refers to the number of inserted first nucleotide sequences relative to the number of first nucleotide sequences that were contacted with the second nucleotide sequence. Methods for determining efficiency of integration are known in the art (McCarty et al. (2004) *Annual Review of Genetics* 38:819-844), including quantitative real-time PCR assays (Huser et al. (2002) *J. Virol.* 76:7554).

"Site-specific integration" and "SSI" refer to the insertion of the first nucleotide sequence occurs at one or more particular locations ("integration sites") in the second nucleotide sequence. In one embodiment, site-specific integration of a transgene into chromosome 19 AAVS1 sites may be effected by using Rep68/78 proteins in trans to the transgene and an "Rep Binding Element" ("RBE") in cis (Feng et al. (2006) A 16 bp Rep Binding Element is Sufficient for Mediating Rep-dependent Integration into AAVS1. *Journal of Molecular Biology:* 1-8). This RBE can be found either within the AAV Terminal Repeat or the p5 Integration Efficiency Element (p5IEE). Thus, for example, site-specific integration of a transgene into chromosome 19 AAVS1 sites may be effected by using the AAV ITR or IEE in cis to the transgene, and the Rep68/78 protein in trans Thus, in one particular embodiment, site-specific integration into the AAVS1 sites may be accomplished using an AAV ITR flanked transgene and the Rep protein in trans (McLaughlin et al. (1988) Adeno-associated virus general transduction vectors: analysis of proviral structure. *J. Virol.* 62:1963-1973). In another embodiment, site-specific integration into the AAVS1 sites may be accomplished using the IEE in cis to the transgene, and the Rep protein in trans (Philpott et al. (2002) A p5 integration efficiency element mediates Rep-dependent integration into AAVS1 at chromosome 19. *Proc. Natl. Acad. Sci. USA* 99:12381).

"RSSSI" and "Rep mediated site-specific integration" interchangeably refer to site-specific integration that requires the activity of AAV Rep protein. Site-specific integration with wt AAV particles has been found to be highly specific in multiple cell lines, with one study finding 94% of all AAV positive IB3-1 cells to have site-specific integration into Chromosome 19.

"AAVS1" and "adeno-associated virus integration site 1" sequence interchangeably refer to the well-characterized sequence on the q arm of chromosome 19 (19q13.3qter). (Wang et al. (2006) *Journal of Virology* 80(23):11699-11709; McLaughlin et al. (1990) *Proc. Natl. Acad. Sci. USA* 87, 2211-2215; Samulski et al. (1991) *EMBO J.* 10, 3941-3950; Giraud et al. (1994) *Proc. Natl. Acad. Sci. USA* 91, 10039-10043; Kearns et al. (1996) *Gene Ther.* 3, 748-755).

Figure 11:
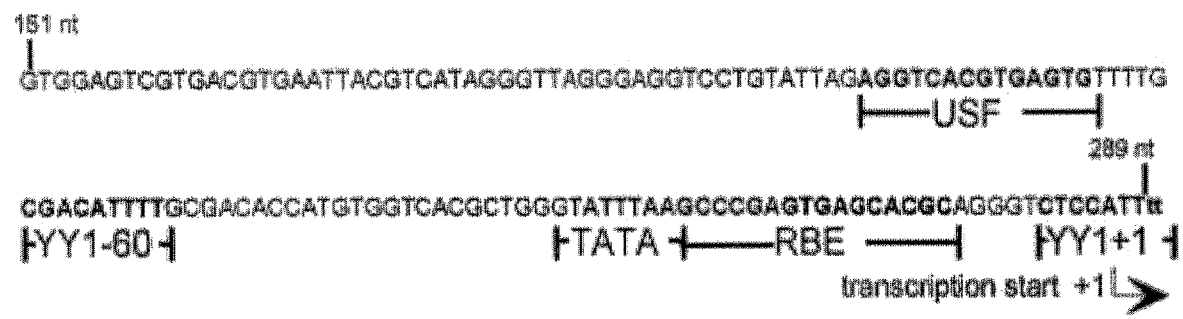
FIG. 11: Schematic representation of the 138-nt IEE (SEQ ID NO:11) showing YY1 and Rep-binding sites, a putative upstream stimulating factor (USF)-binding site, and a TATA box (Philpott et al. (2002) A p5 integration efficiency element mediates Rep dependent integration into AAVS1 at chromosome 19. *Proc. Natl. Acad. Sci. USA* 99:12381).

"AAV p5TEE" and "AAV p5 integration efficiency element" refer to the AAV sequence that is active in cis to a transgene for bringing about site-specific integration of the transgene into the chromosome 19 AAVS1 sequence, in the presence of the AAV Rep68/78 protein in trans to the transgene. "AAV p5IEE" is exemplified by the 138-nt IEE (SEQ ID NO:11) (FIG. 11) (Philpott et al. (2002) *Proc. Natl. Acad. Sci. USA* 99:12381).

"Gene therapy" refers to reducing one or more clinical and/or sub-clinical symptoms of disease in a subject by insertion of nucleotide sequences into the subject's cells to replace damaged or abnormal genes with normal ones, and/or to provide new genetic instructions to help fight disease. Viruses are used as gene delivery vectors, as exemplified by vectors using sequences from adenovirus, adeno-associated virus, herpes simplex virus, retrovirus, lentivirus, baculovirus, etc., as described herein.

The term "control" as used herein when in reference to a sample (e.g., cell, tissue, animal, virus, etc.) refers to any type of sample that one of ordinary skill in the art may use for comparing to a test sample (e.g., cell, tissue, animal, virus, etc.) by maintaining the same conditions in the control and test samples, except in one or more particular factors. In one embodiment, the comparison of the control and test samples is used to infer a causal significance of this varied one or more factors.

A "subject" that may benefit from the invention's methods includes any multicellular animal, preferably a mammal. Mammalian subjects include humans, non-human primates, murines, ovines, bovines, ruminants, lagomorphs, porcines, caprines, equines, canines, felines, ayes, etc.). Thus, mammalian subjects are exemplified by mouse, rat, guinea pig, hamster, ferret and chinchilla. The invention's compositions and methods are also useful for a subject "in need of reducing one or more symptoms of" a disease includes a subject that exhibits and/or is at risk of exhibiting one or more symptoms of the disease. For Example, subjects may be at risk based on family history, genetic factors, environmental factors, etc. This term includes animal models of the disease. Thus, administering a composition (which reduces a disease and/or which reduces one or more symptoms of a disease) to a subject in need of reducing the disease and/or of reducing one or more symptoms of the disease includes prophylactic administration of the composition (i.e., before the disease and/or one or more symptoms of the disease are detectable) and/or therapeutic administration of the composition (i.e., after the disease and/or one or more symptoms of the disease are detectable). The invention's compositions and methods are also useful for a subject "at risk" for disease refers to a subject that is predisposed to contracting and/or expressing one or more symptoms of the disease. This predisposition may be genetic (e.g., a particular genetic tendency to expressing one or more symptoms of the disease, such as heritable disorders, etc.), or due to other factors (e.g., environmental conditions, exposures to detrimental compounds, including carcinogens, present in the environment, etc.). The term subject "at risk" includes subjects "suffering from disease," i.e., a subject that is experiencing one or more symptoms of the disease. It is not intended that the present invention be limited to any particular signs or symptoms. Thus, it is intended that the present invention encompass subjects that are experiencing any range of disease, from sub-clinical symptoms to full-blown disease, wherein the subject exhibits at least one of the indicia (e.g., signs and symptoms) associated with the disease.

"Subject in need of reducing one or more symptoms of" a disease, e.g., infection with a pathogen, includes a subject that exhibits and/or is at risk of exhibiting one or more symptoms of the disease. For Example, subjects may be at risk based on family history, genetic factors, environmental factors, etc. This term includes animal models of the disease.

The terms "pathogen" and "animal pathogen" refer to any organism which causes a disease in an animal. Pathogens include, but are not limited to, viruses, bacteria, protozoa, nematodes, fungus, etc.

The terms "pathogenic" and "virulent" when in reference to a microorganism, such as virus, bacteria, parasite, etc. refer to the ability of the microorganism to produce an infectious disease in another organism (e.g., mammal).

The terms "reduce," "inhibit," "diminish," "suppress," "decrease," and grammatical equivalents (including "lower," "smaller," etc.) when in reference to the level of any molecule (e.g., amino acid sequence, and nucleic acid sequence, antibody, etc.), cell, virus, and/or phenomenon (e.g., expression, transcription, translation, viral infection, viral productive infection, viral replication, viral replication competence, Rep-mediated nuclease activity, site-specific integration into a genome, helicase activity, disease symptom, binding to a molecule, specificity of binding of two molecules, affinity of binding of two molecules, specificity to disease, sensitivity to disease, affinity of binding, enzyme activity, etc.) in a first sample (or in a first subject) relative to a second sample (or relative to a second subject), mean that the quantity of molecule, cell and/or phenomenon in the first sample (or in the first subject) is lower than in the second sample (or in the second subject) by any amount that is statistically significant using any art-accepted statistical method of analysis. In one embodiment, the quantity of molecule, cell and/or phenomenon in the first sample (or in the first subject) is at least 10% lower than, at least 25% lower than, at least 50% lower than, at least 75% lower than, and/or at least 90% lower than the quantity of the same molecule, cell and/or phenomenon in the second sample (or in the second subject). In another embodiment, the quantity of molecule, cell, and/or phenomenon in the first sample (or in the first subject) is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in the second sample (or in the second subject). In one embodiment, the first subject is exemplified by, but not limited to, a subject that has been manipulated using the invention's compositions and/or methods. In a further embodiment, the second subject is exemplified by, but not limited to, a subject that has not been manipulated using the invention's compositions and/or methods. In an alternative embodiment, the second subject is exemplified by, but not limited to, a subject to that has been manipulated, using the invention's compositions and/or methods, at a different dosage and/or for a different duration and/or via a different route of administration compared to the first subject. In one embodiment, the first and second subjects may be the same individual, such as where the effect of different regimens (e.g., of dosages, duration, route of administration, etc.) of the invention's compositions and/or methods is sought to be determined in one individual. In another embodiment, the first and second subjects may be different individuals, such as when comparing the effect of the invention's compositions and/or methods on one individual participating in a clinical trial and another individual in a hospital.

The terms "increase," "elevate," "raise," and grammatical equivalents (including "higher," "greater," etc.) when in reference to the level of any molecule (e.g., amino acid sequence, and nucleic acid sequence, antibody, etc.), cell, virus, and/or phenomenon (e.g., expression, transcription, translation, viral infection, viral productive infection, viral replication, viral replication competence, Rep-mediated nuclease activity, site-specific integration into a genome, helicase activity, disease symptom, binding to a molecule, specificity of binding of two molecules, affinity of binding of two molecules, specificity to disease, sensitivity to disease, affinity of binding, enzyme activity, etc.) in a first sample (or in a first subject) relative to a second sample (or relative to a second subject), mean that the quantity of the molecule, cell and/or phenomenon in the first sample (or in the first subject) is higher than in the second sample (or in the second subject) by any amount that is statistically significant using any art-accepted statistical method of analysis. In one embodiment, the quantity of the molecule, cell and/or phenomenon in the first sample (or in the first subject) is at least 10% greater than, at least 25% greater than, at least 50% greater than, at least 75% greater than, and/or at least 90% greater than the quantity of the same molecule, cell and/or phenomenon in the second sample (or in the second subject). This includes, without limitation, a quantity of molecule, cell, and/or phenomenon in the first sample (or in the first subject) that is at least 10% greater than, at least 15% greater than, at least 20% greater than, at least 25% greater than, at least 30% greater than, at least 35% greater than, at least 40% greater than, at least 45% greater than, at least 50% greater than, at least 55% greater than, at least 60% greater than, at least 65% greater than, at least 70% greater than, at least 75% greater than, at least 80% greater than, at least 85% greater than, at least 90% greater than, and/or at least 95% greater than the quantity of the same molecule, cell and/or phenomenon in the second sample (or in the second subject). In one embodiment, the first subject is exemplified by, but not limited to, a subject that has been manipulated using the invention's compositions and/or methods. In a further embodiment, the second subject is exemplified by, but not limited to, a subject that has not been manipulated using the invention's compositions and/or methods. In an alternative embodiment, the second subject is exemplified by, but not limited to, a subject to that has been manipulated, using the invention's compositions and/or methods, at a different dosage and/or for a different duration and/or via a different route of administration compared to the first subject. In one embodiment, the first and second subjects may be the same individual, such as where the effect of different regimens (e.g., of dosages, duration, route of administration, etc.) of the invention's compositions and/or methods is sought to be determined in one individual. In another embodiment, the first and second subjects may be different individuals, such as when comparing the effect of the invention's compositions and/or methods on one individual participating in a clinical trial and another individual in a hospital.

The terms "alter" and "modify" when in reference to the level of any molecule and/or phenomenon refer to an increase and/or decrease.

"Substantially the same" when in reference to the level of any molecule (e.g., amino acid sequence, and nucleic acid sequence, antibody, etc.), cell, virus, and/or phenomenon (e.g., expression, transcription, translation, viral infection, viral productive infection, viral replication, viral replication competence, Rep-mediated nuclease activity, site-specific integration into a genome, helicase activity, disease symptom, binding to a molecule, specificity of binding of two molecules, affinity of binding of two molecules, specificity to disease, sensitivity to disease, affinity of binding, enzyme activity, etc.) in a first sample (or in a first subject) relative to a second sample (or relative to a second subject), mean that the quantity of molecule, cell and/or phenomenon in the first sample (or in the first subject) is not different from the quantity in the second sample (or in the second subject) using any art-accepted statistical method of analysis. In one embodiment, the quantity of molecule, cell and/or phenomenon in the first sample (or in the first subject) is from 90% to 100% (e.g., 90%, 91%, 92%, 93%, 94%, 95%, 96%, 97%, 98%, 99%, and 100%) of the quantity in the second sample (or in the second subject).

Reference herein to any numerical range expressly includes each numerical value (including fractional numbers and whole numbers) encompassed by that range. To illustrate, and without limitation, reference herein to a range of "at least 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc. In yet another illustration, reference herein to a range of from "5 to 10" includes each whole number of 5, 6, 7, 8, 9, and 10, and each fractional number such as 5.1, 5.2, 5.3, 5.4, 5.5, 5.6, 5.7, 5.8, 5.9, etc.

BRIEF SUMMARY OF THE INVENTION

The AAV Rep78 protein is required for SSI although it displays an inhibitory effect on virus replication in hybrid viruses (e.g., Ad/AAV viruses). To date, prior art strategies to construct hybrid viruses (e.g., Ad/AAV) by controlling Rep expression have met with limited success. The invention provides the discovery that AAV Rep's cis-acting inhibitory effect on hybrid virus replication and/or replication competence and/or infectivity and/or productive infectivity is due to a role of an inhibitory sequence within the Rep ORF.

The inventors discovered dramatic results when comparing the expression of Scrambled Rep78 and/or Deoptimized Rep78 with wild-type Rep78 ORFs within a first generation Adenovirus backbone (Ad/Scr, Ad/Deopt and Ad/wtRep). In particular, where Ad/wtRep was incapable of replication, Ad/Scr and Ad/Deopt replicated at comparable levels to other first generation Ad, thus demonstrating a clear role for a sequence specific signal within the wild-type Rep78 ORF in the inhibition of virus replication. Modification of this signal (e.g., scrambled and/or deoptimized sequences) allowed virus replication and tolerance of a high level of Rep protein expression. The inventors localized the inhibitory signal to an approximately 135 bp sequence within the Rep ORF. The identification of a sequence specific inhibitory signal for AAV Rep mediated inhibition of Ad replication explains the prior art's inconsistent and often frustrating results obtained with production of hybrid viruses (e.g., Ad/AAV) over the years and paves the way for the production of rAAV and hybrid viruses (e.g., Ad/AAV), such as in gene therapy and vaccine applications.

DETAILED DESCRIPTION OF THE INVENTION

The invention provides adeno-associated virus (AAV) replication (Rep) sequences. In one embodiment, the invention provides nucleotide sequences encoding a chimeric protein, wherein the encoded chimeric protein contains a wild type AAV Rep inhibitory amino acid sequence, and wherein the nucleotide sequences contain a scrambled and/or deoptimized polynucleotide sequence encoding the wild type AAV Rep inhibitory amino acid sequence. The invention provides vectors, cells, and viruses containing the invention's sequences. Also provided are methods for detecting portions of the AAV Rep inhibitory amino acid sequence, which reduce replication and/or infection and/or productive infection by viruses. The invention's compositions and methods are useful for site-specific integration and/or expression of heterologous sequences by recombinant adeno-associated virus (rAAV) vectors and by rAAV virus particles, such as hybrid viruses (e.g., Ad-AAV) comprising such vectors. The invention's compositions and methods find application in, for example, gene therapy and/or vaccines.

The invention's methods and compositions provide a strategy for safe, site-specific gene integration that is of considerable advantage for gene therapy approaches. In one embodiment, the inventors use the unique ability of Adeno-associated virus (AAV) genetic elements in conjunction with adenovirus to generate novel hybrid viruses (Ad/AAV) that retain the capacity for stable transgene integration into a safe region of the genome. This approach requires AAV genetic elements in conjunction with AAV Rep78, to provide the key elements for safe gene integration into the human genome. Historically, the ability to assemble such site-specific integrating viruses has been limited because of the known cellular toxicity of AAV Rep78, coupled with Rep78's inhibitory role in adenovirus replication. This has lead to difficulty in the prior art in generating an integrating transgene within the back-bone of a single Ad/AAV hybrid virus.

The invention also provides the discovery of an AAV nucleotide sequence (and portions thereof) in the Rep78 open reading frame (ORF) that plays a role in AAV Rep mediated inhibition of virus (e.g. Adenovirus) replication.

The invention's AAV Rep inhibitory nucleotide sequence was localized by the inventors to a 564-bp nucleotide sequence (SEQ ID NO:17). The 564-bp nucleotide sequence includes an AAV Rep inhibitory nucleotide sequence portion 135-bp nucleotide sequence (SEQ ID NO:01) from bp 1782 to bp 1916 of the AAV2 genome, which encompasses the Rep68/40 donor splice site and the P40 promoter region.

The inventors' discovery of the invention's AAV Rep inhibitory nucleotide sequence that mediates inhibitions of viral (e.g., Adenoviral) replication explains the prior art's inconsistent and often frustrating results reported over the years with respect to the production of hybrid Adenovirus/Adeno-associated virus (Ad/AAV) carrying Rep.

Data herein demonstrate that, in one embodiment, the modification (e.g., by scrambling and/or deoptimization) of the invention's AAV Rep inhibitory nucleotide sequence results in removal of AAV Rep mediated inhibition of Adenovirus replication, enabling Adenoviral replication at a level that is substantially the same as first generation Adenoviruses not carrying Rep. Data herein also demonstrate the modification of the invention's AAV Rep inhibitory nucleotide sequence allows Adenovirus to replicate even in the absence of regulated Rep expression, revealing a tolerance for high Rep protein expression levels.

The inventor's discovery that modifying (e.g., by scrambling and/or deoptimization) the invention's AAV Rep inhibitory nucleotide sequence (and/or portions thereof) resulted in removal of AAV Rep mediated inhibition of Adenovirus replication, results in the production of high titer, stable virus (e.g., Adenovirus) carrying Rep, and paves the way for large scale production of hybrid AAV viruses (e.g. Ad/AAV) as well as of recombinant AAV (rAAV) for gene therapy and vaccines.

The inventors also found that even tightly regulated Rep78 expression cassettes that were capable of being carried by helper dependent viruses were not viable within a ΔE1ΔE3 Ad backbone. Further, this absence of replication even in the presence of controlled levels of Rep contrasts with robust Adenoviral replication seen in the presence of high levels of Rep expression produced by Rep expressing cell lines such as C12. The inventors hypothesized that increased inhibition of replication when Rep was carried on the Adenoviral moiety could either be due to increased expression accompanying an increase in copy number, or due to an actual role for the sequence of the Rep ORF.

To distinguish between these two possibilities, the inventors applied a computer algorithm to modify the 1865 bp Rep78 DNA ORF using synonymous codons, generating a Scrambled (Scr) and a Deoptimized (Deopt) sequence. These modified sequences are only 70-80% similar to wild-type Rep78 nucleotide sequence, but encode exactly the same amino acid sequence. Further, the Deoptimized sequence specifically uses codons in underrepresented pairs, expressing Rep78 protein at reduced levels due to codon pair bias. Codon pair bias refers to the preference for some codon pairs over other synonymous codons to encode the same pair of adjacent amino acids. Utilization of underrepresented codon pairs results in an ORF that is expressed at reduced levels, due to inefficient translation. The inventors hypothesized that modification of the Rep78 DNA sequence without changing the protein expressed will help identify any role the ORF plays in the inhibition of Adenoviral replication. Further, comparing the ability of Adenoviruses carrying sequence modified Rep genes which express different levels of Rep, to replicate, will help tease out the extent of the contribution of the sequence of the Rep ORF versus Rep78 protein levels on the inhibition of Adenoviral replication.

For further clarity, the invention is further described under (A) Adeno-associated Virus and genome structure, (B) AAV Rep nucleotide sequences, (C) Vectors, (D) Viruses, (E) Cells, (F) Vaccines, (G) Exemplary applications of the invention's compositions for identification of functional portions of wild type AAV Rep inhibitory nucleotide sequences, (H) Exemplary applications of the invention's compositions for generation of viruses, and (I) Exemplary applications of the invention's compositions for expression of nucleotide sequences (e.g., in gene therapy and/or vaccine applications).

A. Adeno-Associated Virus and Genome Structure

The invention provides the discovery of useful AAV Rep nucleotide sequences. "AAV" and "Adeno-associated virus" refers to a small ssDNA virus belonging to the family Parvoviridae, which was found to be dependent on other viruses (e.g., adenovirus, Herpes-simplex, Epstein Barr, and cytomegalovirus) for productive infection.

AAV is exemplified by AAV2, the most widely studied AAV family member. No pathology has been convincingly linked with AAV2 infection of humans. AAV can undergo a lytic or lysogenic life cycle. Uniquely, in cell culture in the absence of helper virus functions, the virus establishes a persistent infection by integrating site-specifically into the AAVS1 site on chromosome 19 (q13.3qter) of the host genome in humans and non-human primates (135-138). However, viral sequences are also found as concatemers of the AAV genome in an extra-chromosomal form.

Figure 9:
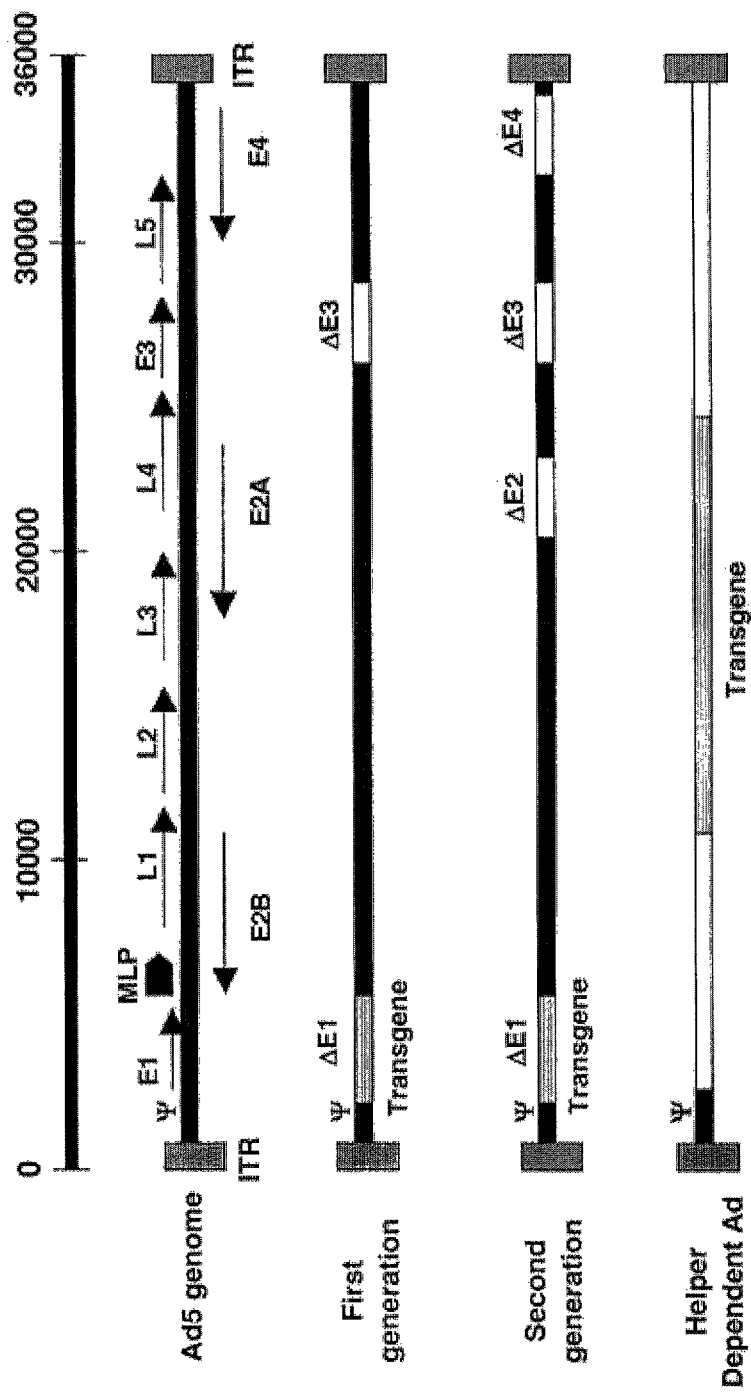
FIG. 9: Adenovirus genome (Alba et al. Gene Therapy 2005:12:S18-27).
Figure 10B:
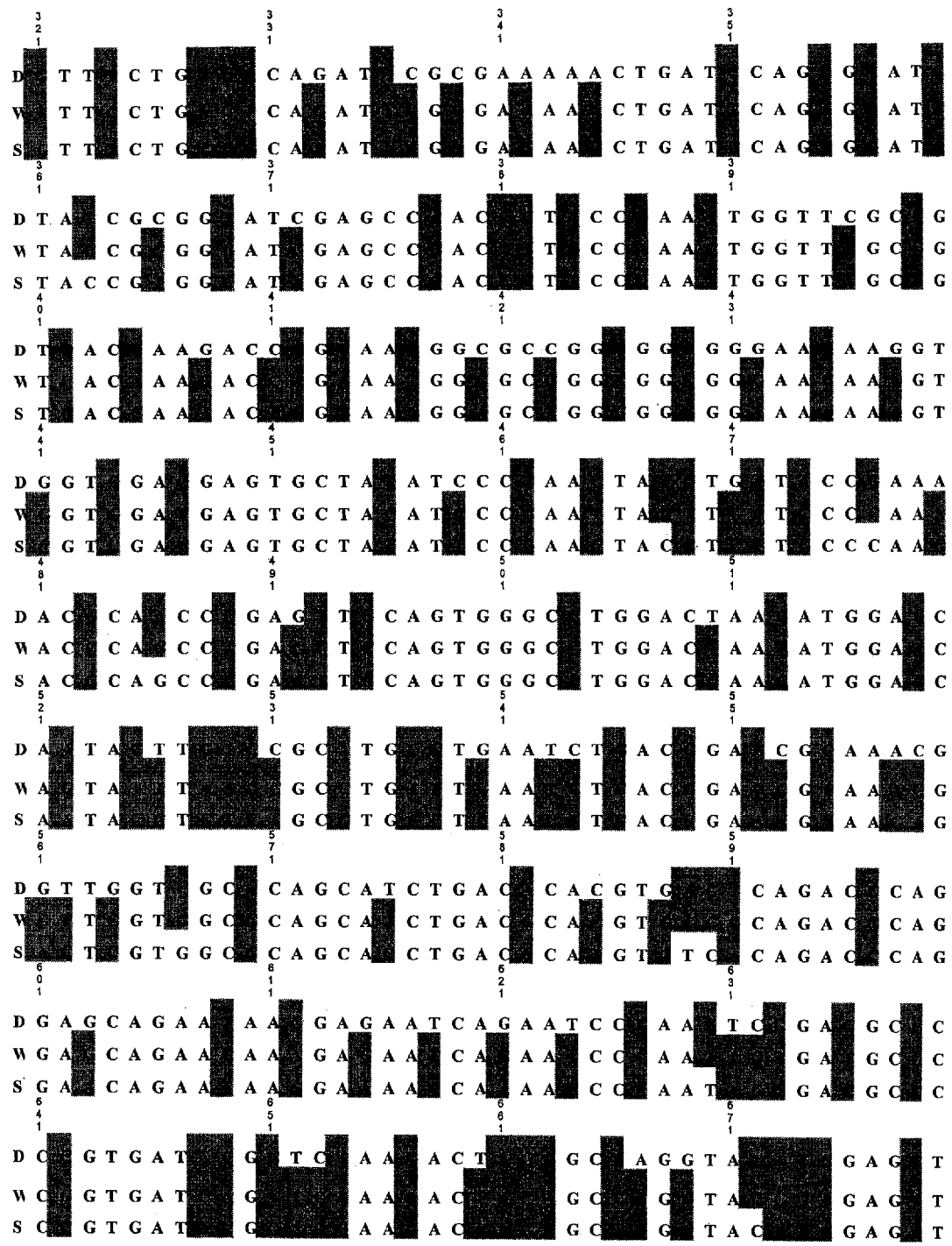
FIG. 10: Alignments of sRep78 (S) (SEQ ID NO:06) and dRep78 (D) (SEQ ID NO:08) with wtRep78 (W) (SEQ ID NO:03).
Figure 10C:
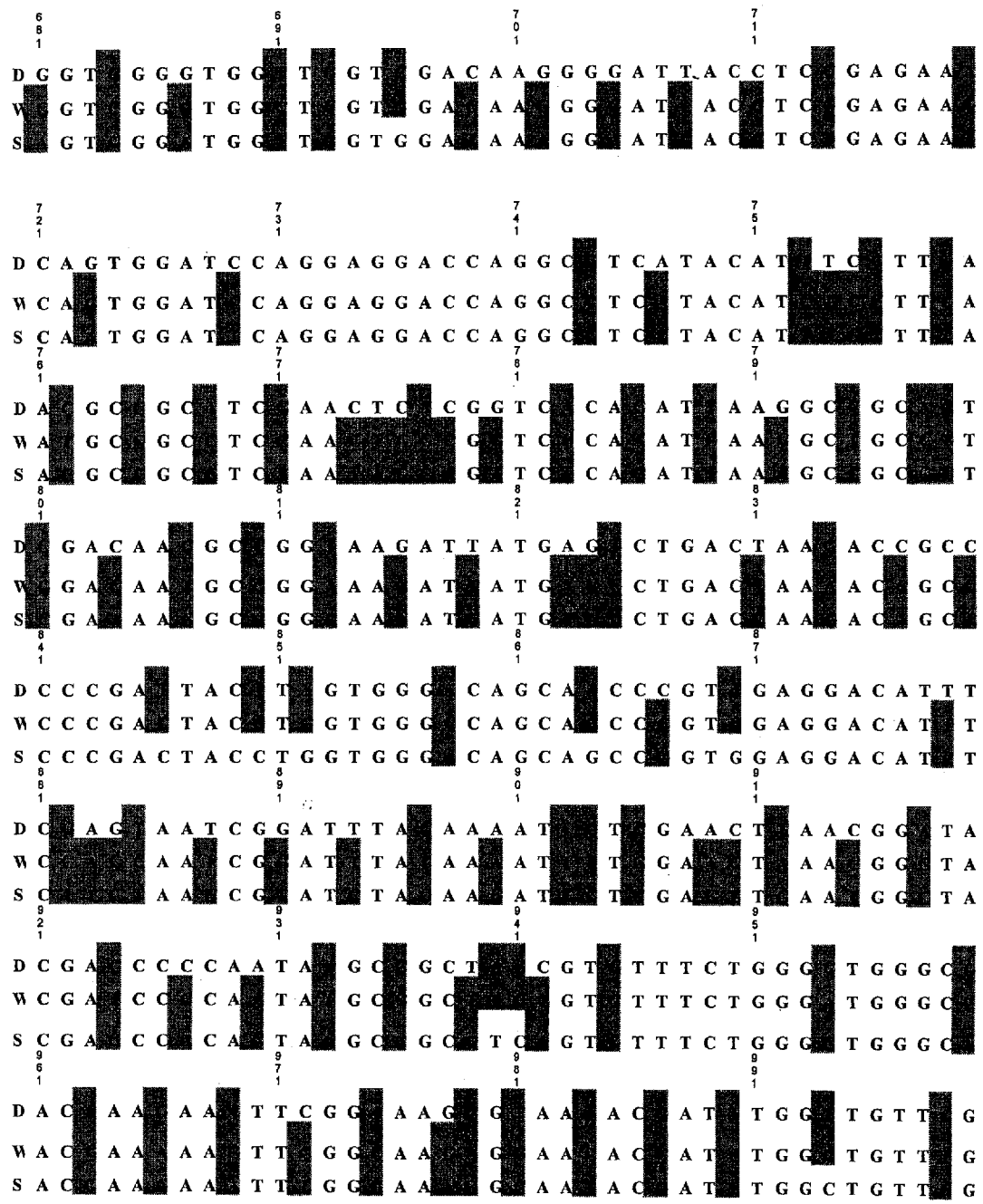
Figure 10D:
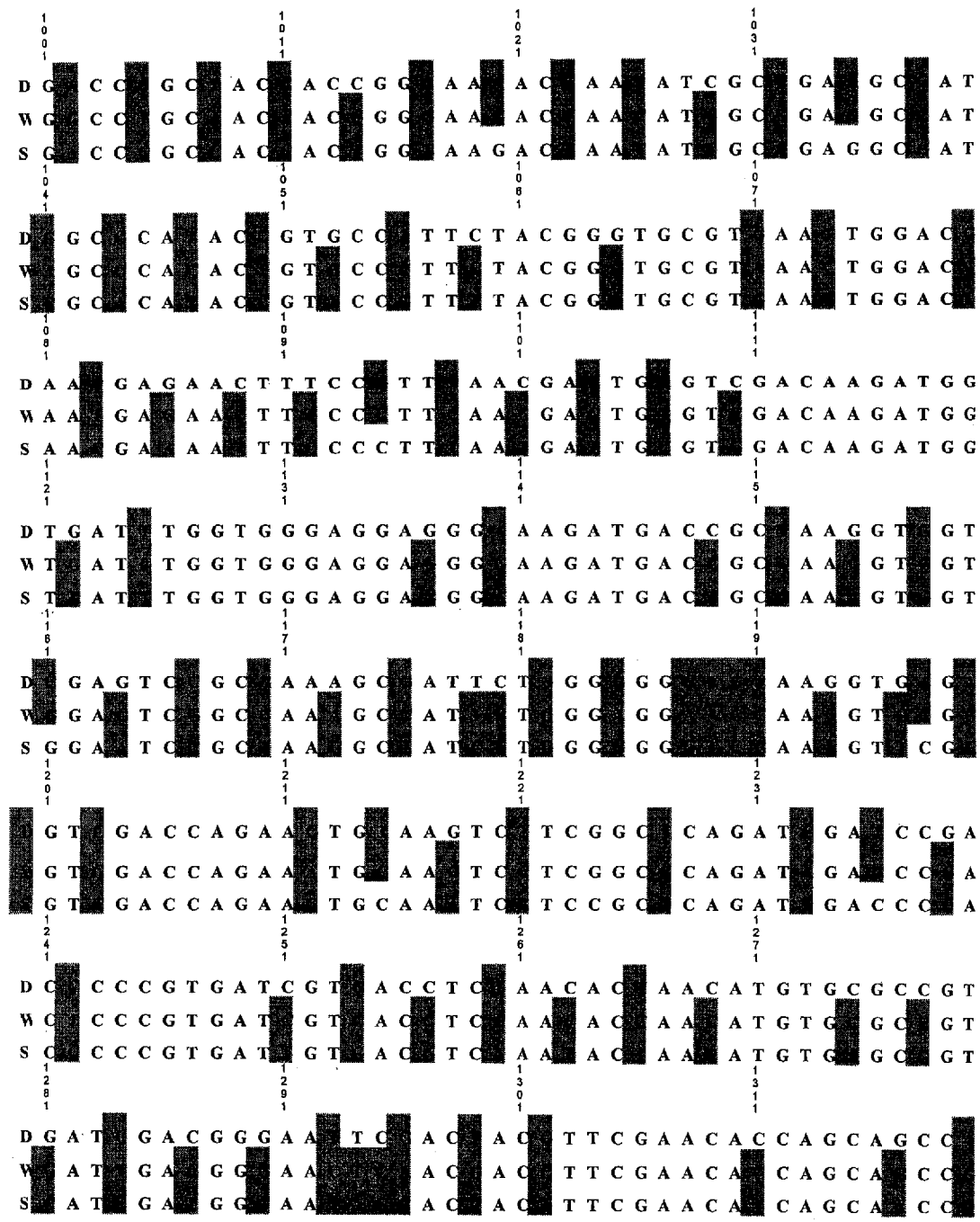
Figure 10E:
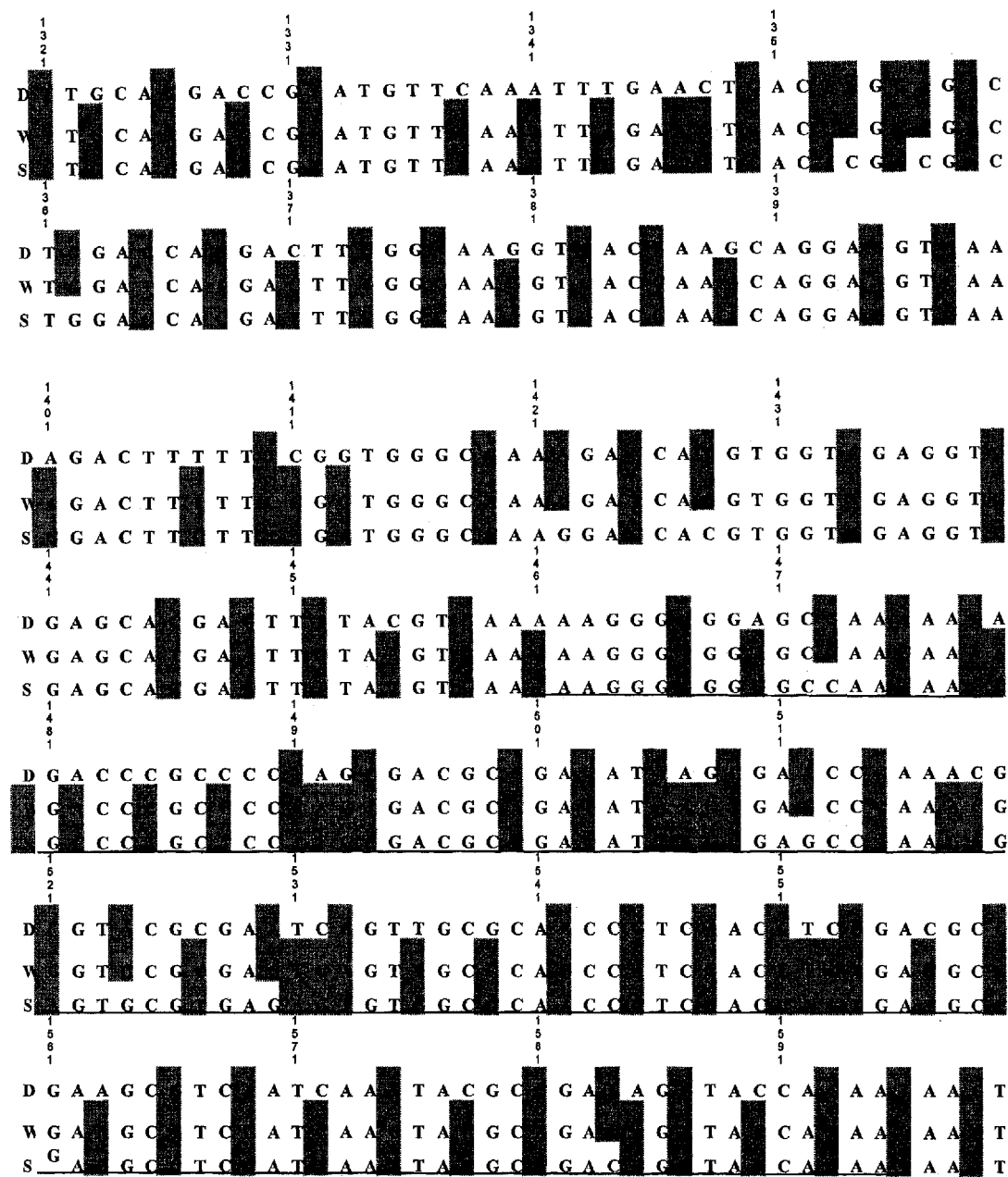
Figure 10F:
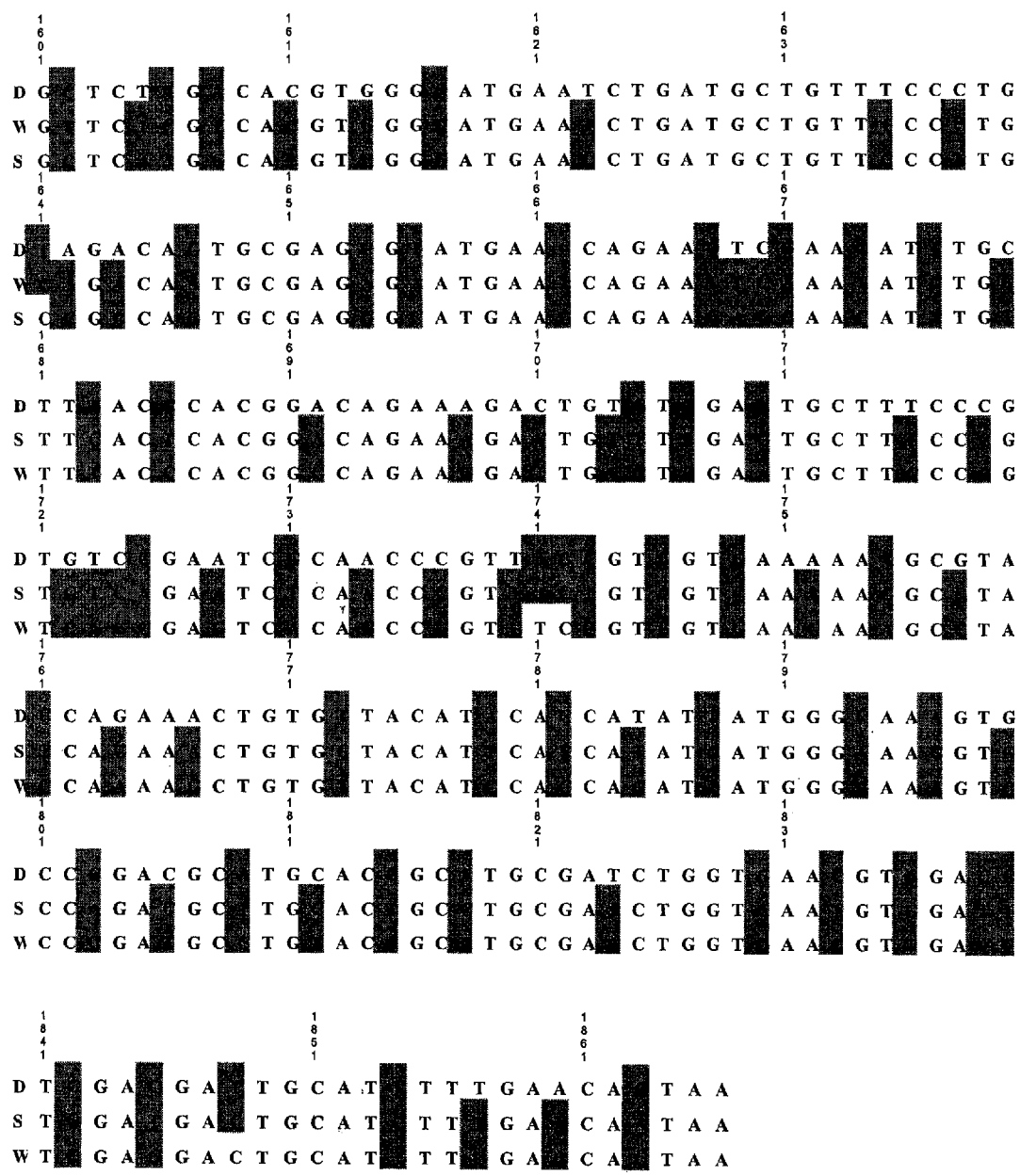

The AAV2 genome (FIG. 9) is a linear single stranded DNA of about 4.7 Kb. Both sense and antisense strands are packaged into virions with equal frequency. The genome contains T shaped "inverted terminal repeats" flanking two open reading frames (ORFs), "Rep" and "Cap." The Rep ORF encodes Rep78 (exemplified by SEQ ID NO:04 of FIG. 6 panel A) and the alternately spliced Rep68 (SEQ ID NO:05 of FIG. 6 panel B) from promoter p5 and Rep52 and Rep40 from promoter 19. The p19 promoter lies within the coding sequence for the larger Rep proteins. The Cap ORF encodes three structural proteins VP1, VP2 and VP3 from the p40 promoter.

The genome of the AAVs has been cloned, sequenced and characterized. For example, the genomic sequences of AAV2 are provided in GenBank accession No. J01901, AF043303, and NC_001401. In general, the AAV genome comprises about 4,700 bases and contains, at each end, an inverted repeat region (ITR) of approximately 145 bases, serving as the origin of replication of the virus. The remainder of the genome is divided into 2 essential regions: the left-hand part of the genome, containing the rep gene involved in replication of the virus and expression of the viral genes and; the right-hand part of the genome, containing the cap gene encoding the capsid proteins of the virus (Hearing et al., U.S. Pat. No. 7,563,617).

Productive infection by AAV requires co-infection by a helper virus such as Adenovirus. In the absence of helper virus infection, the AAV establishes a latent infection by site-specifically integrating into the AAVS1 site on the q arm of the 19$^{th}$ chromosome (19q13.3qter).

In particular, the invention's AAV nucleotide and amino acid sequences, as well as vectors, viruses (e.g., rAAV particles, and hybrid AAV particles such as Ad/AAV), and cells containing one or more of these sequences, are characterized by, among other things, containing an adeno-associated virus terminal repeat sequence. The terms "terminal repeat," "TR," "intact TR," and "full-length TR" when in reference to an adeno-associated virus (AAV) sequence, are used interchangeably to refer to a nucleotide sequence which is located at each end of the AAV single-stranded DNA genome, and which is the only cis-acting element required for genome replication and packaging. The AAV TR, in the presence of either Rep68 or Rep78, is sufficient for site-specific viral DNA integration. Alternatively, the AAV TR refers to a nucleotide sequence which is derived from an AAV and which is involved in AAV DNA replication, AAV DNA excision, or AAV DNA packaging into virus. In a preferred embodiment, the AAV TR is derived from AAV2 strain and is exemplified by the 145-bp sequence [5'-ttggccactc cctctctgcg cgctcgctcg ctcactgagg ccgggcgacc aaaggtcgcc cgacgcccgg gctttgcccg ggcggcctca gtgagcgagc gagcgcgcag agagggagtg gccaactcca tcactagggg ttcct-3' (SEQ ID NO:10)] from nucleotide 1 to nucleotide 145 of the AAV2 genomic sequence of GenBank No. J01901 (Hearing et al., U.S. Pat. No. 7,563,617). The AAV TR exist in nature as an "inverted terminal repeat" ("ITR") in a flip or flop orientation, based on the orientation of the internal palindrome with respect to the D sequence. The AAV ITR contains a hairpin structure that appears to contain hot spots of integration.

"Rep" and "replication protein" when in reference to an adeno-associated virus (AAV) protein sequence, refers to a protein encoded by a AAV rep gene region, and is exemplified by AAV Rep proteins Rep78, Rep68, Rep52 and Rep40.

The "rep gene region" of the adeno-associated virus genome refers to a nucleotide sequence that is derived from an adeno-associated virus, and which encodes one or more Rep proteins. AAV Rep proteins include Rep78, Rep68, Rep52 and Rep40.

"Rep68" and "Rep78," are Rep sequences produced from unspliced and spliced transcripts from the p5 promoter. In one embodiment, Rep78 is exemplified by the wild type Rep78 SEQ ID NO:04 (FIG. 6, panel A) encoded by the DNA sequence SEQ ID NO:03 (FIG. 5). In another embodiment, Rep68 is exemplified by wild type Rep68 SEQ ID NO:05 (FIG. 6, panel B). Rep78 and Rep68 are multifunctional proteins with largely overlapping functions in almost every stage of the AAV life cycle, such as site-specific DNA binding, helicase activity, and/or site-specific endonuclease activity. Rep78 and/or Rep68 are required in trans for AAV replication and/or excision from the host genome (U.S. Pat. No. 5,658,776; Trempe et al., U.S. Pat. No. 5,837,484; Burstein et al., WO 98/27207; Johnson et al., U.S. Pat. No. 5,658,785; Carter, U.S. Pat. No. 7,785,888). Thus, a "functional" Rep protein (and/or portion thereof) refers to a protein (and/or portion thereof) that has one or more Rep activity exemplified by site-specific DNA binding, helicase activity, and site-specific endonuclease activity.

"AAV Rep inhibitory amino acid sequence" refers to the amino acid sequence encoded by the 135-bp DNA sequence from bp 1782 to bp 1916 of the AAV2 genome (FIG. 4 panel B).

"Rep-mediated excision" and "Rep-mediated nuclease" when in reference the activity by a Rep protein, or functional fragment thereof, interchangeably refer to the endonuclease activity of the protein in producing two or more fragments of a substrate nucleotide sequence. Methods for determining Rep-mediated excision activity are known in the art, and described herein. For example, data herein demonstrate that adenovirus Ad/sRep78 (containing a scrambled Rep78 sequence) and adenovirus Ad/dRep78 (containing a deoptimized Rep78 sequence) retained Rep-mediated excision activity as demonstrated by cleavage of a folded AAV ITR as substrate (Example 3).

"Rep52" and "Rep40" are Rep sequences produced from unspliced and spliced transcripts respectively, from the p19 promoter. All four Rep proteins possess helicase and ATPase activity. In addition, Rep68 and Rep78 are capable of site-specific binding to the ribosome binding site (RBS) and have site-specific endonuclease activity, required for separation of replicated viral genomes.

The "Cap gene" of adeno-associated virus refers to a gene encoding VP1, VP2 and VP3 structural proteins making up the AAV capsid. The exemplary AAV-2 "AAV capsid" comprises 60 viral capsid proteins arranged into an icosahedral structure, with VP1, VP2 and VP3 present in approximately a 1:1:8 molar ratio.

B. AAV Rep Nucleotide Sequences

The inventors have discovered that first generation adenoviruses carrying AAV Rep78 expressed under a tetracycline inducible system were incapable of growing (Example 2). This contradicts prior art reports of the production of a helper dependent Ad carrying Rep78 (Recchia et al. (2004) *Molecular Therapy* 10(No. 4):660-670). A similar lack of the reproducibility of generating replicative virus carrying AAV Rep78 is demonstrated by the prior art's failure to construct a first generation Ad carrying Rep expressed under the α1 antitrypsin promoter by one group (Carlson et al. (2002) *Molecular Therapy* 6(1):91-98), in contrast to reports that a helper dependent Ad carrying Rep78 expressed under an α1 antitrypsin promoter was capable of growing (Recchia et al. (1999) *PNAS* 96:2615-2620).

Thus, in one embodiment, the invention provides AAV recombinant nucleotide sequences (as well as vectors, viruses (e.g., rAAV, and hybrid AAV), and cells containing one or more these sequences) encoding a chimeric protein, a) wherein the encoded chimeric protein i) comprises at least a portion of wild type AAV Rep inhibitory amino acid sequence listed as SEQ ID NO:20 (i.e., the 564-bp DNA sequence from bp1623 to bp 2186 of the AAV2 genome) and/or SEQ ID NO:02 (i.e., the 135-bp DNA sequence from bp 1782 to bp 1916 of the AAV2 genome, FIG. 4 panel B), and ii) has Rep-mediated nuclease activity, and b) wherein the recombinant nucleotide sequence comprises a scrambled polynucleotide sequence encoding wild type AAV Rep inhibitory amino acid sequence listed as SEQ ID NO:20 and/or SEQ ID NO:02 (and/or portion thereof).

One advantage of the invention's AAV nucleotide and amino acid sequences, as well as vectors, viruses (e.g., rAAV particles, and hybrid AAV particles such as Ad/AAV), and cells containing one or more of these sequences, is that they are useful in gene therapy (including gene transfer for monogenic disorders such as hemophilia, and polygenic disease such as cancer) and vaccines. The invention's AAV nucleotide and amino acid sequences, as well as vectors, viruses (e.g., rAAV particles, and hybrid AAV particles such as Ad/AAV), and cells containing one or more of these sequences, can be used to express various heterologous gene products in host cells by transformation and transduction, respectively.

Another advantage of the invention's AAV nucleotide and amino acid sequences, as well as vectors, viruses (e.g., rAAV particles, and hybrid AAV particles such as Ad/AAV), and cells containing one or more of these sequences, is that they retain Rep-mediated nuclease activity, yet lack the AAV Rep inhibitory nucleotide sequence that inhibits viral productive replication.

Yet a further advantage of the invention's AAV nucleotide and amino acid sequences, as well as vectors, viruses (e.g., rAAV particles, and hybrid AAV particles such as Ad/AAV), and cells containing one or more of these sequences, is that they provide hybrid viruses (e.g. Ad-AAV hybrid virus) carrying the AAV ITR flanked transgene and/or the AAV Rep-Cap coding sequences, which allows efficient co-infection of 293 cells, eliminate the need for producer cell lines and would greatly ease the production of high titer AAV. These hybrid viruses also retain the capacity for stable transgene integration into a safe region of the genome.

Another advantage of the invention's AAV nucleotide and amino acid sequences, as well as vectors, viruses (e.g., rAAV particles, and hybrid AAV particles such as Ad/AAV), and cells containing one or more of these sequences, is that they provide hybrid viruses (e.g. Ad-AAV hybrid virus) that can tolerate Rep78 (or Rep68) within the viral background, which provides a unique opportunity to place all genetic elements in a single virus for the purpose of safely integrating a transgene into a safe region of the human genome. This is a significant advance in the field as it provides a safer alternative to retroviruses and lentiviruses in gene replacement strategies.

Data herein demonstrate that the inhibitory function of the wild type AAV Rep inhibitory nucleotide sequence, exemplified by SEQ ID NO:01, on virus replication was abolished when using either a) a scrambled AAV Rep inhibitory nucleotide sequence that did NOT alter the level of expressed Rep78 or Rep68, or b) a deoptimized AAV Rep inhibitory nucleotide sequence that DID reduce the level of expressed Rep78 and/or Rep68. In particular, data herein demonstrate that the exemplary adenovirus Ad/sRep78 (containing a scrambled Rep78 sequence) and adenovirus Ad/dRep78 (containing a deoptimized Rep78 sequence) retained Rep-mediated nuclease activity as demonstrated by cleavage of a folded AAV ITR as substrate (Example 3).

The invention's AAV nucleotide and amino acid sequences, as well as vectors, viruses (e.g., rAAV particles, and hybrid AAV particles such as Ad/AAV), and cells containing one or more of these sequences, carrying AAV elements on the backbone of a larger virus are useful not only for the production of rAAV, but also as potential integrating gene transfer vectors. The only difference in Rep expression in such vectors would be the requirement for both Rep68/78 and Rep52 expression for rAAV production, versus only Rep68/78 expression needed for integration.

Production of a rAAV possessing AAV's unique ability of Rep mediated site-specific integration is not feasible, clue to the small size of its genome and the toxic effects of Rep protein on the host cell (Winocour et al. (1988) Perturbation of the cell cycle by adeno-associated virus. *Virology* 167: 393-399). Introduction of a Rep cassette into the rAAV would further reduce the viable transgene size to about 3 Kb. Further, since the entire cassette flanked by the AAV ITR integrates in the presence of Rep protein, an internal Rep cassette would also be integrated. Alternatively, since the only elements required for site-specific integration have been shown to be the AAV ITR or IEE in cis and the Rep68/78 protein in trans, an AAV ITR flanked transgene cassette and a Rep expression cassette outside the AAV TR's could be carried on the backbone of a larger virus (such as adenovirus, herpes simplex virus, retrovirus, lentivirus, baculovirus, etc.), combining AAV's ability to site-specifically integrate with the large transgene size of a larger virus.

In one embodiment, the invention's AAV nucleotide and amino acid sequences, as well as vectors, viruses (e.g., rAAV particles, and hybrid AAV particles such as Ad/AAV), and cells containing one or more of these sequences, are useful in gene therapy (including gene transfer for monogenic disorders such as hemophilia, and polygenic disease such as cancer) and vaccines.

i. Heterologous Polynucleotide Sequences

The invention's compositions can be used to express various heterologous gene products in host cells by transduction. Thus, in one embodiment, the recombinant nucleotide sequence comprises a heterologous polynucleotide sequence operably linked to a first AAV ITR. In a more preferred embodiment, the heterologous polynucleotide sequence is flanked by the first AAV ITR and by a second AAV ITR.

The terms "flanking," and "flank" when made in reference to a first and second nucleotide sequences (e.g., inverted terminal repeats (IIRs)) in relation to a third nucleotide sequence (e.g., a DNA sequence of interest) mean that the first nucleotide sequence is linked to the 5' end (i.e., upstream) of the third sequence, and the second nucleotide sequence is linked to the 3' end (i.e., downstream) of the third sequence, preferably (although not necessarily) without any intervening sequences of viral origin in order to reduce the likelihood of recombination. Recent evidence suggests that a single ITR can be sufficient to carry out the functions normally associated with configurations comprising two ITRs (U.S. Pat. No. 5,478,745), and vector constructs with only one ITR can thus be employed in conjunction with the packaging and production methods described herein. The resultant recombinant viral vector is referred to as being "defective" in viral functions when specific viral coding sequences are deleted from the vector (Carter, U.S. Pat. No. 7,785,888).

In preferred embodiments, the invention's sequences have Rep-mediated nuclease activity.

In a particular embodiment, the recombinant nucleotide sequence further comprises a nucleic acid sequence encoding one or more AAV capsid proteins.

ii. Scrambled AAV Rep Inhibitory Nucleotide Sequences, Including Deoptimized AAV Rep Inhibitory Nucleotide Sequences In preferred embodiments, the invention's AAV nucleotide and amino acid sequences, as well as vectors, viruses (e.g., rAAV particles, and hybrid AAV particles such as Ad/AAV), and cells containing one or more of these sequences, comprise a scrambled polynucleotide sequence encoding at least a portion of the wild type AAV Rep inhibitory amino acid sequence listed as SEQ ID NO:20 and/or SEQ ID NO:02.

Without intending to limit the particular sequence of the scrambled polynucleotide sequence encoding at least a portion of the wild type AAV Rep inhibitory amino acid sequence, in a particular embodiment, the scrambled polynucleotide sequence comprises SEQ ID NO:18 (FIG. 4G) and/or SEQ ID NO:07 (FIG. 4 panel C and FIG. 7 panel A).

In another embodiment, the scrambled polynucleotide sequence comprises a deoptimized AAV Rep inhibitory nucleotide sequence. While not limiting the exact sequence of the deoptimized AAV Rep inhibitory nucleotide sequence, in some embodiments, the deoptimized AAV Rep inhibitory nucleotide sequence comprises SEQ ID NO:19 (FIG. 4H) and/or SEQ ID NO:09 (FIG. 4 panel D, FIG. 7 panel B) and/or portion thereof.

In particular embodiment, the scrambled polynucleotide sequence that encodes at least a portion of the wild type AAV Rep inhibitory amino acid sequence, has from 66% to 99% identity to the wild type AAV Rep inhibitory nucleotide sequence listed as SEQ ID NO:17 (FIG. 4E, FIG. 12, FIG. 13) and/or SEQ ID NO:01 (FIG. 4 panel A, FIG. 12, FIG. 13). This includes identities of 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%. In a particular embodiment, the scrambled polynucleotide sequence that encodes at least a portion of the wild type AAV Rep inhibitory amino acid sequence, has from 70% to 80% identity to the wild type AAV Rep inhibitory nucleotide sequence listed as SEQ ID NO:17 and/or SEQ ID NO:01.

In a particular embodiment, the invention's AAV nucleotide and amino acid sequences, as well as vectors, viruses (e.g., rAAV particles, and hybrid AAV particles such as Ad/AAV), and cells containing one or more of these sequences, are isolated. The terms "purified," "isolated," and grammatical equivalents thereof refer to the reduction in the amount of at least one undesirable component (such as cell, protein, nucleic acid sequence, carbohydrate, etc.) from a sample, including a reduction by any numerical percentage of from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100%. Thus purification results in "enrichment," i.e., an increase in the amount of a desirable component cell, protein, nucleic acid sequence, carbohydrate, etc.) relative to the undesirable component. For example, "purifying" encapsidated vectors refers to the isolation of the encapsidated vectors in a more concentrated form (relative to the starting material, such as the cell lysate and/or extracellular solution), e.g., using $CsCl_2$ density gradients.

iii. Therapeutic Sequences for Gene Therapy and Vaccines

In particular embodiments, the heterologous polynucleotide sequence contained in the invention's AAV nucleotide and amino acid sequences, as well as vectors, viruses (e.g., rAAV particles, and hybrid AAV particles such as Ad/AAV), and cells containing one or more of these sequences, comprises a therapeutic nucleotide sequence. A "therapeutic nucleotide sequence" is a DNA sequence and/or RNA sequence of therapeutic interest, including sequences that encode a protein of therapeutic interest.

Therapeutic nucleotide sequences are exemplified by, but not limited to, sequences encoding a disease associated polypeptide, and/or encoding an antigen polypeptide.

Thus, in one embodiment, the therapeutic nucleotide sequences contained in the invention's AAV nucleotide and amino acid sequences, as well as vectors, viruses (e.g., rAAV particles, and hybrid AAV particles such as Ad/AAV), and cells containing one or more of these sequences, comprises a therapeutic sequence that encodes a "disease associated" polypeptide, meaning a polypeptide whose level (e.g., presence, absence, increase, and/or decrease relative to a control, etc.) that is correlated with disease and/or with risk of disease based on family history, genetic factors, environmental factors, etc.

Illustrative therapeutic nucleotide sequences that encode disease associated polypeptides include, but are not limited to, sequences which encode enzymes; lymphocytes (e.g., interleukins, interferons, TNF, etc.); growth factors (e.g., erythropoietin, G-CSF, M-CSF, GM-CSF, etc.); neurotransmitters or their precursors or enzymes responsible for synthesizing them; trophic factors (e.g., BDNF, CNTF, NGF, IGF, GMF, aFGF, bFGF, NT3, NT5, HARP/pleiotrophin, etc.); apolipoproteins (e.g., ApoAI, ApoAIV, ApoE. etc.); lipoprotein lipase (LPL); the tumor-suppressing genes (e.g., p53, Rb, RaplA, DCC k-rev, etc.); factors involved in blood coagulation (e.g., Factor VII, Factor VIII, Factor IX, etc.); DNA repair enzymes; suicide genes (thymidine kinase or cytosine deaminase); blood products; hormones; etc. (Hearing et al. U.S. Pat. No. 7,563,617).

In one preferred embodiment, the therapeutic disease associated nucleotide sequence encodes a wild type gene for which a mutant has been associated with a human disease. Such wild type genes are exemplified, but not limited to, the adenosine deaminase (ADA) gene (GenBank Accession No. M13792) associated with adenosine deaminase deficiency with severe combined immune deficiency; alpha-1-antitrypsin gene (GenBank Accession No. M11465) associated with alpha1-antitrypsin deficiency; beta chain of hemoglobin gene (GenBank Accession No. NM_000518) associated with beta thalassemia and Sickle cell disease; receptor for low density lipoprotein gene (GenBank Accession No. D16494) associated with familial hypercholesterolemia; lysosomal glucocerebrosidase gene (GenBank Accession No. 102920) associated with Gaucher disease; hypoxanthine-guanine phosphoribosyltransferase (HPRT) gene (GenBank Accession No. M26434, J00205, M27558, M27559, M27560, M27561, M29753, M29754, M29755, M29756, M29757) associated with Lesch-Nyhan syndrome; lysosomal arylsulfatase A (ARSA) gene (GenBank Accession No. NM_000487) associated with metachromatic leukodystrophy; ornithine transcarbamylase (OTC) gene (GenBank Accession No. NM_000531) associated with ornithine transcarbamylase deficiency; phenylalanine hydroxylase (PAH) gene (GenBank Accession No. NM_000277) associated with phenylketonuria; purine nucleoside phosphorylase (NP) gene (GenBank Accession No. NM_000270) associated with purine nucleoside phosphorylase deficiency; the dystrophin gene (GenBank Accession Nos. M18533, M17154, and M18026) associated with muscular dystrophy; the utrophin (also called the dystrophin related protein) gene (GenBank Accession No. NM_007124) whose protein product has been reported to be capable of functionally substituting for the dystrophin gene; and the human cystic fibrosis transmembrane conductance regulator (CFTR) gene (GenBank Accession No. M28668) associated with cystic fibrosis. In a particular embodiment, the disease associated polypeptide of interest is a cancer derived antigen such as carcino-embryonic antigen (CEA) and her2neu antigen. In a preferred embodiment, the therapeutic gene is human Factor VIII (Hearing et al. U.S. Pat. No. 7,563,617).

In a particular embodiment, the therapeutic disease associated nucleotide sequence encodes an antisense RNA or a ribozyme (Carter, U.S. Pat. No. 7,785,888). In yet another embodiment, the therapeutic disease associated nucleotide sequence is selected from the group of (i) a polynucleotide encoding a protein useful in gene therapy to relieve deficiencies caused by missing, defective or sub-optimal levels of a structural protein or enzyme; (ii) a polynucleotide that is transcribed into an anti-sense molecule; (iii) a polynucleotide that is transcribed into a decoy that binds a transcription or translation factor, (iv) a polynucleotide that encodes a cellular modulator; (v) a polynucleotide that can make a recipient cell susceptible to a specific drug; (vi) a polynucleotide for cancer therapy; and (vii) a polynucleotide that encodes an antigen or antibody. (Carter, U.S. Pat. No. 7,785,888).

In some applications, the therapeutic disease associated nucleotide sequence is selected from the group of herpes virus thymidine kinase gene, E1A tumor suppressor gene, and p53 tumor suppressor gene (Carter, U.S. Pat. No. 7,785,888). In other applications, the therapeutic disease associated nucleotide sequence encodes a protein selected from the group of cytosine deaminase (CD), herpes simplexvirus thymidine kinase (HSV-TK), DNA-binding domain (DBD) of poly(ADP-ribose) polymerase (PARP), cytotoxic protease 2A and 3C (Küpper et al., U.S. Pat. No. 7,351,697), Factor VITA, Factor VIII and Factor IX (Scaria, U.S. Pat. No. 7,307,068).

In some embodiments, the therapeutic disease associated nucleotide sequence encodes a protein selected from the group of Cystic Fibrosis Transmembrane Conductance Regulator (CFTR), coagulation factor FIX, hRPE65v2, neurotrophic factor Neurturin (NTN), and α1 antitrypsin. The FDA has approved clinical trials for gene therapy using earlier generation rAAV viruses expressing these proteins. In a particular embodiment, the therapeutic disease associated nucleotide sequence encodes a human Factor VIII (FVIII) gene (Example 1).

In one embodiment, the therapeutic nucleotide sequences contained in the invention's AAV nucleotide and amino acid sequences, as well as vectors, viruses (e.g., rAAV particles, and hybrid AAV particles such as Ad/AAV), and cells containing one or more of these sequences, comprises a therapeutic sequence that encodes an antigen polypeptide.

The terms "antigen," "immunogen," "antigenic," "immunogenic," "antigenically active," "immunologic," and "immunologically active" when made in reference to a molecule, refer to any substance that is capable of inducing a specific humoral immune response (including eliciting a soluble antibody response) and/or cell-mediated immune response (including eliciting a CTL response). In one embodiment the antigen is exemplified by Human Immunodeficiency virus gag protein, malaria circumsporozite protein ($CSP_{full}$) antigen, malaria CSP T cell epitope (SEQ ID NO:12; EYLNKIQNSLSTEWSPCSVT; U.S. Pat. No. 6,669,945), malaria CSP B Cell epitope (SEQ ID NO:13; NANPNANPNANPNANPNANPNANP; WO 2009/082440 A2), and *Pseudomonas* antigen.

In some embodiments, the antigen polypeptide is "pathogen derived," meaning expressed by a pathogen (e.g., bacteria, virus, parasite, protozoan, fungus, etc.), such as Herpes virus, *Neisseria gonorrhea*, *Treponema*, *Escherichia coli*, Respiratory Syncytial virus, tuberculosis, *Streptococcus*, *Chlamydia*, and Ebola virus. Pathogen derived antigens are exemplified by Human Immunodeficiency virus (HIV) gag protein (including the HXB2 strain gag protein (Genbank Accession #K03455), HIV Gag protein antigen such as HIV Gap protein immunodominant peptide AMQMLKETI (SEQ ID NO:14; WO 2010/051820 A1), HIV Pol protein antigen, HIV Nef protein antigen, malaria circumsporozite protein ($CSP_1$) antigen, malaria CSP T cell epitope (SEQ ID NO:12; EYLNKIQNSLSTEWSPCSVT; U.S. Pat. No. 6,669,945), malaria CSP B Cell epitope (SEQ ID NO:13; NANPNANPNANPNANPNANPNANP; WO 2009/082440 A2), and *Pseudomonas* antigen.

In a particular embodiment, the antigen comprises an epitope. The terms "epitope" and "antigenic determinant" refer to a structure on an antigen, which interacts with the binding site of an antibody or T cell receptor as a result of molecular complementarity. An epitope may compete with the intact antigen, from which it is derived, for binding to an antibody. Generally, secreted antibodies and their corresponding membrane-bound forms are capable of recognizing a wide variety of substances as antigens, whereas T cell receptors are capable of recognizing only fragments of proteins which are complexed with MHC molecules on cell surfaces. Antigens recognized by immunoglobulin receptors on B cells are subdivided into three categories: T-cell dependent antigens, type 1 T cell-independent antigens; and type 2 T cell-independent antigens. Also, for example, when a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

Exemplary epitopes include, without limitation YPYDVPDYA (SEQ ID NO:15; U.S. Pat. No. 7,255,859), EphrinA2 epitopes from renal cell carcinoma and prostate cancer (U.S. Pat. No. 7,297,337), hepatitis C virus epitopes (U.S. Pat. Nos. 7,238,356 and 7,220,420), vaccinia virus epitopes (U.S. Pat. No. 7,217,526), dog dander epitopes (U.S. Pat. No. 7,166,291), human papilloma virus (HPV) epitopes (U.S. Pat. Nos. 7,153,659 and 6,900,035), *Mycobacterium tuberculosis* epitopes (U.S. Pat. Nos. 7,037,510 and 6,991,797), bacterial meningitis epitopes (U.S. Pat. No. 7,018,637), malaria epitopes (U.S. Pat. No. 6,942,866), and type 1 diabetes mellitus epitopes (U.S. Pat. No. 6,930,181).

C. Vectors

The invention provides vectors comprising one or more of the invention's recombinant nucleotide sequences. "Vector" and "vehicle" refer to an agent that contains and/or transfers genetic material to a cell, including for example linear DNA, encapsidated virus particles, liposomes, bacteriophages, plasmids, and any combination thereof. In other embodiments, the recombinant viral vector sequence is provided in the host cells transfected with the viral vector. A vector may be used to transfer, introduce and/or insert exogenous modified genetic material (as recombinant DNA) into the genome of a recipient (host) cell. Delivery of genetic material by a "viral vector" is termed "transduction," with the infected cells described as "transduced." This process can be performed inside a living organism (in vivo) or in cell culture (in vitro and/or ex vivo). Viral based gene transfer/vectors include, for example, adenovirus, adeno-associated virus, retroviruses, alpha viruses, lentiviruses, vaccinia viruses, baculoviruses, fowl pox and herpes viruses.

Vectors (such as linear DNA, encapsidated virus particles, liposomes, bacteriophages, plasmids, etc.) may be introduced into cells using techniques well known in the art. The term "introducing" a nucleic acid sequence into a cell refers to the introduction of the nucleic acid sequence into a target cell to produce a "transformed" or "transgenic" cell. Methods of introducing nucleic acid sequences into cells are well known in the art. For example, where the nucleic acid sequence is a plasmid or naked piece of linear DNA, the sequence may be "transfected" into the cell. Alternatively, where the nucleic acid sequence is encapsidated into a viral particle, the sequence may be introduced into a cell by "transduction," i.e., the introduction of the nucleic acid sequence into the cell by "infection" with a virus containing the nucleic acid sequence, e.g., as part of a recombinant viral genome.

"Transfect" and "transfecting" refer to any mechanism by which a vector may be incorporated into a host cell. For example, where the vector is a plasmid or naked piece of linear DNA, the vector may be transfected into the cell using, for example, calcium phosphate-DNA co-precipitation, DEAE-dextran-mediated transfection, polybrene-mediated transfection, electroporation, microinjection, liposome fusion, lipofection, protoplast fusion, and biolistics. In one embodiment, successful transfection results in the capability of the host cell to express any operative genes carried by the vector. Transfections may be stable or transient. One example of a transient transfection comprises vector expression within a cell, wherein the vector is not integrated within the host cell genome. Alternatively, a stable transfection comprises vector expression within a cell, wherein the vector is integrated within the host cell genome.

Transformation of a cell with the invention's vectors may be stable or transient. The terms "transient transformation" and "transiently transformed" refer to the introduction of one or more nucleotide sequences of interest into a cell in the absence of integration of the nucleotide sequence of interest into the host cell's genome. Transient transformation may be detected by, for example, enzyme-linked immunosorbent assay (ELISA) that detects the presence of a polypeptide encoded by one or more of the nucleotide sequences of interest. Alternatively, transient transformation may be detected by detecting the activity of the protein encoded by the nucleotide sequence of interest. The term "transient transformant" refer to a cell that has transiently incorporated one or more nucleotide sequences of interest. ¶ In contrast, the terms "stable transformation" and "stably transformed" refer to the introduction and integration of one or more nucleotide sequence of interest into the genome of a cell. Thus, a "stable transformant" is distinguished from a transient transformant in that, whereas genomic DNA from the stable transformant contains one or more heterologous nucleotide sequences of interest, genomic DNA from the transient transformant does not contain the heterologous nucleotide sequence of interest. Stable transformation of a cell may be detected by Southern blot hybridization of genomic DNA of the cell with nucleic acid sequences that are capable of binding to one or more of the nucleotide sequences of interest. Alternatively, stable transformation of a cell may also be detected by the polymerase chain reaction of genomic DNA of the cell to amplify the nucleotide sequence of interest.

"Gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In some embodiments, the invention's recombinant nucleotide sequence is comprised in an expression vector. Thus, in a particular embodiment, the invention provides expression vectors comprising a) one or more of the recombinant nucleotide sequences described herein, and b) a heterologous polynucleotide sequence operably linked to a first AAV ITR. The recombinant nucleotide sequence of the invention's expression vectors is exemplified by, but not limited to, a sequence encoding a chimeric protein, a) wherein the encoded chimeric protein i) comprises at least a portion of wild type AAV Rep inhibitory amino acid sequence listed as SEQ ID NO:20 (i.e., encoded by the 564-bp DNA sequence from bp 1623 to bp 2186 of the AAV2 genome) and/or SEQ ID NO:02 (i.e., encoded by the 135-bp DNA sequence from bp 1782 to bp 1916 of the AAV2 genome, FIG. 4 panel B), and ii) has Rep-mediated nuclease activity, and b) wherein the recombinant nucleotide sequence comprises a scrambled polynucleotide sequence encoding the at least a portion of the wild type AAV Rep inhibitory amino acid sequence listed as SEQ ID NO:20 and/or SEQ ID NO:02. In a particular embodiment the heterologous polynucleotide sequence is flanked by the first AAV ITR and by a second AAV ITR.

The term "expression vector" as used herein refers to a nucleotide sequence containing a desired coding sequence and appropriate nucleic acid sequences necessary for the expression (i.e., transcription into RNA and/or translation into a polypeptide) of the operably linked coding sequence in a particular host cell. Expression vectors are exemplified by, but not limited to, plasmid, phagemid, shuttle vector, cosmid, virus, chromosome, mitochondrial DNA, plastid DNA, and nucleic acid fragments thereof. Nucleic acid sequences used for expression in prokaryotes include a promoter, optionally an operator sequence, a ribosome binding site and possibly other sequences. Eukaryotic cells are known to utilize promoters, enhancers, and termination and polyadenylation signals. Expression vectors include "gene therapy viral vectors," viral vectors comprising a therapeutic nucleotide sequence.

In a particular embodiment, the expression vector is a viral vector, as exemplified by, but not limited to a gene therapy viral vector.

In another particular embodiment, the invention's expression vectors contain the scrambled polynucleotide sequence that encodes at least a portion of the wild type AAV Rep inhibitory amino acid sequence, in operable combination with a promoter.

The term "promoter," "promoter element," or "promoter sequence" as used herein, refers to a DNA sequence that, when ligated to a nucleotide sequence of interest, is capable of controlling the transcription of the nucleotide sequence of interest into mRNA. The terms "control," "drive," "regulate," and "facilitate" when used in reference to a promoter are interchangeably used to refer to the activity of the promoter in bringing about and/or altering the level of transcription of an operably linked nucleotide sequence. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

Promoters may be inducible or constitutive. "Inducible" and "regulatable" promoter interchangeably refer to a promoter that is capable of directing a level of transcription of an operably linked nucleic acid sequence in the presence of a stimulus (e.g., heat shock, chemicals, etc.) that is different from the level of transcription of the operably linked nucleic acid sequence in the absence of the stimulus. Inducible promoters are exemplified by lac, tac, trc, ara, trp, λ phage, T7 phage, and T5 phage promoter, and tetracycline inducible promoters. In a particularly preferred embodiment, the inducible promoter is a tetracycline inducible promoter (Example 2).

"Constitutive" promoter means that the promoter is capable of directing transcription of an operably linked nucleic acid sequence in the absence of a stimulus (e.g., heat shock, chemicals, etc.). Constitutive promoters are exemplified by vaccinia virus p7.5 promoter. Gene transcription in viruses (such as poxvirus) is temporally regulated, and therefore contain promoters for early, intermediate, and late gene expression. Certain virus (e.g., poxvirus) genes are expressed constitutively, and promoters for these "early-late" genes bear hybrid structures. Synthetic early-late promoters have also been developed. See Hammond J. M., et al., J. Virol. Methods 66:135-8 (1997); Chakrabarti S., et al., Biotechniques 23:1094-7 (1997). Examples of early promoters include the 7.5-kD promoter (also a late promoter), the DNA pol promoter, the tk promoter, the RNA pol promoter, the 19-kD promoter, the 22-kD promoter, the 42-kD promoter, the 37-kD promoter, the 87-kD promoter, the H3' promoter, the H6 promoter, the D1 promoter, the D4 promoter, the D5 promoter, the D9 promoter, the D12 promoter, the 13 promoter, the M1 promoter, and the N2 promoter. See, e.g., Moss, B., "Poxviridae and their Replication" IN Virology, 2d Edition, B. N. Fields, D. M. Knipe et al., Eds., Raven Press, p. 2088 (1990). Example of late promoters include the 7.5-kD promoter, the MIL promoter, the 37-kD promoter, the 11-kD promoter, the 11L promoter, the 12L promoter, the 13L promoter, the 15L promoter, the 17L promoter, the 28-kD promoter, the H1L promoter, the H3L promoter, the H5L promoter, the H6L promoter, the H8L promoter, the D11L promoter, the D12L promoter, the D13L promoter, the A1L promoter, the A2L promoter, the A3L promoter, and the P4b promoter. See, e.g., Moss, B., "Poxviridae and their Replication" IN Virology, 2d Edition, B. N. Fields, D. M. Knipe et al., Eds., Raven Press, p. 2090 (1990). Additional constitutive promoters include the human U1-1 small nuclear RNA promoter (pHU-1). In a particularly preferred embodiment, the constitutive promoter is the human U1-1 small nuclear RNA promoter (pHU-1) (Example 4).

D. Viruses

In one particular embodiment, the invention provides recombinant viruses (e.g., rAAV, and hybrid AAV viruses) comprising one or more of the invention's AAV recombinant nucleotide sequences. In particular, the invention provides recombinant viruses comprising an AAV recombinant nucleotide sequence encoding a chimeric; protein, a) wherein the encoded chimeric protein i) comprises at least a portion of wild type AAV Rep inhibitory amino acid sequence listed as SEQ ID NO:20 (i.e., encoded by the 564-bp DNA sequence from bp 1623 to bp 2186 of the AAV2 genome) and/or SEQ ID NO:02 (i.e., encoded by the 135-bp DNA sequence from bp 1782 to bp 1916 of the AAV2 genome, FIG. 4 panel B), and ii) has Rep-mediated nuclease activity, and b) wherein the recombinant nucleotide sequence comprises a scrambled polynucleotide sequence encoding the wild type AAV Rep inhibitory amino acid sequence listed as SEQ ID NO:20 and/or SEQ ID NO:02 (and/or portion thereof).

Methods for production of the invention's rAAV vectors and AAV containing these vectors are known in the art (Carter, U.S. Pat. No. 7,785,888) and described herein (Example 1).

For example, methods for achieving high titers of rAAV virus preparations that are substantially free of contaminating virus and/or viral or cellular proteins are outlined by Atkinson et al. in WO 99/11764. Techniques described therein can be employed for the large-scale production of rAAV viral particle preparations (Carter, U.S. Pat. No. 7,785,888).

These various examples address the production of rAAV viral particles at sufficiently high titer, minimizing recombination between rAAV vector and sequences encoding packaging components, and producing rAAV virus preparations that are substantially free of contaminating virus and/or viral or cellular protein (Carter, U.S. Pat. No. 7,785,888).

Optionally, rAAV virus preparations can be further processed to purify (i.e., enrich for) rAAV particles and/or otherwise render them suitable for administration to a subject. See Atkinson et al. for exemplary techniques (WO 99/11764). Purification techniques can include isopynic gradient centrifugation, and chromatographic techniques. Reduction of infectious helper virus activity can include inactivation by heat treatment or by pH treatment as is known in the art. Other processes can include concentration, filtration, diafiltration, or mixing with a suitable buffer or pharmaceutical excipient. Preparations can be divided into unit dose and multi dose aliquots for distribution, which will retain the essential characteristics of the batch, such as the homogeneity of antigenic and genetic content, and the relative proportion of contaminating helper virus (Carter, U.S. Pat. No. 7,785,888).

Various methods for the determination of the infectious titer of a viral preparation are known in the art. For example, one method for titer determination is a high-throughput titering assay as provided-by Atkinson et al. (WO 99/11764). Virus titers determined by this rapid and quantitative method closely correspond to the titers determined by more classical techniques. In addition, however, this high-throughput method allows for the concurrent processing and analysis of many viral replication reactions and thus has many others uses, including for example the screening of cell lines permissive or non-permissive for viral replication and infectivity (Carter, U.S. Pat. No. 7,785,888).

In one embodiment, the invention's recombinant viruses (e.g., rAAV, and hybrid AAV viruses) comprise a heterologous polynucleotide sequence operably linked to a first AAV ITR. In a particular embodiment, heterologous polynucleotide sequence is flanked by the first AAV ITR and by a second AAV ITR.

In yet another embodiment, the invention's recombinant viruses (e.g., rAAV, and hybrid AAV viruses) further comprise a nucleic acid sequence encoding AAV Cap In particular embodiments, the invention's recombinant viruses (e.g., rAAV, and hybrid AAV viruses) are characterized by one or more of the following properties and/or functions, including, being infectious, begin replication competent, being productive, being produced at substantially the same copy number as in the absence of AAV Rep protein expression, being capable of site-specific integration, expressing Rep78 protein and/or Rep68 protein at reduced levels compared to virus containing wild type AAV Rep inhibitory nucleotide sequence.

For example, the invention's viruses are infectious. Data herein demonstrate productive infection that generated infectious virus that is replication competent, using clone pAd/sRep78 (containing a scrambled Rep78 sequence) and clone pAd/dRep78 (containing a deoptimized Rep78 sequence), that formed CPE in transfected HEK 293 packaging cells (Example 3).

In another example, the invention's infectious viruses are replication competent. Data herein demonstrate productive infection that generated infectious virus that is replication competent, using clone pAd/sRep78 (containing a scrambled Rep78 sequence) and clone pAd/dRep78 (containing a deoptimized Rep78 sequence), that formed CPE in transfected HEK 293 packaging cells (Example 3).

In a further example, the invention's replication competent viruses are productive. Data herein demonstrate productive infection that generated infectious virus that is replication competent, using clone pAd/sRep78 (containing a scrambled Rep78 sequence) and clone pAd/dRep78 (containing a deoptimized Rep78 sequence), that formed CPE in transfected HEK 293 packaging cells (Example 3).

In another example, the copy number of the invention's viruses is produced by a permissive cell at substantially the same copy number as a the copy number of a control virus that lacks expression of AAV Rep protein. Data herein demonstrate that the copy numbers of adenovirus AdsRep78 (containing a scrambled Rep78 sequence) and adenovirus AddRep78 (containing a deoptimized Rep78 sequence) that were produced by HEK 293 cells were substantially the same to each other, and to a control adenovirus Ad/AAVFVIII (which carries coagulation FVIII flanked by the AAV ITR in the absence of a Rep expression cassette) (Example 3). Furthermore, data herein also show that production of both adenovirus AdsRep78 and adenovirus AddRep78 could be scaled up with yields comparable to each other and to Ad/AAVFVIII (Example 3, Table 1).

In a further example, the invention's viruses are characterized by site-specific integration of heterologous nucleotide sequences that they contain into the adeno-associated virus integration site 1 (AAVS1) sequence of a host cell. In some embodiments, however, where delivery of a heterologous nucleotide sequences is desired without site-specific integration, this may be accomplished using AAV.

In one particular example, the invention's viruses express Rep78 protein SEQ ID NO:04 (or a functional portion thereof) at a reduced level compared to the level expressed by a control hybrid virus that comprises a wild type amino acid sequence SEQ ID NO:20 and/or SEQ ID NO:02 that is encoded by the wild type AAV Rep inhibitory nucleotide sequence listed as SEQ ID NO:17 and/or SEQ ID NO:01, respectively. For example, data herein demonstrate that the deoptimized Rep78 nucleotide sequence, which uses codons in underrepresented pairs, expressed Rep78 protein at reduced levels compared to wild type Rep78 nucleotide sequence due to codon pair bias. Utilization of underrepresented codon pairs resulted in an ORF that is expressed at reduced levels.

i. rAAV

Thus, in one embodiment, the invention's virus is a "recombinant adeno-associated virus" ("rAAV") containing one or more of the invention's sequences. rAAV are widely used as gene transfer vehicles today, capable of long term extra chromosomal persistence in several tissues. Production of rAAV [requires AAV ITR flanked transgene, AAV Rep and Cap genes and helper virus. rAAV do not carry Rep due to size constraints and worries about toxicity and are therefore incapable of site-specific integration. The only AAV elements retained are the AAV ITRs which flank the transgene of interest. Currently, production of rAAV requires co-transfection of multiple plasmid constructs, bearing the AAV ITR flanked transgene construct, the AAV Rep-Cap coding sequences and the Adenovirus helper functions including E2,E4 and VA into cell lines such as 293 which provide Ad E1 functions or infection of producer cell lines carrying an integrated Rep Cap cassette and the rAAV sequence, with a helper Ad.

The FDA has approved clinical trial, for rAAV vectors expressing the Cystic Fibrosis Transmembrane Conductance Regulator (rAAV2-CFTR) (Flotte (1996) *Hum. Gene Ther.* 7:1145-1159; Flotte et al. (2003) *Hum Gene Ther* 14(11): 1079-1088), rAAV2-FIX for the delivery of coagulation FIX to patients with Hemophilia B (Manno et al. (2003) *Blood* 101(8):2963-2972; Manno et al. (2006) *Nat Med* 12(3):342-347), rAAV2-hRPE65v2 vectors for expression of RPE65 in the treatment of Leber's congenital Amaurosis (LCA) (Bennicelli et al. (2008) *Mol Ther* 16(3):458-465), rAAV vector CERE-20 expressing the neurotrophic factor Neurturin (NTN) to protect against the degeneration of dopaminergic neurons associated with Parkinson's disease, and rAAV2 vector expressing al antitrypsin for al antitrypsin (AAT) deficiency associated lung disease (Brantly et al. (2009) *PNAS* 106(38):16363-16368; Mingozzi et al. (2009) *Blood* 114(10):2077-2086).

ii. Hybrid Viruses

In another embodiment, the invention's virus is a hybrid virus that comprises the invention's AAV sequences and at least a portion of a heterologous virus genome sequence. In a particular embodiment, the heterologous virus genome sequence is gutted. The term "gutted" and "fully deleted" are used interchangeably in reference to a viral vector, and refer to a viral vector (e.g., naked DNA, plasmid, virus particle, etc.) that lacks all the coding sequences that are otherwise present in a wild type virus. Gutted vectors may contain non-coding viral sequences, e.g., terminal repeat sequences, and packaging sequences. For example, a gutted adenovirus vector lacks all adenovirus coding sequences and optionally contains adenovirus terminal repeat sequences and/or packaging sequences (e.g., U.S. Pat. No. 5,994,132 to Chamberlain et al., U.S. Pat. No. 6,797,265 to Amalfitano et al., U.S. Pat. No. 7,563,617 to Hearing et al., and U.S. Pat. No. 6,262,035 to Campbell et al.). Gutted vectors are preferred in certain embodiments since they do not express viral vector proteins and hence do not induce an adverse immune or toxic response in a cell.

While not intending to limit the source or type of heterologous virus whose genome sequences are included the invention's a hybrid viruses, in one embodiment, the heterologous virus is exemplified by, but not limited to, adenovirus, herpes simplex virus, retrovirus, lentivirus, and baculovirus.

a. Hybrid Adenovirus

Thus in a particular embodiment, the hybrid virus comprises at least a portion of adenovirus genome. "Adenovirus" refers to a double-stranded DNA virus with a genome of approximately 36 Kb flanked by inverted terminal repeats. Adenovirus boasts of a wide tropism which can be increased by replacement of the fiber knob carried on the icosahedral capsid, responsible for contact with the host receptor, with that of another serotype. Adenovirus is of animal origin, such as avian, bovine, ovine, murine, porcine, canine, simian, and human origin. Avian adenoviruses are exemplified by serotypes 1 to 10 that are available from the ATCC, such as, for example, the Phelps (ATCC VR 432), Fontes (ATCC VR 280), P7 A (ATCC VR 827), IBH 2A (ATCC VR 828), J2 A (ATCC VR 829), T8 A (ATCC VR 830), and K 11 (ATCC VR 921) strains, or else the strains designated as ATCC VR 831 to 835. Bovine adenoviruses are illustrated by those available from the ATCC (types 1 to 8) under reference numbers ATCC VR 313, 314, 639 642, 768 and 769. Ovine adenoviruses include the type 5 (ATCC VR 1343) or type 6 (ATCC VR 1340). Murine adenoviruses are exemplified by FL (ATCC VR 550) and E20308 (ATCC VR 528). Porcine adenovirus (5359) may also be used. adenoviruses of canine origin include all the strains of the CAVI and CAV2 adenoviruses [for example, Manhattan strain or A26/61 (ATCC VR 800) strain]. Simian adenoviruses are also contemplated, and they include the adenoviruses with the ATCC reference numbers VR 591 594, 941 943, and 195 203. Human adenoviruses, of which there greater than fifty (50) serotypes are known in the art, are also contemplated, including Ad2, Ad3, Ad4, Ad5, Ad11, Ad14, Ad7, Ad9, Ad12, Ad16, Ad17, Ad21, Ad26, Ad34, Ad35, Ad 40, Ad48, Ad49, Ad50 (e.g., U.S. Pat. No. 7,300,657 to Pau, U.S. Pat. No. 7,468,181 to Vogels, and U.S. Pat. No. 6,136,594 to Dalemans). In one preferred embodiment, the adenovirus is selected from adenovirus 2 (Ad2) and adenovirus 5 (Ad5).

Adenoviruses of animal origin can be obtained, for example, from strains deposited in collections, then amplified in competent cell lines and modified as required (Hearing et al., U.S. Pat. No. 7,563,617). Techniques for producing, isolating and modifying adenoviruses have been described in the literature and may be used within the scope of the present invention [Akli et al., Nature Genetics 3 (1993) 224; Stratford-Perricaudet et al., Human Gene Therapy 1 (1990) 241; patent EP 185 573, Levrero et al., Gene 101 (1991) 195; Le Gal la Salle et al., Science 259 (1993) 988; Roemer and Friedmann, Eur. J. Biochem. 208 (1992) 211; Dobson et al., Neuron 5 (1990) 353; Chiocca et al., New Biol. 2 (1990) 739; Miyanohara et al., New Biol. 4 (1992) 238; WO 91/18088, WO 90/09441, WO 88/10311, WO 91/11525]. These different viruses can then be modified, for example, by deletion, substitution, addition, etc. The complete genome sequences have been determined for human adenovirus type 2 (GenBank Accession No. J01917), human adenovirus type 5 (GenBank Accession No. M73260; and GenBank Accession No. NC-001406), human adenovirus type 12 (GenBank Accession No. NC-001460, X73487); human adenovirus type 17 (GenBank Accession No. NC-002067, AF108105), and human adenovirus type 40 (GenBank Accession No. L19443).

Adenovirus vectors have been used in gene therapy, particularly cancer therapy. e.g., vector ONYX015 (Heise C (1997) Nature Med. 3:639-645; Rothmann et al. (1998) J. Virol. 72:9470).

Adenovirus vectors have also been used as Ad-based vaccines for multiples diseases including Tuberculosis (Magalhaes et al. (2008) PLoS ONE 3:e3790), malaria (Shoff et al. (2008) Vaccine 26:2818-2823), rabies (Zhou et al. (2006) Mol Ther 14:662-672), influenza (Hoelscher et al. (2008) J Infect Dis 197:1185-1188), and leishmania (Resende et al. (2008) Vaccine 26:4585-4593).

"Adenovirus early gene regions" refers to nucleotide sequences which are derived from adenovirus and which are transcribed prior to replication of the adenovirus genome. The early gene regions comprise E1a, E1b, E2a, E2b, E3 and E4. The E1a gene products are involved in transcriptional regulation; the E1b gene products are involved in the shut-off of host cell functions, mRNA transport, regulation of apoptosis induction, and inhibition of p53 tumor suppressor. Eta encodes a DNA-binding protein (DBP); E2b encodes the viral DNA polymerase and preterminal protein (pTP). The E3 gene products are not essential for viral growth in cell culture. The E4 regions encode regulatory proteins involved in transcriptional and post-transcriptional regulation of viral gene expression; a subset of the E4 proteins are essential for viral growth. In contrast to the adenovirus early gene regions, the "adenovirus late gene regions" refers to adenovirus nucleotide sequences that are transcribed after replication. The products of the late genes (e.g., L1-5) are predominantly components of the virion as well as proteins involved in the assembly of virions. The VA genes produce VA RNAs that block the host cell from shutting down viral protein synthesis. The early and late gene regions of adenovirus have been characterized (e.g., in Ad2 genomic sequence; GenBank No. J01917).

In a more particular embodiment, the hybrid virus expresses a functional AAV Rep protein (such as Rep78 and/or Rep68). Data herein demonstrate the ability of Ad/dRep78 and Ad/sRep78 to produce functional Rep78 as confirmed by an excision assay which depends on Rep's ability to cleave at a folded AAV ITR (Example 3).

In a more particular embodiment, the adenovirus lacks one or more adenovirus early gene region. This is exemplified by adenovirus that lacks adenovirus E1 gene coding sequence (Example 2), and/or lacks adenovirus E3 gene coding sequence. To illustrate, Example 4 shows that in spite of expressing far higher levels of Rep78 than the tetracycline inducible system, the invention's ΔE1ΔE3 adenoviruses carrying the hu1-sRep78 and hu1-dRep78 constructs were still capable of normal rates of replication, and CPE.

b. Hybrid Herpes Simplex Virus

In another particular embodiment, the hybrid virus comprises at least a portion of herpes simplex virus, such as, without limitation, HSV-1 and HSV-2. "Herpes simplex virus" also referred to as "HSV", is an enveloped virus with a linear double stranded DNA (dsDNA) genome of 152 Kb, carrying 74 separate genes. The genome consists of 2 unique sequences, one longer than the other ($U_L$ and $U_S$). Each of these sequences are flanked by inverted terminal repeat sequences—with $U_L$ flanked by Terminal Repeat ($TR_L$) and Internal Repeat ($IR_L$) and $U_S$ being flanked by $IR_S$ and $TR_S$. Copies of an 'a' sequence carrying packaging signals lie between the two IRs and at each TR. HSV is exemplified by HSV-1 and HSV-2, which are neurotropic pathogens associated with a number of skin diseases from herpes labialis and herpes genitalis to the life threatening neonatal herpes and herpes encephalitis (Watanabe D (2010) *Journal of Dermatological Science* 57(2):75-82).

Generic methods are known for producing oncolytic HSV based vectors and DNA vaccines. The two main types of HSV based vectors used are amplicon vectors and replication attenuated vectors.

Amplicon vectors are plasmids made up of repeated units of the transgene, a packaging signal (pac) and an HSV origin of replication (R. R. S & N. F (1982) *Cell* 30:295). When introduced into a cell along with HSV helper functions, these amplicons replicate and are packaged as head to tail concatemers into infectious HSV virions. HSV Amplicons have been used as DNA vaccines (Santos et al. (2006) *Curr Gene Ther* 6(3):383-392).

Replication attenuated HSV vectors have been used as oncolytic vectors. These vectors have deletions in genes (such as HSV-TK and HSV-RR) that are required for replication of the virus in non-dividing cells and are thus capable of replication only in dividing (tumor) cells. Clinical trials (Phase I) for multiple HSV-1 derived oncolytic viruses for colorectal carcinoma (Kemeny N, et al. (2006) *Hum Gene Ther* 17(12):1214-1224), melanoma (MacKie et al. (2001) *Lancet* 357(9255):525-526), breast cancer (Hu et al. (2006) *Clin Cancer Res* 12(22):6737-6747), and malignant glioma (Markert et al. (2000) *Gene Ther* 7(10):867-874), among others have been reported. All studies reported safety and toleration of HSV vectors.

In another particular embodiment, the hybrid virus comprises at least a portion of a retrovirus. "Retrovirus" is a small enveloped RNA virus, containing two identical single stranded positive sense RNA genomes enclosed in an enveloped capsid. Retroviruses have a genome flanked by Long Terminal Repeats (LTR) and 4 main genes gag, poi, pro and env.

c. Hybrid Lentivirus

In a further embodiment, the embodiment, the hybrid virus comprises at least a portion of a lentivirus. "Lentiviruses" are a group of complex retroviruses that carry accessory gene which regulate and coordinate viral gene expression. Lentiviruses also differ from other retroviruses in their ability to infect non-dividing cells as most other retroviruses are incapable of traversing the nuclear membrane and can thus infect only dividing cells where the nuclear membrane is dissolved.

d. Hybrid Baculovirus

In another embodiment, the hybrid virus comprises at least a portion of a baculovirus. "Baculoviruses" are a family of large rod-shaped viruses that can be divided to two genera: nucleopolyhedroviruses (NPV) and granuloviruses (GV). While GVs contain only one nucleocapsid per envelope, NPVs contain either single (SNPV) or multiple (MNPV) nucleocapsids per envelope. The enveloped virions are further occluded in granulin matrix in GVs and polyhedrin for NPVs. Moreover, GV have only single virion per granulin occlusion body while polyhedra contains multiple embedded virions. Baculoviruses have very species-specific tropisms among the invertebrates with over 600 host species having been described. They are not known to replicate in mammalian or other vertebrate animal cells. Baculoviruses contain circular double-stranded genome ranging from 80-180 kbp.

Baculovirus expression in insect cells represents a robust method for producing recombinant glycoproteins. Baculovirus-produced proteins have several immunologic advantages over proteins derived from mammalian sources and are attractive candidates for therapeutic cancer vaccines (Betting et al., Enhanced immune stimulation by a therapeutic lymphoma tumor antigen vaccine produced in insect cells involves mannose receptor targeting to antigen presenting cells. Vaccine. 2009 Jan. 7; 27(2):250-9. Epub 2008 Nov. 8. PMID: 19000731).

E. Cells

The rAAV vector construct, and the complementary packaging gene constructs can be implemented in this invention in a number of different forms. Generic methods are known for introducing rAAV particles, plasmids, and stably transformed host cells into cells (e.g., packaging cell) either transiently or stably (Carter, U.S. Pat. No. 7,785,888).

Cells may be contacted with the recombinant viral vectors (e.g. rAAV) and AAV viral particles of the invention "in vivo," "in vitro," "ex vivo," and any combination thereof. As used herein, the term "in vitro" refers to an artificial environment and to processes or reactions that occur within an artificial environment. In vitro environments are exemplified, but not limited to, controlled laboratory conditions such as test tubes, culture plates, culture wells, etc. The term "in vivo" refers to the natural environment (e.g., within an organism or a cell) and to processes or reactions that occur within that natural environment. The term "ex vivo" refers to an environment wherein the cell is removed from, and manipulated outside, an organism and/or tissue.

A variety of different genetically altered cells can thus be used in the context of this invention. By way of illustration, a mammalian host cell may be used with at least one intact copy of a stably integrated rAAV vector. An AAV packaging plasmid comprising at least an AAV rep gene operably linked to a promoter can be used to supply replication functions (U.S. Pat. No. 5,658,776). Alternatively, a stable mammalian cell line with an AAV rep gene operably linked to a promoter can be used to supply replication functions (see, e.g., Trempe et al., U.S. Pat. No. 5,837,484; Burstein et al., WO 98/27207; and Johnson et al., U.S. Pat. No. 5,658,785). The AAV cap gene, providing the encapsidation proteins as described above, can be provided together with an AAV rep gene or separately (see, e.g., the above-referenced applications and patents as well as Allen et al. (WO 96/17947). Other combinations are possible (Carter, U.S. Pat. No. 7,785,888).

As is described in the art, and illustrated herein, genetic material can be introduced into cells (such as mammalian "producer" cells for the production of rAAV) using any of a variety of means to transform or transduce such cells. By way of illustration, such techniques include, but are not limited to, transfection with bacterial plasmids, infection with viral vectors, electroporation, calcium phosphate precipitation, and introduction using any of a variety of lipid-based compositions (a process often referred to as "lipofection"). Methods and compositions for performing these techniques have been described in the art and are widely available (Carter, U.S. Pat. No. 7,785,888).

Once the host cell is provided with the requisite elements, the cell is cultured under conditions that are permissive for the replication of AAV, to allow replication and packaging of the rAAV vector. rAAV particles are then collected, and isolated from the cells used to prepare them (Carter, U.S. Pat. No. 7,785,888).

Selection of cells containing the invention's vectors and/or viruses may be conducted by any technique in the art. For example, the polynucleotide sequences used to alter the cell may be introduced simultaneously with or operably linked to one or more detectable or selectable markers as is known in the art. By way of illustration, one can employ a drug resistance gene as a selectable marker. Drug resistant cells can then be picked and grown, and then tested for expression of the desired sequence (i.e., a product of the heterologous polynucleotide). Testing for acquisition, localization and/or maintenance of an introduced polynucleotide can be performed using DNA hybridization-based techniques (such as Southern blotting and other procedures as known in the art). Testing for expression can be readily performed by Northern analysis of RNA extracted from the genetically altered cells, or by indirect immunofluorescence for the corresponding gene product. Testing and confirmation of packaging capabilities and efficiencies can be obtained by introducing to the cell the remaining functional components of AAV and a helper virus, to test for production of AAV particles. (Carter, U.S. Pat. No. 7,785,888).

In one embodiment to packaging rAAV vectors in an AAV particle, the rAAV vector sequence (i.e., the sequence flanked by AAV ITRs), and the AAV packaging genes to be provided in trans, are introduced into the host cell in separate bacterial plasmids (Carter, U.S. Pat. No. 7,785,888).

A second embodiment is to provide either the rAAV vector sequence, or the AAV packaging genes, in the form of an episomal plasmid in a mammalian cell used for AAV replication. See, for example, U.S. Pat. No. 5,173,414 and Carter, U.S. Pat. No. 7,785,888.

F. Vaccines

The invention provides compositions (such as vaccines) comprising the invention's AAV nucleotide and amino acid sequences, vectors, viruses and/or cells. In one embodiment, the composition is free of helper virus. In another embodiment, the composition is a vaccine. The term "vaccine" refers to a pharmaceutically acceptable preparation that may be administered to a host to induce a humoral immune response (including eliciting a soluble antibody response) and/or cell-mediated immune response (including eliciting a cytotoxic T lymphocyte (CTL) response).

In one embodiment, the composition further comprises a pharmaceutically acceptable compound such as diluent, carrier, excipient, and/or adjuvant.

The terms "pharmaceutically acceptable," "pharmaceutical" and "physiologically tolerable" refer to a composition that contains molecules that are capable of administration to or upon a subject and that do not substantially produce an undesirable effect such as, for example, adverse or allergic reactions, dizziness, gastric upset, toxicity and the like, when administered to a subject. Preferably also, the pharmaceutically acceptable molecule does not substantially reduce the activity of the invention's compositions. Pharmaceutical molecules include, but are not limited to excipients and diluents. Vaccines may contain pharmaceutically acceptable adjuvants, diluents, carriers, and/or excipients.

The term "adjuvant" as used herein refers to any compound which, when injected together with an antigen, non-specifically enhances the immune response to that antigen. Exemplary adjuvants include Complete Freund's Adjuvant, Incomplete Freund's Adjuvant, Gerbu adjuvant (GMDP; C.C. Biotech Corp.), RIBI fowl adjuvant (MPL; RIBI Immunochemical Research, Inc.), potassium alum, aluminum phosphate, aluminum hydroxide, QS21 (Cambridge Biotech), Titer Max adjuvant (CytRx), and Quil A adjuvant. Other compounds that may have adjuvant properties include binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

Exemplary "diluents" include water, physiological saline solution, human serum albumin, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

Exemplary "carriers" include liquid carriers (such as water, saline, culture medium, saline, aqueous dextrose, and glycols) and solid carriers (such as carbohydrates exemplified by starch, glucose, lactose, sucrose, and dextrans, antioxidants exemplified by ascorbic acid and glutathione, and hydrolyzed proteins.

The term "excipient" refers herein to any inert substance (e.g., gum arabic, syrup, lanolin, starch, etc.) that forms a vehicle for delivery of an antigen. The term excipient includes substances that, in the presence of sufficient liquid, impart to a composition the adhesive quality needed for the preparation of pills or tablets.

G. Exemplary Applications of the Invention's Compositions for Identification of Functional Portions of Wild Type AAV Rep Inhibitory Nucleotide Sequences The invention's compositions may be used to identify functional portions of the wild type AAV Rep inhibitory nucleotide sequence listed as SEQ ID NO:17 and/or SEQ ID NO:01, i.e., portions that reduce replication and/or infection and/or productive infection by a virus.

In a first embodiment, the method utilizes a scrambled AAV Rep inhibitory nucleotide sequence (exemplified by, but not limited to, SEQ 1D NO:18 and/or SEQ ID NO:07 and/or portion thereof). In a second embodiment, the method utilizes a portion of the wild type AAV Rep inhibitory nucleotide sequence listed as SEQ ID NO:17 and/or SEQ ID NO:01.

i. Methods Employing Scrambled Sequences

Thus, in a first embodiment, the invention provides methods for detecting a sequence that reduces replication and/or infection and/or productive infection by a virus, comprising a) providing i) a first expression vector comprising a first nucleotide sequence comprising a scrambled polynucleotide sequence encoding a portion of wild type AAV Rep inhibitory amino acid sequence listed as SEQ ID NO:20 and/or SEQ ID NO:02, ii) a second expression vector comprising a second nucleotide sequence, wherein the second nucleotide sequence is produced by substituting a portion of the scrambled polynucleotide sequence with a corresponding portion of wild type AAV Rep inhibitory nucleotide sequence listed as SEQ ID NO:17 and/or SEQ ID NO:01, and iii) a host cell that is permissive for the virus, b) transfecting i) the first expression vector into the permissive cell under conditions to produce a first virus that comprises a first amino acid sequence encoded by the first nucleotide sequence, and ii) the second expression vector into the permissive cell under conditions to produce a second virus that comprises a second amino acid sequence encoded by the second nucleotide sequence, and c) detecting reduced replication and/or infection and/or productive infection of the permissive cell by the second virus compared to the first virus, wherein the detecting indicates that the portion of wild type AAV Rep inhibitory nucleotide sequence reduces replication and/or infection and/or productive infection by the virus. While not necessary, it may be desirable that the detecting step comprises, after the transfecting step, isolating one or more of i) the first virus, and ii) the second virus.

The invention's methods are exemplified by S (wt3) Rep (FIG. 3A) produced in Example 5, with S (wt3) Rep in which a 564 bp portion of a scrambled Rep78 ORF was substituted with bp 1623 to bp 2186 bp of the AAV2 genome corresponding to C-terminal third of the wild type Rep ORF, and which showed no replication, thus demonstrating that an AAV Rep inhibitory nucleotide sequence was localized within the 3' 564 base pairs, in the region encompassing bp 1623 to bp 2186 of the AAV2 genome. A similar approach was used with respect to Ad/Rep I (FIG. 3B), to further narrow the location of the AAV Rep inhibitory nucleotide sequence to the 135-bp sequence from bp 1782 to bp 1916 of the AAV2 genome, FIG. 4 (Example 5).

ii. Methods Employing Wild Type Sequences

In a second embodiment, the invention provides methods for detecting a sequence that reduces replication and/or infection and/or productive infection by a virus, comprising a). providing i) a first expression vector comprising a first nucleotide sequence comprising a portion of wild type AAV Rep inhibitory nucleotide sequence listed as SEQ ID NO:17 and/or SEQ ID NO:01, ii) a second expression vector comprising a second nucleotide sequence, wherein the second nucleotide sequence is produced by substituting the portion of the wild type AAV Rep inhibitory nucleotide sequence with a scrambled polynucleotide sequence encoding the portion of the wild type AAV Rep inhibitory nucleotide sequence, and iii) a host cell that is permissive for the virus, b) transfecting i) the first expression vector into the permissive cell under conditions to produce a first virus that comprises a first amino acid sequence encoded by the first nucleotide sequence, and ii) the second expression vector into the permissive cell under conditions to produce a second virus that comprises a second amino acid sequence encoded by the second nucleotide sequence, c) detecting increased replication and/or infection and/or productive infection of the permissive cell by the second virus compared to the first virus, wherein the detecting indicates that the portion of the wild type AAV Rep inhibitory nucleotide sequence reduces replication and/or infection and/or productive infection by the virus.

While not necessary, it may be desirable that the detecting step comprises, after the transfecting step, isolating one or more of i) the first virus, and ii) the second virus.

The invention's methods are exemplified by the virus produced in Example 5, with S (wt1,2) Rep (FIG. 3A) in which a 555 bp portion encompassing bp 1623 to bp 2186 bp of the AAV2 genome corresponding to ~C-terminal third of the wild type Rep ORF was substituted with a corresponding scrambled sequence, and which showed that modification of these 564 bp portion of the wild type sequence with scrambled Rep sequences, alone, was sufficient to lift inhibition of productive infection, and allow replication of the adenovirus carrying it, comparable to Ad/sRep78 that contained an entirely scrambled sequence of wild type AAV Rep78.

H. Exemplary Applications of the Invention's Compositions for Generation of Viruses The invention provides methods for producing a recombinant adeno-associated virus (rAAV) particle, comprising a) providing an expression vector comprising one or more of the nucleotide sequences described herein (e.g., a nucleotide sequence encoding a chimeric protein, a) wherein the encoded chimeric protein i) comprises at least a portion of wild type AAV Rep inhibitory amino acid sequence listed as SEQ ID NO:20 (i.e., encoded by the 564-bp DNA sequence from bp 1623 to bp 2186 of the AAV2 genome) and/or SEQ ID NO:02 (i.e., encoded by the 135-bp DNA sequence from bp 1782 to bp 1916 of the AAV2 genome, FIG. 4 panel B), and ii) has Rep-mediated nuclease activity, and b) wherein the recombinant nucleotide sequence comprises a scrambled polynucleotide sequence encoding the wild type AAV Rep inhibitory amino acid sequence listed as SEQ ID NO:20 and/or SEQ ID NO:02), and/or portion thereof, b) providing an adeno-associated virus (AAV) packaging cell, and c) transfecting the packaging cell with the expression vector to produce a recombinant adeno-associated virus (rAAV).

In one embodiment, the method further comprises detecting the presence of the produced recombinant adeno-associated virus (rAAV).

In a further embodiment, the method further comprises isolating the recombinant adeno-associated virus (rAAV).

In a particular embodiment, the method does not include (i.e., lacks) the step of transfecting the packaging cell with a helper virus [this highlights advantage of using ONLY one virus for expression of all genetic elements] [this highlights one advantage of the invention's AAV sequences, vectors, rAAV particles, and hybrid viruses (e.g., Ad/AAV) in that they tolerate the inclusion of all genetic elements in a single virus for the purpose of safely integrating a transgene into a safe region of the human genome, which provides a safer alternative to current approaches that use retroviruses and lentiviruses in gene replacement strategies.

I. Exemplary Applications of the Invention's Compositions for Expression of Nucleotide Sequences (e.g., In Gene Therapy and/or Vaccine Applications)

The invention's compositions (such as AAV nucleotide sequences, vectors, viruses (e.g., rAAV particles, and hybrid AAV particles such as Ad/AAV), and/or cells) are useful in several contexts, including, but not limited to, gene therapy and vaccine applications. Thus, in one embodiment, the invention provides methods for reducing one or more symptoms of disease in a mammalian subject, comprising administering a therapeutically effective amount of one or more of the invention's compositions (such as AAV nucleotide sequences, vectors, viruses (e.g., rAAV particles, and hybrid AAV particles such as Ad/AAV), and/or cells) to a mammalian subject in need of therapy. In particular embodiments the invention's compositions contain the recombinant nucleotide sequences described herein, and further contain a heterologous polynucleotide sequence (optionally operably linked to AAV ITR). The mammalian subject includes, without limitation, a subject that has a disease and a subject at risk of disease.

In one example, one or more of the invention's compositions (such as AAV nucleotide sequences, vectors, viruses (e.g., rAAV particles, and hybrid AAV particles such as Ad/AAV), and/or cells) are useful in gene therapy applications. In these applications, it is desirable that the heterologous polynucleotide sequence comprises a therapeutic sequence.

In another example, the invention's compositions (such as AAV nucleotide sequences, vectors, viruses (e.g., rAAV particles, and hybrid AAV particles such as Ad/AAV), and/or cells) are useful in vaccine applications. In these applications, it is desirable that heterologous polynucleotide sequence encodes an antigen polypeptide. While not necessary, in one embodiment the method further comprises detecting the immune response to the antigen polypeptide.

The invention's compositions (such as AAV nucleotide sequences, vectors, and/or viruses are administered in a therapeutic amount. The terms "therapeutic amount," "pharmaceutically effective amount," "therapeutically effective amount," "biologically effective amount," and "protective amount" are used interchangeably herein to refer to an amount that is sufficient to achieve a desired result, whether quantitative and/or qualitative. In particular, a therapeutic amount is that amount that delays, reduces, palliates, ameliorates, stabilizes, prevents and/or reverses one or more symptoms of the disease compared to in the absence of the composition of interest. Examples include, without limitation, tumor size and/or tumor number in cancer disease, glucose levels in blood and/or urine in diabetes, standard biochemical kidney function tests in kidney disease, etc. The terms also include, in another embodiment, an amount of the composition that reduces infection by a pathogen (e.g., HIV, malaria parasite, *Pseudomonas* species), regardless of whether disease symptoms are altered (i.e., increased or reduced).

In vaccine applications, the invention's compositions are preferably administered in an immunologically effective amount. In one embodiment, "immunogenically effective amount" and "immunologically-effective amount" refer to that amount of a molecule that elicits and/or increases production of an immune response (including production of specific antibodies and/or induction of a cytotoxic T lymphocyte (CTL) response) in a host upon vaccination.

Specific "dosages" can be readily determined by clinical trials and depend, for example, on the route of administration, patient weight (e.g. milligrams of drug per kg body weight). The term "delaying" symptoms refers to increasing the time period between exposure to the immunogen or virus and the onset of one or more symptoms of the exposure. The term "eliminating" symptoms refers to 100% reduction of one or more symptoms of exposure to the immunogen or virus.

As used herein, the actual amount, i.e., "dosage," encompassed by the term "pharmaceutically effective amount," "therapeutically effective amount," "immunologically effective," and "protective amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to achieve optimal efficacy but will depend on such factors as weight, diet, concurrent medication and other factors that those An effective amount of recombinant viral vector, such as rAAV and/or hybrid viruses is administered, depending on the objectives of treatment. An effective amount may be given in single or multiple doses. Where a low percentage of transduction can achieve a therapeutic effect, the objective of treatment is generally to meet or exceed this level of transduction. In some instances, this level of transduction can be achieved by transduction of only about 1 to 5% of the target cells, but is more typically 20% of the cells of the desired tissue type, usually at least about 50%, preferably at least about 80%, more preferably at least about 95%, and even more preferably at least about 99% of the cells of the desired tissue type (Carter, U.S. Pat. No. 7,785,888).

As a guide, the number of virus particles administered per injection will generally be between $1 \times 10^6$ and $1 \times 10^{14}$ particles, preferably, between $1 \times 10^7$ and $1 \times 10^{13}$ particles, more preferably $1 \times 10^9$ and $1 \times 10^{12}$ particles and even more preferably about $1 \times 10^{11}$ particles (Carter, U.S. Pat. No. 7,785,888).

The number of virus particles administered per intramuscular injection and per intravenous administration, for example, will generally be at least about $1 \times 10^{10}$, and is more typically $5 \times 10^{10}$, $1 \times 10^{11}$, $5 \times 10^{11}$, $1 \times 10^{12}$, $5 \times 10^{12}$ and on some occasions $1 \times 10^{13}$ particles (Carter, U.S. Pat. No. 7,785,888).

In one embodiment, the invention's methods further comprise the step of detecting the presence of at least, a portion of the vector in a cell of the treated subject.

In a further embodiment, it may be desirable to confirm the effectiveness of delivery of the invention's compositions (such as AAV nucleotide sequences, vectors, and/or viruses) to target cells. This can be monitored by several criteria. For example, samples removed by biopsy or surgical excision can be analyzed by in situ hybridization, PCR amplification using vector-specific probes, and/or RNAse protection to detect viral DNA and/or viral mRNA, such as rAAV DNA or RNA. Also, for example, harvested tissue, joint fluid and/or serum samples can be monitored for the presence of a protein product encoded by the recombinant viral vector with immunoassays, including, but not limited to, immunoblotting, immunoprecipitation, immunohistology and/or immunofluorescent cell counting, or with function-based bioassays. Examples of such assays are known in the art (Carter, U.S. Pat. No. 7,785,888).

Administration of the invention's compositions (such as AAV nucleotide sequences, vectors, and/or viruses to a mammalian subject, so as to introduce a sequence of interest into a mammalian cell and/or express a gene product of interest in a mammalian cell) can be accomplished in several ways, that include, but are not limited to, intramuscular administration, intradermal administration, intravenous administration, subcutaneous administration, aerosol administration, oral administration, and/or sub-lingual administration. Administration includes direct injection of the composition(s) to a tissue or anatomical site. Injection can be, for example, intra-arterial, intravenous, intramuscular or intra-articular. Administration may be parenteral, oral, intraperitoneal, intranasal, topical, etc. Parenteral routes of administration include, for example, subcutaneous, intravenous, intramuscular, intrastemal injection, and infusion routes. Methods of transducing cells of blood vessels are described, for example, in PCT US97/103134.

Another preferred mode of administration of compositions of the invention is through naso-pharyngeal and pulmonary routes. These include, but are not limited to, inhalation, transbronchial and transalveolar routes. The invention includes compositions suitable for administration by inhalation including, but not limited to, various types of aerosols and powder forms. Devices suitable for administration of compositions by inhalation include, but are not limited to, atomizers and vaporizers (Carter, U.S. Pat. No. 7,785,888).

The compositions of the invention may be administered before, concomitantly with, and/or after manifestation of one or more symptoms of a disease or condition. Also, the invention's compositions may be administered before, concomitantly with, and/or after administration of another type of drug or therapeutic procedure (e.g., surgery, radiation, etc.). For example, in the case of pathogen infection, the invention's compounds may be administered before, concomitantly with, and/or after administration of antibiotics and/or antivirals.

Administration may be in vivo and/or or ex vivo to deliver a transgene to an individual, preferably a mammal. Such methods and techniques are known in the art. See, for example, U.S. Pat. No. 5,399,346. Generally, cells are removed from an individual, transduced by recombinant viral vectors, such as rAAV vectors, in vitro, and the transduced cells are then reintroduced into the individual. Cell suitable for ex vivo delivery are known to those skilled in the art and include, for example, various types of stem cells (Carter, U.S. Pat. No. 7,785,888).

The selection of a particular composition, dosage regimen (i.e., dose, timing and repetition) and route of administration will depend on a number of different factors, including, but not limited to, the subject's medical history and features of the condition and the subject being treated, and may be determined empirically (Carter, U.S. Pat. No. 7,785,888).

In one embodiment of the invention, methods for identifying a phenotype associated with expression of a coding sequence of a recombinant viral vector of the invention are provided, comprising subjecting host cells containing a recombinant viral vector of the invention to conditions which allow expression; comparing a phenotype of these expressing cells to a phenotype of cells which lack the recombinant viral vector; wherein a phenotypic difference indicates a phenotype associated with expression of the coding sequence. In other embodiments, phenotypic screening is accomplished by contacting a host cell with a recombinant viral vector described herein under conditions that allow uptake of the vector; assaying the cell for expression of the heterologous coding region of the vector; comparing a phenotype of the cell expressing the heterologous coding region with a phenotype of a cell that lacks the vector. A phenotypic difference indicates that the phenotype of the cell expression the heterologous sequence is a phenotype associated with expression of the coding region. Such phenotypic characteristics could in turn provide valuable information regarding function(s) of the coding sequence, as well as its potential role in health or contributing to disease states, and as a useful drug target (Carter, U.S. Pat. No. 7,785,888).

EXPERIMENTAL

The following examples serve to illustrate certain embodiments and aspects of the present invention and are not to be construed as limiting the scope thereof.

Example 1

Materials and Methods
De Novo Synthesized Constructs:
All de novo synthesized sequences were synthesized and cloned into pUC13 by GenScript USA. Scrambled Rep, Deoptimized Rep, were designed using a program previously described (13). The sequences were designed with unique restriction sites SbfI and SwaI flanking them as well as a unique R.E AfeI at bp 661 of the AAV2 genome to allow ease of manipulation. A naturally occurring R.E BstBI site that occurs at bp 1623 of of the AAV2 genome was retained.

Rep78 Design I, II, III and IV was designed using algorithms described in the art (Coleman et al., Science 320:1784 (2008). S (wt3) Rep contains wild type Rep sequences from AAV2 bp 1623 to 2186. S (wt1,2) Rep contains scrambled Rep sequences from AAV2 bp 1623 to 2186. The constructs shown in FIG. 3 delimit the 135 bp interval from bp 1782 to bp 1916 of the AAV2 genome.

Plasmids and Cloning:

For detection of expression levels from wild-type, scrambled and Deoptimized Rep ORFs, each ORF was PCR amplified without the stop codon and cloned into pCMV-3Tag3A (Stratagem, USA) under the CMV minimal promoter, with a 3× C terminal flag tag. The first step in the construction of all viral constructs was the cloning of the required transgene into a shuttle vector. All shuttle vectors were derived from pAd/AAV-EGFP-Neo (18).

pTROTS-wt was constructed by PCR amplification and stepwise cloning of the TRE-pTK-Rep78 cassette and the pCMV-tTS cassette from plasmid pΔ28 (a gift from Dr. Mavilio, Italy) in place of the pCMV-EGFP-Neo cassette in pAd/AAV-EGFP-Neo. The Rep78 ORF was flanked by a unique SbfI site upstream and SwaI site downstream, and these sites were used subsequently to swap in the Scrambled and Deoptimized Rep ORFs from pUCScr and pUCDeopt in place of wild-type, to construct pTROTS-Scr and pTROTS-Deopt.

For localization of the sequence signal, various sections of the Scrambled ORF were replaced with the corresponding wild-type sequence in frame. AAV2 bp 321 to bp 983 of the wild type Rep sequence was amplified from pTROTS-wt by PCR and swapped into pTROTS-Scr replacing the corresponding Scrambled sequence. Since BstBI was not unique within pTROTS-Scrambled, pTROTS Scr (wt2) and pTROTS Scr (wt3) had to be constructed in two steps. The AAV2 bp 984 to bp 1623 of wild-type Rep (fragment wt2) was PCR amplified from pTROTS-WT and cloned into the pUCScr, making pUCScr(wt2). This entire Rep cassette was excised out of by restriction digestion with R.E SbfI and SwaI and inserted into the pTROTS backbone, making pTROTS-Scr(wt2). Similarly, pUCScr(wt3) was constructed by excision of AAV2 bp 1623 to bp 2186 of wild-type Rep (wt3) from pTROTS-wt and ligation into similarly digested pUCScr, resulting in pUCScr(wt3). The entire Rep coding ORF was then swapped into pTROTS backbone, resulting in pTROTS-Scr(wt3). Similarly, shuttle vectors for construction of Ad/Rep78-I to Ad/Rep78-W were constructed by excision of the entire Rep coding ORF from the pUC13 clone by double digestion with R.Es SbfI and SwaI and insertion into the sites within pTROTS-wt, replacing the wtRep78 ORF.

phu1Scr and phu1Deopt have the Scrambled and Deoptimized Rep constructs respectively, expressed under an hu1 promoter. A left end shuttle vector carrying the hu1 promoter and SV40 poly A was constructed by digestion of the cassette from peDNA3-hu1polyA (17) by flanking XbaI restriction sites and cloned in place of the pCMV-EGFP-Neo cassette in pAd/AAV-EGFP-Neo, generating pITR-packaging-hu1polyA-3330. Unique BglII and HindIII restriction enzyme sites lay between the hu1 promoter and the poly A sequence. The Scrambled Rep78 ORF was PCR amplified from pUCScr and inserted into the BglII site in the vector, and the orientation checked by sequencing. phu1Deopt was constructed by PCR amplification of the Deoptimized ORF from pUCDeopt and introduced into the BglII HindIII double digested vector backbone.

For the construction of a shuttle vector for Ad/AAVFVIII, 2 copies of the AAV integration efficiency element was originally cloned upstream of the AAV ITR in pAd/AAVCMV-EGFP-Neo. The IRES-EYFP cassette from pIRES-EYFP (Stratagene, USA) was PCR amplified and cloned downstream of the 5.6 Kb pPF4-FVIII cassette in pBSPF4FVIII (19). This pPF4-FVIII-EYFP cassette was then excised out by NotI digestion and inserted into pAd/AAV CMV-EGFP-Neo and transformed into Max Efficiency Stbl2 cells (Invitrogen, USA). Further details of plasmid construction available on request. All restriction enzymes used were from NEB USA. PfuUltra High-Fidelity DNA Polymerase (Stratagene, USA) was used for all PCR amplification steps.

Virus Construction:

All viruses were constructed by homologous recombination in BJ5183 cells (Stratagene, USA), between the shuttle vectors and pTG3602 ΔE3 F5/35. pTG3602 (20) contains the intact WT Adenoviral genome and was obtained from Transgene, S. I (Strasbourg, France). Details of cloning from Pat.

Positive clones were transformed into DH5α cells to scale up production. Ad/AAV fVIII alone was electroporated into SURE electroporation competent cells (Stratagene, USA) as DH5α cells were found to be unsuitable for maintenance of the intact AAV ITR. Transformed clones were confirmed by restriction digestion.

5 μg of viral DNA was linearized and used to transfect 80% confluent 6 cm plates of HEK 293 packaging cells using Fugene 6 (Roche, USA), following manufacturer's directions. At day 10, cells were lysed by freeze thaw and lysate used to infect fresh cells for the development of cytopathic effect (CPE).

Excision Assay:

6 cm plates of 293 cells were co-infected with Ad/AAVFVIII and either Ad/sRep78 or Ad/dRep78 at an MOI of 50 each. 1 hr after infection, cells were induced with doxycycline. Cells infected with Ad/AAVFVIII only served as the negative control, while C12 cells co-infected with Ad/AAVFVIII and Wild-type Adenovirus served as a positive control. In the case of Rep expressing plasmids, 293 cells in 6 well plates were transfected with 2 μg of the plasmid using Fugene 6 (Roche, USA) following manufacturer's instructions, 48 hours before infection with Ad/AAVFVIII.

48 hours post infection, cells were lysed and Hirt extrachromosomal DNA isolated. One quarter of the total DNA prep was run out on a 0.8% agarose gel and transferred onto nylon membranes (Roche, USA). The presence of excision products was detected by Southern blotting, following standard procedure. Non radioactive Digoxigenin labeled probes (Roche, USA) which recognized a ~700 bp sequence at the junction of pPF4-FVIII were used.

Viral Replication Assay:

To compare the ability of viruses carrying Rep to replicate, a modified DpnI viral replication assay was performed. 293 cells in 6 well plates were transfected with linearized viral constructs. At various time points, cells were washed and low molecular weight (Hirt) extrachromosomal DNA isolated. 100 ng DNA was digested with DpnI overnight. DpnI requires dam methylated substrates. As the transfected viral DNA is of bacterial origin, DpnI digestion ensures that viral DNA detected is only replicated DNA. Southern blot analysis was completed using non-radioactive Digoxigenin labeled probes using the DIG Easy Hyb kit (Roche) following manufacturer's protocol.

Immunoblotting: HeLa cells in 6 well plates were transfected with equal amounts of pCMV-wtRep78-flag, pCMV-sRep78r-flag, or pCMV-dRep78-flag using fugene6 (Roche, USA) following manufacturer's instructions. 48 hours post transfection, cells were lysed using NP40 lysis buffer (50 mM Tris.HCl pH8.0, 150 mM NaCl, 1% NP-40). Equal amounts of reduced, denatured protein was separated on a 4-15% polyacrylamide gel (Biorad, USA) and transferred onto a nitrocellulose membrane. Membranes were blocked in 3% milkfat and incubated with primary antibody (mouse monoclonal anti-flag M2 (Sigma, USA) or mouse monoclonal anti-GAPDH MAB374 (Millipore, USA)) for 1 hour at room temperature, followed by incubation for 1 hour at RT with the secondary antibody (ECL Anti-mouse IgG Horseradish peroxidase linked F(ab')$_2$ fragment from sheep (GE Healthcare, UK)). Detection was performed using the Pierce ECL Western Blotting substrate (Thermo Scientific, USA) following standard protocol.

Example 2

Modification of Rep ORF:

To construct a first generation Ad carrying Rep78, the inventors expressed Rep under a tightly regulated tetracycline inducible promoter within an ΔE1ΔE1 F5/35 Adenovirus. The fiber knob of this Ad5 was replaced with that of Ad35 to allow it to infect hematopoietic cells (3). The tetracycline inducible Rep78 expression cassette, has been previously used successfully for the construction of a helper dependent Adenovirus carrying Rep78 (9). Surprisingly, the inventors found that the same construct on an E1 deleted backbone was incapable of replication, showing no signs of viral growth in spite of multiple passages in HEK 293 packaging cells. The inventors hypothesized that the replicative functions provided by multiple helper virus genomes in trans to the helper dependent virus allowed replication, whereas a single genome carrying both Adenoviral genes and the Rep expression construct was unable to escape Rep's inhibitory effect.

To elucidate the relative contribution of the sequence of the Rep ORF and Rep protein levels on this apparently cis acting inhibitory effect, the inventors modified the 1865 bp Rep78 nucleotide sequence in silico. The inventors utilized an algorithm (13) that allowed us to modify the nucleotide sequence of Rep78 by about 20% to about 30% without affecting the amino acid sequence encoded, using synonymous codons (Sequence alignments in FIG. 10). Two modified Rep sequences, Scrambled and Deoptimized, were designed and synthesized de novo.

The Scrambled sequence randomly mixes synonymous codons, resulting in a nucleotide sequence that differs from the wild-type sequence by about 30%. The protein expressed from this ORF is identical to wild-type Rep78. This sequence aims to disrupt any sequence specific signal, without affecting Rep78 expression levels.

Within the Deoptimized sequence, synonymous codons are specifically paired into under-utilized codon pairs (FIG. 1a). Synonymous codons can be paired in multiple ways to encode the same 2 adjacent amino acids. However, in nature a strong codon pair bias is found to exist, resulting in the disproportionate representation of some codon pairs over others (14). This codon pair bias is independent of codon frequency and is found to affect translation rates. Utilization of under-represented codon pairs such as those in Deoptimized sequences, therefore, results in an ORF that is expressed at lower levels due to inefficient translation (15). Thus, the Deoptimized Rep construct not only differs from the nucleotide sequence of wild-type Rep by 20%, presumably disrupting any sequence specific signal, but also further reduces levels of Rep78 expression from the tetracycline (Tet) inducible promoter. Confirmation of Deoptimized Rep's reduced ability to express protein was obtained by immunoblot analysis of transfected C-terminal flag tagged constructs, expressed under pCMV. Protein levels from Wild-type and Scrambled Rep were found to be comparable to each other and roughly double that of Deoptimized (FIGS. 1B and 1C)

Example 3

Modification of Rep ORF Allows Replication of Adenovirus:

The Scrambled and Deoptimized Rep constructs were cloned downstream of the tetracycline inducible promoter, in place of the wild-type Rep ORF, within the fiber modified first generation Adenovirus genome, generating infectious clones pAd/sRep78 and pAd/dRep78 (FIG. 2A). These viral constructs were linearized and transfected into HEK 293 packaging cells and passaged every 10 days onto fresh cells, until the development of CPE was observed. As mentioned earlier, no signs of viral replication could be observed with pAd/WTRep78 even with passaging up to 50 days. However, complete CPE was observed with both pAd/sRep78 and pAd/dRep78 within a total of 15 days from transfection. Production of both viruses could be scaled up with infectious virus yields comparable to each other and to Ad/AAVFVIII (Table 1), proving a clear role for the sequence of Rep in the inhibition of Adenoviral replication.

TABLE I

| Viral titers | |
|---|---|
| Virus | Titer[†] (PFU/mL × $10^8$) |
| Ad/sRep | 9.50 + 0.50 |
| Ad/dRep | 9.50 + 0.25 |
| Ad/s(wt1) Rep | 8.13 + 0.12 |
| Ad/s(wt2) Rep | 8.75 + 0.25 |
| Ad/s(wt1, 2) Rep | 8.13 + 0.12 |
| Ad/Rep II | 11.5 + 0.75 |
| Ad/Rep III | 10.4 + 0.37 |
| Ad/Rep IV | 9.38 + 0.12 |
| Ad/HU1-1/sRep | 7.50 + 0.75 |
| Ad/HU1-1/dRep | 8.00 + 0.50 |
| Ad/AAV/PF4/BDD | 10.5 + 0.50 |

[†]Titers were calculated by serial dilution and plaque assay in HEK 293 packaging cells, and are reported in plaque-forming units (PFU)/mL as the mean + SEM from two distinct determinations

TABLE 2

Putative transcription factor binding sites unique to wtRep78 bp1461-1596 identified by TESS (Transcription Element Search System) (326)

|  | Transcription Factor | Begin bp no. | Sequence |
|---|---|---|---|
| 1 | T00111 c-Ets-1 T00112 c-Ets-1 T00114 c-Ets-1 54 T00115 c-Ets-1 68 T00684 PEA3 T00685 PEA3 T00686 PEA3 | 97 | SMGGAWGY |
| 2 | T00506 MEF1 T00519 Myf-3 T00524 MyoD T00525 MyoD T00526 MyoD T00527 MyoD T01128 MyoD | 69 | GTCAGTTG |
| 3 | _00000 ASF-1_00000 MSN4_00000 deltaCREB | 88 | ACGTCA |
| 4 | T00049 ATF T00050 atf1 T00132 c-Jun T00163 CREB T00164 CREB T00166 deltaCREB T00167 CRE-BP1 T00846 TREB-1 T00942 EivF T01095 ATF3 | 88 | ACGTCA |
| 5 | T00163 CREB | 33 | TGACG |
| 6 | T00051 ATF T00052 ATF-a T00053 ATF-adelta T00054 ATF-like T00442 47-kDa CRE bind. prot. T00968 ATF-1 | 33 | TGACGYMR |
| 7 | _00000 LRF-1 | 88 | ACGTCA |
| 8 | _00000 ATF-1 | 88 | ACGTCA |
| 9 | T00134 c-Jun T00893 v-Jun | 66 | CGAGTCAG |
| 10 | T00074 gammaCAC1 T00075 gammaCAC2 T00077 CACCC-binding factor | 3 | GGGTG |
| 11 | _00000 MIG1 | 27 | CCCCAG |
| 12 | T00765 SRF (504 AA) | 41 | ATATA |
| 13 | _00000 RC2 | 18 | AAGACC |
| 14 | _00000 GCN4 | 67 | GAGTCA |
| 15 | _00000 B-factor | 42 | TATAAGT |
| 16 | T00386 HSTF | 14 | AGAAA |
| 17 | T00029 AP-1 | 90 | GTCA |
| 18 | _00000 HBP-1 | 88 | ACGTCA |
| 19 | T00140 c-Myc | 71 | CAGTTG |
| 20 | T00029 AP-1 T00123 c-Fos T00133 c-Jun T00167 CRE-BP1 T00989 CREB T01313 ATF3 T02361 CREBbeta | 33 | TGACGCA |
| 21 | T00182 DBF4 T00270 ETF T00530 NC1 T00794 TBP T00798 TBP T00817 TGIIA T00818 TFIIB T00820 TFIID T00835 TMF T00862 UBP-1 T02216 TFIIA-alpha/beta precursor (majorT02216 T02217 TFIIA-alpha/beta precursor (minorT02217 T02224 TFIIA-gamma | 42 | TATAA |
| 22 | T00074 gammaCAC1 T00075 gammaCAC2 T00077 CACCC-binding factor | 59 | GGGTG |
| 23 | T00321 GCN4 | 67 | GAGTCA |
| 24 | T00029 AP-1 | 69 | GTCA |
| 25 | T00029 AP-1 | 23 | CCGCCCCC |
| 26 | T00878 USF2 T02115 USF2 T02377 USF2b | 33 | TGACGCA |
| 27 | T00422 IRF1 T00425 IRF-2 | 45 | AAGTGA |
| 28 | T00968 ATF-1 | 88 | ACGTCA |

TABLE 2-continued

Putative transcription factor binding sites unique to wtRep78 bp1461-1596 identified by TESS (Transcription Element Search System) (326)

| | Transcription Factor | Begin bp no. | Sequence |
|---|---|---|---|
| 29 | _00000 TREB-1 | 88 | ACGTCA |
| 30 | T00354 HBP-1 T00938 HBP-1b T01393 HBP-1b(c1)T01394 HBP-1a(1) T01395 HBP-1a(c14) T02789 bZIP910 | 88 | ACGTCA |
| 31 | T00051 ATF T00052 ATF-a T00053 ATF-adelta T00054 ATF-like T00442 47-kDa CRE bind. prot. T00968 ATF-1 | 86 | YKRCGTCA |
| 32 | T00111 c-Ets-1 T00112 c-Ets-1 T00114 c-Ets-1 54 T00115 c-Ets-1 68 T00684 PEA3 T00685 PEA3 T00686 PEA3 | 97 | SMGGAWGY |
| 33 | T00506 MEF1 T00519 Myf-3 T00524 MyoD T00525 MyoD T00526 MyoD T00527 MyoD T01128 MyoD | 69 | GTCAGTTG |

Surprisingly, the inventors noted the lack of any apparent difference in the ability of Ad/sRep78 and Ad/dRep78 to grow in spite of their differences in Rep expression level. It indicated that at least under the control afforded by the tetracycline inducible system, the major role in inhibition of Ad replication was played by a sequence specific signal and modification of that signal alone was sufficient to completely lift inhibition.

The ability of Ad/dRep78 and Ad/sRep78 to produce functional Rep78 was confirmed by an excision assay which depends on Rep's ability to cleave at a folded AAV ITR (FIG. 2A). The inventors used a first generation Ad/AAV carrying a single AAV ITR downstream of the transgene as a substrate for cleavage. Cleavage at the ITR by Rep would result in the release of an ~8 Kb excision product. HEK 293 cells were co-infected with the substrate virus Ad/AAV FVIII and either Ad/sRep78 or Ad/dRep78 in the presence or absence of doxycycline. Hirt DNA was prepared 48 hours post infection and cleavage products were analyzed by southern blot with a substrate specific probe. Monomeric and dimeric excision products that were dependent on the presence of Ad/sRep78 or Ad/dRep78 were detected (FIGS. 2B and 2C). Leaky expression resulted in some excision even in the absence of doxycycline, and a several fold increase in intensity seen with the addition of dox. Excision in C12 cells, a HeLa cell line derivative that inducibly expresses Rep and Cap (16) was used as a positive control.

Example 4

Rep Protein Expression is Not Required for Inhibition of Ad Replication:

The fact that Ad/sRep78 and Ad/dRep78 replicate equally efficiently in spite of Ad/sRep78 expressing double the amount of Rep protein indicates that accumulation of Rep protein likely played no part in the inability of Ad/wtRep78 to replicate. However, the tetracycline inducible system has been shown to tightly regulate Rep protein expression in transfected cells and as mentioned earlier, has been previously used for the successful production of a helper dependent Ad carrying Rep78 (9). Further, the dependence of AAV on relative time of infection and relative copy number to inhibit Ad replication has lead to a proposal that the accumulation of Rep expression at the initial stages of infection is responsible for inhibition of Ad replication (11). Therefore, to truly understand the role of Rep78 protein expression in the inhibition of Adenoviral replication, the inventors expressed the modified Rep ORFs under a constitutive 243 bp human U1-1 small nuclear RNA promoter (pHU-1) (17). ΔE1ΔE3 Adenoviruses carrying the hu1-sRep78 and hu1-dRep78 constructs were capable of normal rates of replication, with CPE observed 15 days after transfection. Viral yield (Pfu/cell) from Ad/hu1-sRep78 and Ad/hu1-dRep78 was comparable to both Ad/AAV FVIII, Ad/sRep78 and Ad/dRep78 (Table 1). These results prove that a high level of Rep78 protein expression can be tolerated by replicating Adenoviruses and the dramatic inhibitory effects seen are mainly due to signals within the sequence of the Rep ORF.

Example 5

Localization of Signal:

To localize the sequence specific inhibitory signal, the inventors modified the Scrambled Rep ORF to create—S (wt1) Rep, S (wt2) Rep, and S (wt3) Rep (FIG. 3A). In each of these constructs, using unique internal restriction sites, sections representing about $\frac{1}{3}^{rd}$ (600 bps) of the entire Scrambled Rep sequence were replaced with that of WT Rep, in frame. These modified constructs were then inserted downstream of the tetracycline inducible promoter in place of scrambled Rep within Ad/sRep78, generating, Ad/S (wt1) Rep, Ad/S (wt2) Rep and Ad/S (wt3) Rep. The scrambled sequence was chosen to be modified as it expresses similar amounts of Rep78 protein as the wild-type sequence. Presence of the entire inhibitory sequence within any of these ~600 bp sections should inhibit the replication of the virus carrying it. When linearized and transfected into 293 cells, Ad/S (wt1) Rep and Ad/S (wt2) Rep both showed signs of viral replication shortly after primary infection and complete CPE within 15 days of transfection, and yielded titers comparable to Ad/sRep78 (Table1). Ad/S (wt3) Rep showed no signs of replication for up to 40 days post transfection, indicating that the sequence specific signal is localized within the 3' 564 bps, in the region encompassing bp 1623 to bp 2186 of the AAV2 genome.

To confirm that the inhibitory signal lay completely within the 3' 564 bp of the WT Rep78 sequence, the inventors then modified the WT Rep78 sequence replacing the 3' 564 bps alone with the corresponding Scrambled Rep78 sequence, creating S (wt1,2) Rep (FIG. 3A). When inserted downstream of the tetracycline inducible system within a first generation Adenovirus, substitution of these 564 bps of the WT Rep sequence with Scrambled Rep sequence alone was sufficient to lift inhibition and allow replication of the Adenovirus carrying it, comparable to Ad/sRep78 (Table 1).

In an alternative approach, the inventors used an algorithm to further narrow down the sequence specific inhibitory signal. The algorithm generates 4 different full length Rep encoding sequences (Design I, II, III and IV). The DNA sequence of each of these constructs is sub-divided into 14 segments, 123-135 bps in length, consisting of corresponding sequences from either the wild-type (WT) or scrambled (Scr) sequence resulting in a 'checkered' pattern of segments (FIG. 3B). The arrangement of segments in the 4 full length sequences is such that, when the 4 sequences are lined up, every column (consisting of the corresponding segment in each of the 4 constructs) is unique. When cloned into an expression cassette in a viral backbone, the presence of the sequence specific inhibitory signal in a particular segment will result in all viruses with the WT sequence in that segment dying. Thus a unique pattern of viruses that live and die is associated with every possible location of the sequence specific signal.

The 4 modified sequences were synthesized de novo by Genscript, USA and cloned downstream of the tetracycline inducible promoter, in place of the wt Rep cassette. These cassettes were inserted into first generation Ads, generating Ad/Rep I, Ad/Rep II, Ad/Rep III and Ad/Rep IV (FIG. 3B). Each of these infectious clones were linearized and transfected into 293 cells. Ad/Rep II, Ad/Rep III and Ad/Rep IV replicated and yielded titers comparable to Ad/sRep78 (Table 1). Ad/Rep I showed no signs of viral replication up to 50 days post transfection. The 135 bp segment implicated by the pattern of viruses capable of replication (Ad/Rep II, Ad/Rep III, and Ad/Rep IV) and incapable of replication (Ad/Rep I), encompassed bp 1782 to bp 1916 of the AAV2 genome (FIG. 3B—segment indicated by an asterisk). Based on the arrangement of segments within the 4 sequences, some or all of the Rep sequence(s) that inhibits Ad growth lies within this 135 bp fragment. This sequence lies well within the boundaries of bp 1623 to bp 2186 of the AAV2 genome identified by the inability of S (wt3) Rep to grow.

Example 6

Additional Delineation of Rep Inhibitory Sequences.

Figure 14:
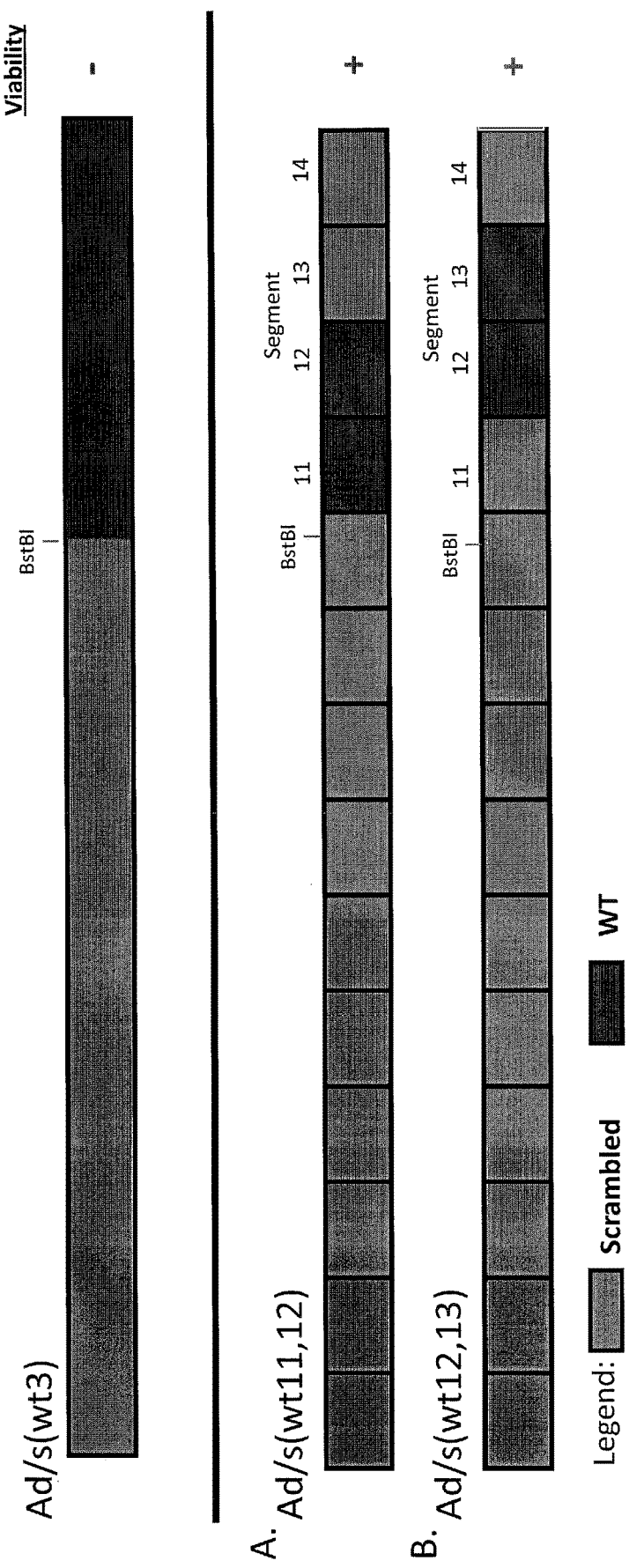
FIG. 14. Additional delineation of Rep inhibitory sequences. Chimeric Rep genes were assembled by polynucleotide segment swaps encompassing discrete segments of wild-type or scrambled sequences, and viability established by adenoviral replication. (A) Rep78 chimer encompassing wild-type 135 bp sequences corresponding to segment 11 and 12 on the background of sRep. (B) Rep78 chimer encompassing wild-type 135 bp sequences corresponding to segment 12 and 13 on the background of sRep.

Chimeric Rep genes were assembled by polynucleotide segment swaps encompassing discrete segments of wild-type or scrambled sequences, and viability established by adenoviral replication. The results are shown on FIGS. 14-16. These results demonstrate that scrambled sequences within segment 11, segment 13 and segment 14 are capable of rescuing the inhibitory effect of the WT Rep ORF on Ad replication

REFERENCES

1. Im D-S & Muzyczka N (1989) Factors that bind to adeno-associated virus terminal repeats. *Journal of Virology* 63(7):3095-3103.
2. Im D-S & Muzyczka N (1990) The AAV origin binding protein Rep68 is an ATP-dependent site specific endonuclease with DNA helicase activity. *Cell* 61(3):447-457.
3. Shayakhmetov D M, Thalia Papayannopoulou, Stamatoyannopoulos G, & Lieber A (2000) Efficient Gene Transfer into Human CD34$^+$ cells by a Retargeted Adenoviral Vector. *Journal of Virology* 74(6):2567-2473.
4. Krasnykh V N, Galina V. Mikheeva, Douglas J T, & Curiel D T (1996) Generation of Recombinant Adenovirus Vectors with Modified Fibers for Altering Viral Tropism. *Journal of Virology* 70(10):6839-6836.
5. Gall J, Kass-Eisler A, Leinwand L, & Falck-Pederson E (1996) Adenovirus Type 5 and 7 Capsid Chimera: Fiber Replacement Alters Receptor Tropism without Affecting Primary Immune Neutralization Epitopes. *Journal of Virology* 70(4):2116-2123.
6. Casto B C, Atchison R W, & Hammon M W (1967) Studies on the Relationship between Adeno-Associated virus Type I (AAV-1) and Adenoviruses I. Replication of AAV-1 in Certain Cell Cultures and Its Effect on Helper Adenovirus. *Virology* 32:52-59.
7. Timpe J M, Verrill K C, & Trempe J P (2006) Effects of Adeno-Associated Virus on Adenovirus Replication and Gene Expression during Coinfection. *Journal of Virology* 80(16):7807-7815.
8. Weitzman M D, Fisher K J, & Wilson J M (1996) Recruitment of Wild-Type and REcombinant Adeno-Associated Virus into Adenovirus Replication Centers. *Journal of Virology* 70(3):1845-1854.
9. Recchia A, Perani L, Sartori D, Olgiati C, & Mavilio F (2004) Site specific integration of functional transgenes into the human genome by Adeno/AAV hybrid vectors. *Molecular Therapy* 10(No. 4):660-670.
10. Wang H & Lieber A (2006) A Helper-Dependent Capsid-Modified Adenovirus Vector Expressing Adeno-Associated Virus Rep78 Mediates Site-Specific Integration of a 27-Kilobase Transgene Cassette. *Journal of Virology* 80(23):11699-11709.
11. Carlson C A, Shayakhmetov D M, & Lieber A (2002) An Adenoviral Expression System for AAV Rep78 Using Homologous Recombination. *Molecular Therapy* 6(1): 91-98.
12. Fisher K J, Kelley W M, Burda J F, & Wilson J M (1996) A Novel Adenovirus-Adeno-Associated Virus Hybrid Vector That Displays Efficient Rescue and Delivery of the AAV *Genome. Human Gene Therapy* 7:2079-2087.
13. Coleman J R, et al. (2008) Virus Attenuation by Genome-Scale Changes in Codon Pair Bias. *Science* 320(5884):1784-1787.
14. Gutman G A & Hatfield G W (1989) Nonrandom utilization of codon pairs in *Escherichia coli. Proc. Natl. Acad. Sci. U.S.A.* 86(10):3699-3703.
15. Buchan J R, Aucott L S, & Stansfield I (2006) tRNA properties help shape codon pair preferences in open reading frames. (Translated from eng) *Nucleic Acids Res* 34(3):1015-1027 (in eng).
16. Clark K, Voulgaropoulou F, & Johnson P (1996) A stable cell line carrying adenovirus-inducible rep and cap genes allows for infectivity titration of adeno-associated virus vectors. *Gene Therapy* 3(12):1124-1132.
17. Gnatenko D, et al. (1999) Human factor VIII can be packaged and functionally expressed in an adeno-associated virus background: applicability to haemophilia A gene therapy. *British Journal of Haematology* 104(1):27-36.
18. Ziv S, Dmitri G, Bahou W F, & Hearing P (2000) Adeno-associated virus (AAV) Rep protein enhances the generation of a recombinant mini-adenovirus (Ad) utilizing an Ad/AAV hybrid virus. *Journal of Virology* 74(22): 10381-10389.

19. Damon A L, et al. (2008) Altered bioavailability of platelet-derived factor VIII during thrombocytosis reverses phenotypic efficacy in haemophilic mice. *Thrombosis and Haemostasis* 100(6):1111-1122.
20. Chartier C, et al. (1996) Efficient Generation of Recombinant Adenovirus Vectors by Homologous Recombination in *Escherichia coli. Journal of Virology* 70(7):4805-4810.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiment, it should be understood that the invention as claimed should not be unduly limited to such specific embodiments. Indeed, various modifications of the described modes for carrying out the invention which are obvious to those skilled in the art and in fields related thereto are intended to be within the scope of the following claims.

---

We claim:

1. A method for detecting a portion of wild type AAV Rep inhibitory nucleotide sequence that reduces replication by a hybrid Adenovirus that contains said portion, comprising
   a) providing
      i) a first hybrid Adenovirus vector comprising a first nucleotide sequence comprising a scrambled polynucleotide sequence encoding a portion of wild type AAV Rep inhibitory amino acid sequence listed as SEQ ID NO:20,
      ii) a second hybrid Adenovirus vector comprising a second nucleotide sequence, wherein the second nucleotide sequence is produced by substituting a portion of the scrambled polynucleotide sequence with a corresponding portion of wild type AAV Rep inhibitory nucleotide sequence listed as SEQ ID NO:17, and
      iii) a host cell that is permissive for the hybrid Adenovirus,
   b) transfecting
      i) the first hybrid Adenovirus vector into the permissive cell under conditions to produce a first hybrid Adenovirus that comprises a first amino acid sequence encoded by the first nucleotide sequence, and
      ii) the second hybrid Adenovirus vector into the permissive cell under conditions to produce a second hybrid Adenovirus that comprises a second amino acid sequence encoded by the second nucleotide sequence, and
   c) determining the level of replication of the first hybrid Adenovirus and of the second hybrid Adenovirus in the transfected permissive cell, wherein a reduced level of replication of the second hybrid Adenovirus compared to the first hybrid Adenovirus identifies the portion of wild type AAV Rep inhibitory nucleotide sequence as reducing replication by the hybrid Adenovirus.

* * * * *